US008501709B2

(12) United States Patent
Herdewijn et al.

(10) Patent No.: US 8,501,709 B2
(45) Date of Patent: Aug. 6, 2013

(54) PHOSPHONATE NUCLEOSIDES USEFUL AS ACTIVE INGREDIENTS IN PHARMACEUTICAL COMPOSITIONS FOR THE TREATMENT OF VIRAL INFECTIONS, AND INTERMEDIATES FOR THEIR PRODUCTION

(75) Inventors: Piet Herdewijn, Wezemaal (BE); Christophe Pannecouque, Heverlee (BE); Tongfei Wu, Leuven (BE); Erik De Clercq, Bierbeek (BE)

(73) Assignee: K.U.Leuven Research & Development, Leuven (BE)

( * ) Notice: Subject to any disclaimer, the term of this patent is extended or adjusted under 35 U.S.C. 154(b) by 0 days.

(21) Appl. No.: 13/291,781

(22) Filed: Nov. 8, 2011

(65) Prior Publication Data

US 2012/0108531 A1 May 3, 2012

Related U.S. Application Data

(63) Continuation of application No. 10/598,535, filed as application No. PCT/BE2005/000032 on Mar. 4, 2005, now Pat. No. 8,076,310.

(60) Provisional application No. 60/552,730, filed on Mar. 15, 2004.

(30) Foreign Application Priority Data

Mar. 4, 2004 (GB) .................................. 0404891.4
Apr. 5, 2004 (GB) .................................. 0407712.9

(51) Int. Cl.
*A61K 31/70* (2006.01)
*C07H 19/00* (2006.01)
*C07H 19/04* (2006.01)
*C07H 19/20* (2006.01)

(52) U.S. Cl.
USPC .............. 514/47; 514/48; 514/51; 536/26.23; 536/26.26

(58) Field of Classification Search
None
See application file for complete search history.

(56) References Cited

U.S. PATENT DOCUMENTS 8,076,310 B2 * 12/2011 Herdewijn et al. ............. 514/45

OTHER PUBLICATIONS

Wu et al.(I), "Deoxythreosyl Phosphonate Nucleosides as Selective Anti-HIV Agents," Journal American Chemical Society, 127(14), 5056-5065 (Mar. 22, 2005).*
Kempeneers et al., "Recognition of Threosyl Nucleotides by DNA and RNA Polymerases," Nucleic Acids Research, 31(21), 6221-6226 (Nov. 1, 2003).*

Wu et al. (II), "Base-Pairing Systems Related to TNA: [alpha]-Threofuranosyl Oligonucleoitdes Containing Phosphoramidate Linkages," Organic Le0.0.tters, 4(8), 1279-1282 (Mar. 16, 2002, (web publ. date)).*
Kline et al., "(13C)-Substituted Erythronucleosides: Synthesis and Conformational Analysis by 1H and 13C NMR Spectroscopy," Journal of Organic Chemistry, 57(6), 1772-1777 (1992).*
Murray et al., "Synthesis of Tetrose Nucleosides. I. Adenine Nucleosides of Erythrose and Threose," Journal of Pharmaceutical Sciences, 56(7), 1772-1777865-870 (Jul. 1967).*
Schöning et al., "Chemical Etiology of Nucleic Acids Structure: [alpha]-Threofuranosyl-(3'->2') Oligonucleotide SYstem," Science, 290, 1347-1351 (Nov. 17, 2000).*
Office Action for Japanese Patent Application No. 2007-501071, dated Apr. 3, 2012.
English language translation of Office Action for Japanese Patent Application No. 2007-501071, dated Apr. 3, 2012.
Office Action issued in Canadian Patent Application No. 2,556,829, dated Jan. 15, 2013 (2 pages).
Dujardin et al., "Asymmetric Endoselective [4+2] Heterocycloadditions of Styrene Dienophiles with Chiral Benzylidenepyruvic Esters. Total Synthesis of (-)-O-Dimethylsugiresinol," *Tetrahedron Letters*. 38: 1555-1558 (1997).
Griengl et al., "Phosphonoformate and Phosphonoacetate Derivatives of 5-Substituted 2'-Deoxyuridines: Synthesis and Antiviral Activity," *J. Med. Chem.* 31:1831-1839 (1988).
Kempeneers et al., "Recognition of Threosyl Nucleotides by DNA and RNA Polymerases," Nucleic Acids Research 31: 6221-6226 (2003).
Kim et al., "Regiospecific and Highly Stereoselective Electrophilic Addition to Furanoid Glycals: Synthesis of Phosphonate Nucleotide Analogues with Potent Activity against HIV," *J. Org. Chem* 56: 2642-2647 (1991).
Kline et al., "($^{13}$C)-Substituted Erythronucleosides: Synthesis and Conformational Analysis by $^1$H and $^{13}$C NMR Spectroscopy," *J.Org. Chem.* 57: 1772-1777 (1992).

(Continued)

*Primary Examiner* — Lawrence E Crane
(74) *Attorney, Agent, or Firm* — Clark & Elbing LLP

(57) ABSTRACT

The invention is directed to phosphonate nucleosides comprising a phosphonalkoxy-substituted five-membered, saturated or unsaturated, oxygen-containing ring coupled to a heterocyclic nucleobase such as a pyrimidine or purine base, as well as pharmaceutical compositions thereof. These compounds, which can be described by general formula (II), are useful for the treatment of retroviral infection, e.g., HIV (Human Immunodeficiency Virus) infection in a mammal. The invention also features synthetic intermediates for the preparation of phosphonate nucleosides.

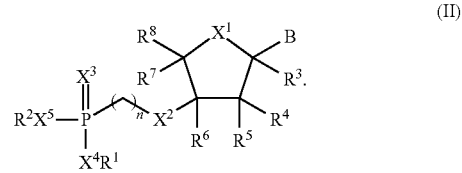

(II)

16 Claims, 16 Drawing Sheets

OTHER PUBLICATIONS

Lambert et al., "Synthesis and Antiviral Activity of Phosphonoacetic and Phosphonoformic Acid Esters of 5-Bromo-2'-deoxyuridine and Related Pyrimidine Nucleosides and Acyclonucleosides," *J. Med. Chem.* 32: 367-374 (1989).

Murray et al., "Synthesis of Tetrose Nucleosides I. Adenine Nucleosides of Erythrose and Threose," *Journal of Pharmaceutical Sciences* 56: 865-870 (1967).

McNulty et al., "On the direct 2,3-hydroxyl-Group Differentiation of Tartaric Acid Esters," *Tetrahedron Letters* 43: 3857-3861 (2002).

Schöning et al., "Chemical Etiology of Nucleic Acid Structure: The α-Threofuranosyl-(3'→2') Oligonucleotide System," *Science.* 290: 1347-1351 (2000).

Wu et al., "Deoxythreosyl Phosphonate Nucleosides as Selective Anti-HIV Agents," *J. Am. Chem. Soc.* 127: 5056-5065 (2005).

Wu et al., "Base-Pairing Systems Related to TNA: α-Threofuranosyl Oligonucleotides Containing Phosphoramidate Linkages," *Organic Letters.* 4:1279-1282 (2002).

Office Action issued in U.S. Appl. No. 10/598,535 on Dec. 3, 2009 (11 pages).

Office Action issued in U.S. Appl. No. 10/598,535 on Aug. 11, 2010 (11 pages).

Interview Summary and Advisory Action issued in U.S. Appl. No. 10/589,535 on Feb. 7, 2011 (3 pages).

Notice of Allowance and Notice of Allowability issued in U.S. Appl. No. 10/589,535 on Jul. 25, 2011 (6 pages).

Translation of Notification of Defects for Israeli Patent Application No. 177658, dated May 11, 2010.

Notification prior to Acceptance for Israeli Patent Application No. 177658, mailed Dec. 28, 2010.

English Language Translation of Notification prior to Acceptance for Israeli Patent Application No. 177658, mailed Dec. 28, 2010.

Office Action for Japanese Patent Application No. 2007-501071, dated Jun. 28, 2011.

English Language Translation of Office Action for Japanese Patent Application No. 2007-501071, dated Jun. 28, 2011.

Examiner's First Report on Australian Patent Application No. 2005219461, mailed Oct. 9, 2009.

Examiner's Report for New Zealand Patent Application No. 549236, dated May 6, 2010.

Examiner's Report for Canadian Patent Application No. 2,556,829, dated Jul. 27, 2011.

Examiner's Report for Canadian Patent Application 2,556,829, dated Apr. 17, 2012.

International Search Report issued in PCT/BE2005/000032, dated Aug. 30, 2005.

Written Opinion of the International Searching Authority issued in PCT/BE2005/000032, dated Aug. 30, 2005.

International Preliminary Report on Patentability issued in PCT/BE2005/000032, dated May 23, 2006.

\* cited by examiner

PHOSPHONATE NUCLEOSIDES USEFUL AS ACTIVE INGREDIENTS IN PHARMACEUTICAL COMPOSITIONS FOR THE TREATMENT OF VIRAL INFECTIONS, AND INTERMEDIATES FOR THEIR PRODUCTION

This application is a continuation of U.S. patent application Ser. No. 10/598,535, filed Sep. 1, 2006, now U.S. Pat. No. 8,076,310, which is the U.S. National Stage of International Application No. PCT/BE2005/000032, filed on Mar. 4, 2005, which claims the benefit under 35 U.S.C. §119(e) of U.S. Provisional Application Serial No. 60/552,730, filed Mar. 15, 2004, and further claims priority of British Patent Application No. 0404891.4, filed Mar. 4, 2004 and British Patent Application No. 0407712.9, filed Apr. 5, 2004.

FIELD OF THE INVENTION

The present invention relates to a series of novel phosphonate nucleosides and thiophosphonate nucleosides, more specifically phosphonate nucleosides and thiophosphonate nucleosides comprising a phosphonalkoxy-substituted or phosphonothioalkyl-substituted five-membered, saturated or unsaturated, oxygen-containing or sulfur-containing ring coupled to a heterocyclic nucleobase such as a pyrimidine or purine base. The invention further relates to certain phosphonate nucleosides and thiophosphonate nucleosides having antiviral activity, more specifically HIV (Human Immunodeficiency Virus) replication inhibiting properties. The invention also relates to methods for the preparation of such phosphonate nucleosides and thiophosphonate nucleosides, as well as novel intermediates useful in one or more steps of such syntheses. The invention also relates to pharmaceutical compositions comprising an effective amount of such phosphonate nucleosides and thiophosphonate nucleosides as active ingredients. This invention further relates to the use of such phosphonate nucleosides and thiophosphonate nucleosides as medicines or in the manufacture of a medicament useful for the treatment of mammals suffering from viral infections, in particular HIV infection. This invention further relates to methods for the treatment of viral infections in mammals by the administration of a therapeutical amount of such phosphonate nucleosides and thiophosphonate nucleosides, optionally combined with one or more other drugs having anti-viral activity.

BACKGROUND OF THE INVENTION

A retrovirus designated human immunodeficiency virus (HIV) is the etiological agent of the complex disease that includes progressive destruction of the immune system (acquired immune deficiency syndrome, hereinafter AIDS) and degeneration of the central and peripheral nervous system. There are two types of HIV, HIV-1 and HIV-2, the latter producing a less severe disease than the former. Being a retrovirus, its genetic material is in the form of RNA (ribonucleic acid) consisting of two single RNA strands. Coexisting with RNA are reverse transcriptase (having polymerase and ribonuclease activity), integrase, a protease and other proteins.

It is known in the art that some antiviral compounds which act as inhibitors of HIV replication are effective agents in the treatment of AIDS and similar diseases. Drugs that are known and approved for the treatment of HIV-infected patients belong to one of the following classes:

nucleoside reverse transcriptase inhibitors (NRTI) such as, but not limited to, azidothymidine, zidovudine, lamivudine, didanosine, abacavir, adefovir and the like, nucleotide reverse transcriptase inhibitors (NtRTI) such as, but not limited to, tenofovir (commercially available under the trade name Viread), non-nucleoside reverse transcriptase inhibitors such as, but not limited to, nevirapine, efavirenz and the like, protease inhibitors such as, but not limited to, nelfinavir, saquinavir, ritonavir, indinavir, amprenavir, fosamprenavir and the like, and fusion inhibitors such as enfuvirtide.

A relatively new target that was focused on lately is the integrase enzyme of HIV, while also many other proteins acting as enzymes or co-factors are being investigated.

Replication of the human immunodeficiency virus type 1 (hereinafter referred as HIV-1) can be drastically reduced in infected patients by combining potent antiviral drugs targeted at multiple viral targets, as reviewed by Vandamme et al. in *Antiviral Chem. Chemother.* (1998) 9:187-203.

Multiple-drug combination regimes can reduce viral load below the detection limit of the most sensitive tests. Nevertheless low level ongoing replication has been shown to occur, possibly in sanctuary sites, leading to the emergence of drug-resistant strains, according to Perelson et al. in *Nature* (1997) 387:123-124.

Furthermore the selectivity of many antiviral agents is rather low, possibly making them responsible for side-effects and toxicity. Moreover, HIV can develop resistance to most, if not all, currently approved antiviral drugs, according to Schmit et al. in *J. Infect. Dis.* (1996) 174:962-968. It is well documented that the ability of HIV to rapidly evolve drug resistance, together with toxicity problems resulting from known drugs, requires the development of additional classes of antiviral drugs.

As a summary, there is still a stringent need in the art for potent inhibitors of HIV. Therefore a goal of the present invention is to satisfy this urgent need by identifying efficient pharmaceutically active ingredients that are less toxic and/or more resistant to virus mutations than existing antiviral drugs and that can be useful, either alone or in combination with other active ingredients, for the treatment of retroviral infections, in particular lentiviral infections, and more particularly HIV infections, in mammals and more specifically in humans. Furthermore, another goal of the present invention is complement existing antiviral drugs in such a way that the resulting drug combination has improved activity or improved resistance to virus mutation than each of the individual compounds.

The family of the Flaviviridae consists of 3 genera, the pestiviruses, the flaviviruses and the hepaciviruses and also contains the hepatitis G virus (HGV/GBV-C) that has not yet been assigned to a genus. Pestiviruses such as the Classical Swine Fever Virus (CSFV), the Bovine Viral Diarrhea Virus (BVDV) and the Border Disease Virus (BDV) cause infections of domestic livestock (respectively pigs, cattle and sheep) and are responsible for significant economic losses world-wide. Vaccines are used in some countries with varying degrees of success to control pestivirus disease. In other countries, animal culling and slaughter are used to contain pestivirus disease outbreaks.

The World Health Organization estimates that world-wide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1 to 5% of whom may develop liver cancer during the next then years. The only treatment option available today is the use of interferon α-2 (or its pegylated from) either alone or combined with ribavirin. However, sustained response is only observed in about 40% of the patients and treatment is associated with serious adverse effects. There is thus an urgent need for potent and selective inhibitors of the replication of the HCV in order to treat infections with HCV. Furthermore, the study of specific inhibitors of HCV replication has been hampered by the fact that it is not possible to propagate HCV (efficiently) in cell culture. Since HCV and pestiviruses belong to the same virus family and share many similarities (organisation of the genome, analogous gene products and replication cycle), pestiviruses have been adopted as a model and surrogate for HCV. For example BVDV is closely related to hepatitis C virus (HCV) and used as a surrogate virus in drug development for HCV infection.

In view of their important pharmacological value, there is a need for drugs having antiviral activity against viruses belonging to the family of Flaviviridae including hepatitis C virus.

Pioneering work on the chemistry of phosphonate nucleosides has already been carried out and includes certain important reaction schemes to synthesize phosphonate nucleosides. A review of chemistry and biology of phosphorous-modified nucleotide analogues is available for instance from A. Holy in *Advances in Antiviral Drug Design* (1993) 1:179-231. Phosphonate nucleosides can be divided in two categories. A first category are real nucleoside analogues since they contain a nucleobase and a sugar moiety. A second category of phosphonate nucleosides, represented for instance by 9-(2-phosphonylmethoxyethyl)adenine (adefovir), can be considered as alkylated nucleobases since their sugar moiety is replaced by an alkoxyalkyl moiety. Surprisingly, up to now, potent antiviral in vivo activity (HSV, CMV, HBV, HIV) has only been associated with certain phosphonalkoxyalkyl nucleobases and not with sugar containing phosphonate nucleosides. Several attempts to discover antiviral nucleoside phosphonates have led to synthetic schemes for the preparation of furanose-, pyranose- and carbocyclic phosphonate nucleosides, all of them however lacking potent antiviral activity.

Phosphorylation by kinases and incorporation into nucleic acids (eventually leading to chain termination) is considered as an important mechanism which may explain the antiviral activity of nucleosides. The lack of antiviral activity of phosphonate nucleosides of the first category is generally explained by their poor substrate properties for cellular and viral kinases. On the other hand, the potent antiviral activity of phosphonylated alkylated nucleobases of the second category has been ascribed to their intracellular phosphorylation into diphosphates and to an incorporation of the modified nucleosides into nucleic acids (enzymatic incorporation into nucleic acids being almost irreversible) which has negative consequences downstream and thereby inhibits viral growth. A disadvantage of the acyclic nucleoside phosphonates are their low selectivity index in cellular screening systems. The selectivity of the triphosphates of anti-HIV nucleosides for HIV reverse transcriptase versus mitochondrial DNA polymerases is usually regarded as an important factor determining in vivo toxicity. Thus there is still a need in the art for drug candidates having suitable selectivity for HIV reverse transcriptase. A less flexible structure such as is present in the nucleosides phosphonates is considered to improve both binding to polymerases and viral-versus-host selectivity. Consequently, nucleosides phosphonates retaining their HIV reverse transcriptase affinity are considered as strong antiviral candidates.

Threose nucleosides have been previously synthesized because they can be assembled from natural precursor molecules. It has been demonstrated that threose nucleic acids (TNA) form duplexes with DNA and RNA exhibiting a thermal stability similar to that of the natural nucleic acids association. Triphosphates of threose nucleosides are accepted as substrate by several polymerases and can be enzymatically incorporated in DNA. A few 2,5-dihydro-5-(phosphonomethoxy)-2-furanyl nucleosides derived from thymine and adenine with antiretroviral activity have been disclosed by Kim et al. in *J. Org. Chem.* (1991) 56:2642-2647. EP-A-398,231 describes a family of phosphonomethoxymethoxymethyl purine/pyrimidine derivatives being effective in combating viral infections at a dose of 0.01 to 30 mg/kg bodyweight. U.S. Patent Publication No. 2004/0023921 discloses a pharmaceutical composition comprising a nucleotide analog with a phosphonate group at an amount effective to inhibit a viral polymerase of an hepatitis C virus (hereinafter referred as HCV) or to act as a substrate for the viral polymerase of the HCV virus. WO 98/20017 describes a family of modified nucleoside-5'-triphosphates which are inhibitors or substrates of DNA polymerases and antiviral agents, being in particular able to inhibit the reproduction of the human HIV virus in a culture of human lymphocytes.

Although, as is apparent from the prior art of record, numerous compounds were proposed for meeting the various above mentioned requirements in terms of retroviral therapy, it was observed that none of them does achieve such goals and, consequently, there is still a stringent need in the art for new compounds being able to solve these problems.

SUMMARY OF THE INVENTION

Without wishing to be bound by theory, the present invention is based on the unexpected finding that the above-mentioned problems can be solved by a novel class of compounds wherein the phosphonoalkoxy group or phosphonothioalkyl group of a furanose nucleoside phosphonate (or its sulfur analogue wherein furanyl is replaced with thienyl) is bound at the 3'-position, thus bringing the phosphorous atom and the nucleobase much closer to each other than in the previously known nucleoside phosphonates. This invention is also based on the unexpected finding that the absence of a hydroxymethyl substituent in the 4'-position of this class of compounds avoids steric hindrance during the enzymatic phosphorylation reaction, therefore avoiding the poor substrate properties for cellular and viral kinases (leading to poor antiviral activity) of the nucleoside phosphonates of the prior art. In addition, depending on the length of the carbon-based linking structure between the 5-membered ring and the phosphorous atom, the phosphonylated nucleosides of the invention can be considered as mono-, di- or triphosphate mimics. By varying the length of this linking structure, the present invention makes it possible to further finely tune the antiviral activity of the novel class of compounds. Also, this invention is based on the unexpected finding that the presence of an anomeric centre in this novel class of threose nucleoside phosphonates provides them with similar stereo-electronic properties to that of natural nucleosides.

Based on the above unexpected findings, the present invention provides new anti-viral agents, especially anti-retroviral agents, and more particularly anti-HIV compounds. These compounds are phosphonate nucleosides, more particularly phosphonoalkoxy-substituted and phosphonothioalkyl-substituted nucleosides comprising a five-membered, saturated or unsaturated, oxygen-containing or sulfur-containing ring (preferably dihydrofuranyl, tetrahydrofuranyl, dihydrothienyl or tetrahydrothienyl), or analogues or derivatives thereof, which have been shown that they possess anti-viral activity against various classes of viruses such as, but not limited to, retriviridae, flaviviridae and papoviridae, more specifically against the human HIV. The present invention demonstrates that these compounds efficiently inhibit the replication of HIV in mammals. Therefore, these phosphonate nucleosides constitute a useful class of new potent anti-viral compounds that can be used in the treatment and/or prevention of viral infections in animals such as mammals, and humans, more specifically for the treatment and/or prevention of HIV in humans.

The present invention also relates to compounds having antiviral activities with respect to one or more other viruses such as, but not limited to, hepatitis B virus, hepatitis C virus, papilloma virus, flaviviruses, picornaviruses and the like. The present invention furthermore relates to the use of such compounds as medicines, more specifically as anti-viral agents, and to their use for the manufacture of medicaments for treating and/or preventing viral infections, in particular retroviral infections such as, but not limited to, HIV in humans. The invention also relates to methods for the preparation of all such compounds and to pharmaceutical compositions comprising them in an anti-viral effective amount.

The present invention also relates to a method of treatment or prevention of viral infections, in particular retroviral infections such as, but not limited to, HIV in humans by the administration of one or more such compounds, optionally in combination with one or more other anti-viral agents, to a patient in need thereof.

One particularly useful aspect of the present invention is the provision of new phosphonate nucleosides comprising a phosphonoalkoxy-substituted or phosphonothioalkyl-substituted five-membered, saturated or unsaturated, ring which is coupled to a heterocyclic nucleobase, preferably a pyrimidine or a purine base. In another particularly useful embodiment of the invention, the five-membered, saturated or unsaturated, ring is an oxygen-containing ring such as dihydrofuranyl and tetrahydrofuranyl.

An embodiment of the invention relates to novel 3'-phosphonalkoxy-substituted or 3'-phosphonothioalkyl-substituted, saturated or unsaturated, furanose nucleosides comprising a purine or pyrimidine base coupled to the 1' position of a furanose, whereby the 3' position of the furanose is substituted with a phosphonoalkoxy group or a phosphonothioalkyl group. These nucleosides can also be derived from tetrahydrofuran or 3,4-dihydrofuran thereby substituted at the 2 position with a heterocyclic base such as, but not limited to, pyrimidine and purine bases, and at the 4 position with a phosphonoalkoxy group or phosphonothioalkyl group.

DEFINITIONS

Figure 1A:
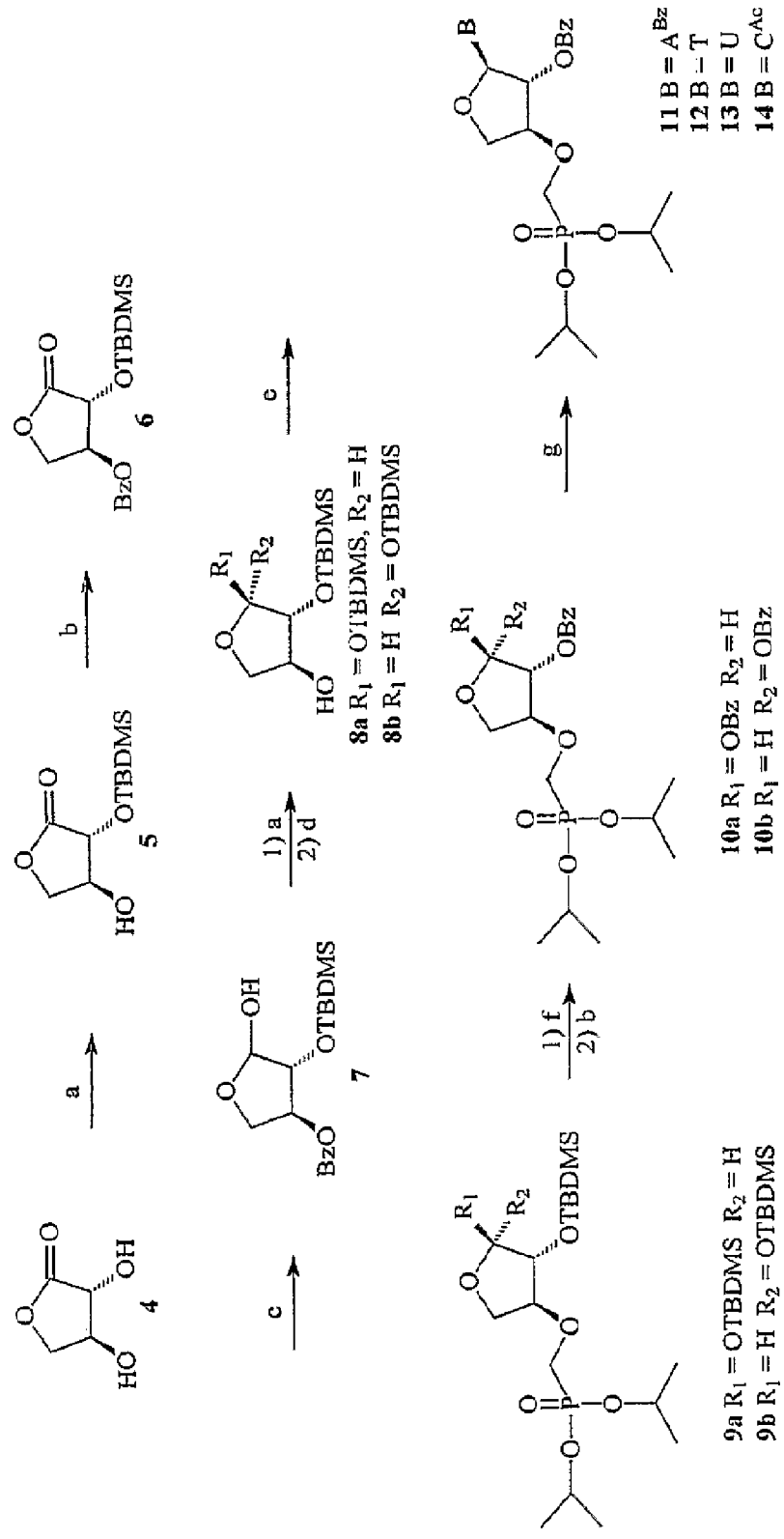
FIGS. 1 to 15 schematically show a number of alternative synthetic routes for making various embodiments of the nucleoside phosphonates of this invention, as well as intermediates involved in such synthetic routes. More specifically these synthetic routes relate to 2' substitution and, still more specifically, to a different stereochemistry at the 1' and 3' positions of the molecule. Abbreviations used in the figures are defined in the specification herein after. In particular, "Nu" stands for a nucleophile.

As used herein, and unless stated otherwise, the term "furanose" refers to five-membered cyclic monosaccharides and, by extension, to their sulfur analogues. The numbering of monosaccharides starts at the carbon next to the oxygen inclosed in the ring and is indicated with a prime (').

As used herein, and unless stated otherwise, the term "phosphonalkoxy" refers to a phosphonate coupled via an alkyl group (such as defined herein after) to an oxygen atom which itself can be coupled to another molecule or group.

As used herein, and unless stated otherwise, the term "phosphono-thioalkyl" refers to a phosphonate coupled via an alkyl group (such as defined herein after) to a sulfur atom which itself can be coupled to another molecule or group.

As used herein, and unless stated otherwise, the term "3'-phosphonoalkoxy furanose nucleoside" refers to a heterocyclic base, such as a purine or pyrimidine base, coupled to the 1' position of a furanose whereby the 3' position of said furanose is substituted with a phosphonoalkoxy group.

As used herein, and unless stated otherwise, the terms "heterocyclic nucleobase" and "pyrimidine and purine bases" include, but are not limited to, adenine, thymine, cytosine, uracyl, guanine and (2,6-)diaminopurine such as may be found in naturally-occurring nucleosides. The term also includes analogues and derivatives thereof. An analogue thereof is a base which mimics such naturally-occurring bases in such a way that its structure (the kinds of atoms present and their arrangement) is similar to the above-listed naturally-occurring bases but is modified by either having additional functional properties with respect to the naturally-occurring bases or lacking certain functional properties of the naturally-occurring bases. Such analogues include, but are not limited to, those derived by replacement of a —CH— moiety by a nitrogen atom (e.g. 5-azapyrimidines such as 5-azacytosine) or vice-versa (e.g. 7-deazapurines, such as 7-deaza-adenine or 7-deazaguanine) or both (e.g. 7-deaza, 8-azapurines). A derivative of naturally-occurring bases, or analogues thereof, is a compound wherein the heterocyclic ring of such bases is substituted with one or more conventional substituents independently selected from the group consisting of halogen, hydroxyl, amino and $C_{1-6}$ alkyl. Some additional illustrative examples are provided in the specification herein after. Such purine or pyrimidine bases, analogues and derivatives thereof, are well known to those skilled in the art, e.g. from documents such as, but not limited to, WO 03/093290 and WO 04/028481.

As used herein, and unless stated otherwise, the term "alkyl" as used herein refers to linear or branched saturated hydrocarbon chains having from 1 to 18 carbon atoms such as, but not limited to, methyl, ethyl, 1-propyl, 2-propyl, 1-butyl, 2-methyl-1-propyl (isopropyl), 2-butyl (sec-butyl), 2-methyl-2-propyl (tert-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and the like; preferably the alkyl group has from 1 to 8 carbon atoms, more preferably from 1 to 4 carbon atoms.

As used herein, and unless stated otherwise, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

As used herein, and unless stated otherwise, the terms "alkenyl" and "cycloalkenyl" refer to linear or branched hydrocarbon chains having from 2 to 18 carbon atoms, respectively cyclic hydrocarbon chains having from 3 to 10 carbon atoms, with at least one ethylenic unsaturation (i.e. a carbon-carbon sp2 double bond) which may be in the cis or trans configuration such as, but not limited to, vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

As used herein, and unless stated otherwise, the terms "alkynyl" and "cycloalkynyl" refer to linear or branched hydrocarbon chains having from 2 to 18 carbon atoms, respectively cyclic hydrocarbon chains having from 3 to 10 carbon atoms, with at least one acetylenic unsaturation (i.e. a carbon-carbon sp triple bond) such as, but are not limited to, ethynyl (—C≡CH), propargyl (—CH$_2$C≡CH), cyclopropynyl, cyclobutynyl, cyclopentynyl, or cyclohexynyl.

As used herein with respect to a substituting radical, and unless otherwise stated, the term "aryl" designates any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-C$_{4-8}$ cycloalkyl radicals (the latter being as defined above) such as, for instance, indanyl, tetrahydronaphtyl, fluorenyl and the like, all of the said radicals being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

As used herein with respect to a substituting group, and unless otherwise stated, the terms "arylalkyl", "arylalkenyl" and "heterocyclic-substituted alkyl" refer to an aliphatic saturated or ethylenically unsaturated hydrocarbon monovalent group (preferably a C$_{1-18}$ alkyl or C$_{2-18}$ alkenyl such as defined above) onto which an aryl or heterocyclic group (such as defined herein) is already bonded, and wherein the said aliphatic group and/or the said aryl or heterocyclic group may be optionally substituted with one or more substituents independently selected from the group consisting of halogen, amino, hydroxyl, sulfhydryl, C$_{1-7}$ alkyl, trifluoromethyl and nitro, such as but not limited to benzyl, 4-chlorobenzyl, 4-fluorobenzyl, 2-fluorobenzyl, 3,4-dichlorobenzyl, 2,6-dichlorobenzyl, 3-methylbenzyl, 4-methylbenzyl, 4-ter-butylbenzyl, phenylpropyl, 1-naphthyl methyl, phenylethyl, 1-amino-2-phenylethyl, 1-amino-2-[4-hydroxy-phenyl]ethyl, 1-amino-2-[indol-2-yl]ethyl, styryl, pyridylmethyl (including all isomers thereof), pyridylethyl, 2-(2-pyridyl)isopropyl, oxazolylbutyl, 2-thienylmethyl, pyrrolylethyl, morpholinylethyl, imidazol-1-yl-ethyl, benzodioxolylmethyl and 2-furylmethyl.

As used herein with respect to a substituting group, and unless otherwise stated, the term "heterocyclic ring" or "heterocyclic" means a mono- or polycyclic, saturated or mono-unsaturated or polyunsaturated monovalent hydrocarbon group having from 3 up to 15 carbon atoms and including one or more heteroatoms in one or more heterocyclic rings, each of said rings having from 3 to 10 atoms (and optionally further including one or more heteroatoms attached to one or more carbon atoms of said ring, for instance in the form of a carbonyl or thiocarbonyl or selenocarbonyl group, and/or to one or more heteroatoms of said ring, for instance in the form of a sulfone, sulfoxide, N-oxide, phosphate, phosphonate or selenium oxide group), each of said heteroatoms being independently selected from the group consisting of nitrogen, oxygen; sulfur, selenium and phosphorus, also including radicals wherein a heterocyclic ring is fused to one or more aromatic hydrocarbon rings for instance in the form of benzo-fused, dibenzo-fused and naphto-fused heterocyclic radicals; within this definition are included heterocyclic groups such as, but not limited to, pyridyl, dihydropyridyl, tetrahydropyridyl (piperidyl), thiazolyl, tetrahydrothienyl, tetrahydrothienyl sulfoxide, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetra hydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl; heterocyclic groups may be sub-divided into heteroaromatic (or "heteroaryl") groups such as, but not limited to, pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl, and non-aromatic heterocyclic groups; when a heteroatom of the said non-aromatic heterocyclic group is nitrogen, the latter may be substituted with a substituent selected from the group consisting of alkyl, cycloalkyl, aryl, arylalkyl and alkylaryl (such as defined herein); by way of example, carbon-bonded heterocyclic rings may be bonded at position 2, 3, 4, 5, or 6 of a pyridine, at position 3, 4, 5, or 6 of a pyridazine, at position 2, 4, 5, or 6 of a pyrimidine, at position 2, 3, 5, or 6 of a pyrazine, at position 2, 3, 4, or 5 of a furan, tetrahydrofuran, thiofuran, thiophene, pyrrole or tetrahydropyrrole, at position 2, 4, or 5 of an oxazole, imidazole or thiazole, at position 3, 4, or 5 of an isoxazole, pyrazole, or isothiazole, at position 2 or 3 of an aziridine, at position 2, 3, or 4 of an azetidine, at position 2, 3, 4, 5, 6, 7, or 8 of a quinoline or at position 1, 3, 4, 5, 6, 7, or 8 of an isoquinoline; still more specific carbon-bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl; by way of example, nitrogen-bonded heterocyclic rings may be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, at position 2 of an isoindole or isoindoline, at position 4 of a morpholine, and at position 9 of a carbazole or β-carboline, still more specific nitrogen-bonded heterocycles include 1-aziridyl, 1-azetedyl, 1-pyrrolyl, 1-imidazolyl, 1-pyrazolyl and 1-piperidinyl.

The term "acyl" as used herein, unless otherwise stated, refers to a carbonyl group directly attached to an alkyl, alkenyl, alkynyl, aryl, heterocyclic, arylalkyl, arylalkenyl, arylalkynyl, heterocyclic-alkyl, heterocyclic-alkenyl or heterocyclic-alkynyl group, such as for example alkanoyl (alkylcarbonyl), aroyl (arylcarbonyl), arylalkanoyl or alkylaroyl group, wherein the carbonyl group is coupled to another molecule. As an example, the term "acyloxyalkyl"

refers to an acyl group coupled via an oxygen atom to an alkyl group, the latter being further coupled to another molecule or atom.

As an example, "alkylalkenylcarbonate" refers to a alkyl-OC(O)O-alkenyl group, thus a carbonate substituted at one side with an alkyl and on the other side with an alkenyl, one of the alkyl and alkenyl groups being further coupled to another molecule or atom.

As used herein and unless otherwise stated, the terms "alkoxy", "cyclo-alkoxy", "aryloxy", "arylalkyloxy", "oxyheterocyclic", "thioalkyl", "thio cycloalkyl", "arylthio", "arylalkylthio" and "thioheterocyclic" refer to substituents wherein an alkyl group, respectively a cycloalkyl, aryl, arylalkyl or heterocyclic group (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like.

As used herein and unless otherwise stated, the term halogen means any atom selected from the group consisting of fluorine, chlorine, bromine and iodine.

As used herein with respect to a substituting radical, and unless otherwise stated, the term "amino-acid" refers to a radical derived from a molecule having the chemical formula H$_2$N—CHR—COOH, wherein R is the side group of atoms characterizing the amino-acid type; said molecule may be one of the 20 naturally-occurring amino-acids or any similar non naturally-occurring amino-acid.

As used herein and unless otherwise stated, the term "stereoisomer" refers to all possible different isomeric as well as conformational forms which the compounds of the invention may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

As used herein and unless otherwise stated, the term "solvate" includes any combination which may be formed by a compound of this invention with a suitable inorganic solvent (e.g. hydrates) or organic solvent, such as but not limited to alcohols, ketones, esters and the like.

The term "pharmaceutically acceptable carrier or excipient" as used herein refers to any material or substance with which the active principle, i.e. a compound of this invention may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid.

As used herein and unless otherwise stated, the term "tetrose" refers to any of a class of monosaccharides containing four carbon atoms such as, but not limited to, erythrose or threose with the general formula C$_4$H$_8$O$_4$. Tetrose compounds (carbohydrate nomenclature) can alternatively be named as tetrahydrofuranyl compounds (IUPAC nomenclature) since they share the five-membered oxygen-containing heterocycle.

As used herein and unless otherwise stated, the term "anomeric carbon" refers to the carbon atom containing the carbonyl functionality of a sugar molecule, also referred to as a carbohydrate. This carbon atom is involved in the hemiacetal or hemiketal formation characteristic for the sugar ring structure. This carbonyl carbon is referred to as the anomeric carbon because it is non-chiral in the linear structure, and chiral in the cyclic structure.

As used herein and unless otherwise stated, the term "selective protection" and "selective deprotection" refers to the introduction, respectively the removal, of a protecting group on a specific reactive functionality in a molecule containing several functionalities, respectively containing several protected functionalities, and leaving the rest of the molecule unchanged. Many molecules used in the present invention contain more than one reactive functionality. For example carbohydrates are characterised by more than one alcohol functional group. It is often necessary to manipulate only one (or some) of these groups at a time without interfering with the other functionalities. This is only possible by choosing a variety of protecting groups, which can be manipulated using different reaction conditions. The use of protecting groups in such a way that it is possible to modify a functionality independently from the other functionalities present in the molecule is referred to as "orthogonal protection". The development of orthogonal protecting group strategies makes it possible to remove one set of protecting groups in any order with reagents and conditions, which do not affect the groups in other sets. An efficient protecting group strategy can be critical for accomplishing the synthesis of large, complex molecules possessing a diverse range of reactive functionality. This protection reaction can be chemoselective when selectivity is due to chemical properties, regioselective when due to the location of the functionality within the molecule. A reaction or transformation can be "stereoselective" in two ways, i.e. (1) because it will only occur at a specific stereoisomer or at a specific stereo-orientation of the functionality, or (2) because it will result in only one specific stereoisomer. A protection reaction can therefore also be stereoselective for example in a way that it will only result in protection of a functionality when in a certain conformation.

As used herein and unless otherwise stated, the snake-like symbol stands for a bond with specific stereo-orientation but for which both options are possible, i.e. for any stereochemical arrangement of said bond.

DETAILED DESCRIPTION OF THE INVENTION

One embodiment of the present invention relates to novel compounds being 3'-phosphonate substituted furanose nucleosides represented by the general formula (I):

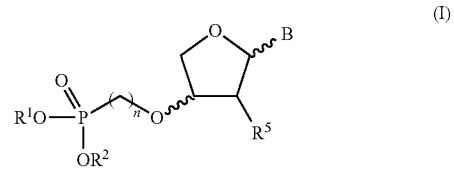

wherein:
B is a heterocycle selected from the group consisting of pyrimidine and purine bases;
the snake-like symbol means any stereochemical arrangement of the bond linking B, or the phosphonalkoxy group, to the furanyl group.
$R^1$ and $R^2$ are each independently selected from the group consisting of hydrogen; (—PO$_3$R$^{16}$)$_m$—PO$_3$R$^{17}$R$^{18}$; alkyl; alkenyl; alkynyl; cycloalkyl; cycloalkenyl; cycloalkynyl; aryl; arylalkyl; heterocyclic ring; heterocyclic ring-alkyl; acyloxyalkyl; acyloxyalkenyl; acyloxyalkynyl; acyloxyaryl; acyloxyarylalkyl; acyloxyarylalkenyl; acyloxyarylalkynyl; dialkylcarbonate; alkylarylcarbonate; alkylalkenylcarbonate; alkylalkynylcarbonate; alkenylarylcarbonate; alkynylarylcarbonate; alkenylalkynylcarbonate; dialkenylcarbonate; dialkynyl-carbonate; wherein said alkyl, alkenyl and alkynyl can contain a heteroatom in or at the end of the hydrocarbon chain, said heteroatom being selected from the group consisting of oxygen, sulfur and nitrogen; and $R^1$ and $R^2$ are further selected from substituents known for phosphonates described as anti-viral agents;

$R^5$ is selected from hydrogen, azido, halogen (preferably) fluoro, cyano, alkyl, alkenyl, alkynyl, $SR^{14}$ and $OR^{14}$;

$R^{14}$ is selected from hydrogen; alkyl; alkenyl; alkynyl; cycloalkyl; cycloalkenyl; cycloalkynyl; aryl; heterocyclic ring; arylalkyl; heterocyclic ring-alkyl; acyloxyalkyl; wherein said alkyl, alkenyl and alkynyl can contain a heteroatom in or at the end of the hydrocarbon chain, said heteroatom being selected from the group consisting of oxygen, sulfur and nitrogen;

$R^{16}$, $R^{17}$ and $R^{18}$ are independently selected from the group consisting of hydrogen; alkyl; alkenyl; alkynyl; cycloalkyl; cycloalkenyl; cycloalkynyl; aryl; arylalkyl; heterocyclic ring; heterocyclic ring-alkyl; acyloxyalkyl; wherein said alkyl, alkenyl and alkynyl can contain a heteroatom in or at the end of the hydrocarbon chain, said heteroatom being selected from the group consisting of oxygen, sulfur and nitrogen;

n is an integer selected from 1, 2, 3, 4, 5 or 6;

m is 0 or 1, including pharmaceutically acceptable salts, solvates, and isomers thereof.

In one embodiment, the invention relates to compounds according to the general formula (I), wherein B is selected from adenine and thymine. In another particular embodiment, the 3'-phosphonalkoxy substituent or the purine or pyrimidine base (i.e. the heterocycle B) coupled to the ring of the compounds according to the general formula (I) are in the R or S configuration.

In its more general acceptance, the invention relates to a first class of compounds including a heterocyclic nucleobase attached to a first carbon atom of an optionally substituted five-member saturated heterocyclic group selected from tetrahydrofuranyl and tetrahydrothienyl and further including a phosphonoalkoxy, thiophosphonoalkoxy, phosphonothioalkyl or thiophosphonothioalkyl group attached to a second carbon atom of said five-member saturated heterocyclic group, said first carbon atom being adjacent to the heteroatom of said five-member saturated heterocyclic group, and said second carbon atom being adjacent neither to the heteroatom nor to the first carbon atom of said five-member saturated heterocyclic group. This first class of compounds may be represented by the general formula (II):

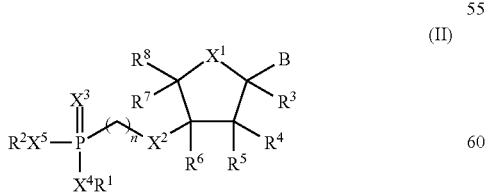

(II)

wherein:

$X^1$, $X^2$, $X^3$, $X^4$ and $X^5$ are each independently selected from the group consisting of oxygen and sulfur, B is a natural or non-natural heterocyclic nucleobase, $R^1$ and $R^2$ are each independently selected from the group consisting of hydrogen; $(-PO_3R^{16})_m$—$PO_3R^{17}R^{18}$; alkyl; alkenyl; alkynyl; cycloalkyl; cycloalkenyl; cycloalkynyl; aryl; arylalkyl; heterocyclic; heterocyclic-alkyl; acyloxyalkyl; acyloxyalkenyl; acyloxyalkynyl; acyloxyaryl; acyloxyarylalkyl; acyloxyarylalkenyl; acyloxyarylalkynyl; dialkylcarbonate; alkylarylcarbonate; alkylalkenylcarbonate; alkylalkynylcarbonate; alkenylarylcarbonate; alkynylarylcarbonate; alkenylalkynylcarbonate; dialkenylcarbonate; dialkynylcarbonate; wherein said alkyl, alkenyl and alkynyl optionally contains one or more heteroatoms in or at the end of the hydrocarbon chain, said heteroatoms being independently selected from the group consisting of oxygen, sulfur and nitrogen;

$R^3$, $R^4$, $R^5$, $R^6$, $R^7$ and $R^8$ are each independently selected from the group consisting of hydrogen, azido, halogen (preferably fluoro), cyano, alkyl, alkenyl, alkynyl, $SR^{14}$ and $OR^{14}$;

$R^{14}$ is selected from hydrogen; alkyl; alkenyl; alkynyl; cycloalkyl; cycloalkenyl; cycloalkynyl; aryl; heterocyclic; arylalkyl; heterocyclic-alkyl; acyloxyalkyl; wherein said alkyl, alkenyl and alkynyl optionally contain one or more heteroatoms in or at the end of the hydrocarbon chain, said heteroatoms being independently selected from the group consisting of oxygen, sulfur and nitrogen;

$R^{16}$, $R^{17}$ and $R^{18}$ are independently selected from the group consisting of hydrogen; alkyl; alkenyl; alkynyl; cycloalkyl; cycloalkenyl; cycloalkynyl; aryl; arylalkyl; heterocyclic; heterocyclic-alkyl; acyloxyalkyl; wherein said alkyl, alkenyl and alkynyl optionally contain one or more heteroatoms in or at the end of the hydrocarbon chain, said heteroatoms being independently selected from the group consisting of oxygen, sulfur and nitrogen;

$X^4$ and $R^1$, or $X^5$ and $R^2$ may together form an amino-acid residue or polypeptide wherein a carboxyl function of said amino-acid residue being at a distance from the amidate nitrogen not further than 5 atoms is esterified;

$X^4$ and $R^1$ or $X^5$ and $R^2$ may together form a group having the formula —$OC(R^9)_2OC(O)Y(R^{10})_a$ wherein Y=N or O, a=1 when Y is O and a=1 or 2 when Y is N;

$R^9$ is selected from the group consisting of hydrogen, alkyl, aryl, alkenyl, alkynyl, alkenylaryl, alkynylaryl or alkylaryl, wherein each of said alkyl, alkenyl, alkynyl and aryl groups is optionally substituted with one or more atoms or groups selected from the group consisting of halo, cyano, azido, nitro and $OR^{14}$;

$R^{10}$ is selected from the group consisting of hydrogen, alkyl, aryl, alkenyl, alkynyl, alkenylaryl, alkynylaryl and alkylaryl, wherein each of said alkyl, alkenyl, alkynyl and aryl groups is optionally substituted with one or more atoms or groups selected from the group consisting of halo, cyano, azido, nitro, $OR^{14}$ and $NR^{11}R^{12}$;

$R^{11}$ and $R^{12}$ are each independently selected from the group consisting of hydrogen and alkyl;

n is an integer representing the number of methylene groups between and P, each of said methylene groups being optionally and independently substituted with one or two substituents selected from the group consisting of halogen, hydroxyl, sulhydryl and $C_{1-4}$ alkyl, and n being selected from 1, 2, 3, 4, 5 and 6; and m is 0 or 1, including pharmaceutically acceptable salts, solvates, isomers and prodrugs thereof.

More specific embodiments of the invention include subclasses of stereoisomers represented by any of the following formulae (III) to (XVIII):

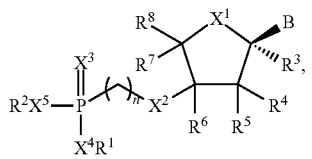
(III)

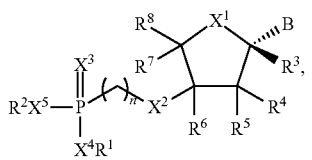
(IV)

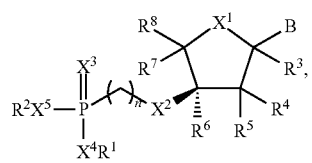
(V)

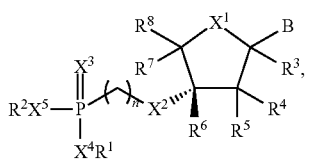
(VI)

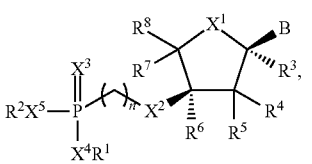
(VII)

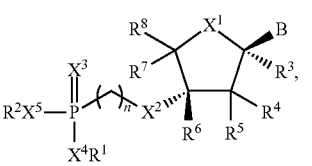
(VIII)

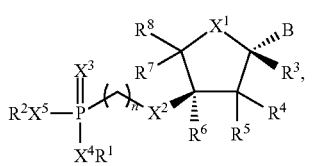
(IX)

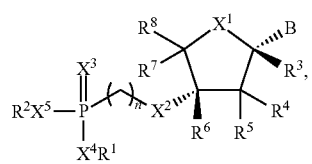
(X)

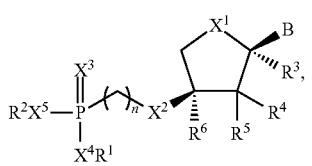
(XI)

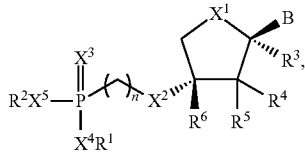
(XII)

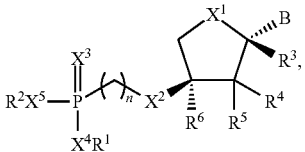
(XIII)

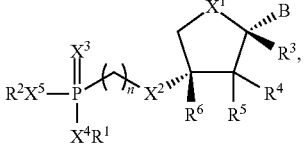
(XIV)

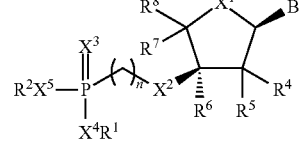
(XV)

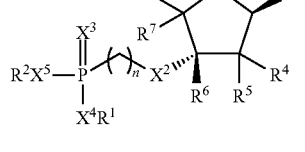
(XVI)

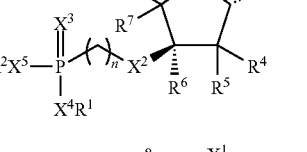
(XVII)

(XVIII)

wherein n, m, B, $X^1$, $X^2$, $X^3$, $X^4$, $X^5$, $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{16}$, $R^{17}$ and $R^{18}$ are defined as in formula (II), including pharmaceutically acceptable salts, solvates, isomers and prodrugs thereof.

In a specific embodiment, this invention relates to compounds represented by any of the formulae (II) to (XVIII), wherein $R^4$ is hydroxy.

In a preferred embodiment, this invention relates to compounds represented by any of the formulae (II) to (XVIII), wherein at least one of $R^7$ and $R^8$ is hydrogen, more preferably both $R^7$ and $R^8$ are hydrogen.

In its more general acceptance, the invention also relates to a second class of compounds including a heterocyclic nucleobase attached to a first carbon atom of an optionally substituted five-member mono-unsaturated heterocyclic group selected from dihydrofuranyl and dihydrothienyl and further including a phosphonoalkoxy, thiophosphonoalkoxy, phosphonothioalkyl or thiophosphonothioalkyl group attached to a second carbon atom of said five-member mono-unsaturated heterocyclic group, said first carbon atom being adjacent to the heteroatom of said five-member mono-unsaturated heterocyclic group, and said second carbon atom being adjacent neither to the heteroatom nor to the first carbon atom of said five-member mono-unsaturated heterocyclic group. This second class of compounds may be represented by the general formula (XIX):

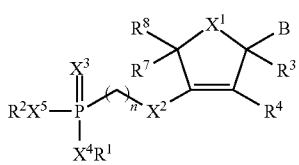

(XIX)

wherein:
- $X^1$, $X^2$, $X^3$, $X^4$ and $X^5$ are each independently selected from the group consisting of oxygen and sulfur,
- B is a natural or non-natural heterocyclic nucleobase,
- $R^1$ and $R^2$ are each independently selected from the group consisting of hydrogen; $(-PO_3R^{16})_m-PO_3R^{17}R^{18}$; alkyl; alkenyl; alkynyl; cycloalkyl; cycloalkenyl; cycloalkynyl; aryl; arylalkyl; heterocyclic; heterocyclic-alkyl; acyloxyalkyl; acyloxyalkenyl; acyloxyalkynyl; acyloxyaryl; acyloxyarylalkyl; acyloxyarylalkenyl; acyloxyarylalkynyl; dialkylcarbonate; alkylarylcarbonate; alkylalkenylcarbonate; alkylalkynylcarbonate; alkenylarylcarbonate; alkynylarylcarbonate; alkenylalkynylcarbonate; dialkenylcarbonate; dialkynylcarbonate; wherein said alkyl, alkenyl and alkynyl optionally contain one or more heteroatoms in or at the end of the hydrocarbon chain, said heteroatoms being independently selected from the group consisting of oxygen, sulfur and nitrogen;
- $R^3$, $R^4$, $R^7$ and $R^8$ are each independently selected from the group consisting of hydrogen, azido, halogen (preferably fluoro), cyano, alkyl, alkenyl, alkynyl, $SR^{14}$ and $OR^{14}$;
- $R^{14}$ is selected from hydrogen; alkyl; alkenyl; alkynyl; cycloalkyl; cycloalkenyl; cycloalkynyl; aryl; heterocyclic; arylalkyl; heterocyclic-alkyl; acyloxyalkyl; wherein said alkyl, alkenyl and alkynyl optionally contain one or more heteroatoms in or at the end of the hydrocarbon chain, said heteroatoms being independently selected from the group consisting of oxygen, sulfur and nitrogen;
- $R^{16}$, $R^{17}$ and $R^{18}$ are independently selected from the group consisting of hydrogen; alkyl; alkenyl; alkynyl; cycloalkyl; cycloalkenyl; cycloalkynyl; aryl; arylalkyl; heterocyclic ring; heterocyclic ring-alkyl; acyloxyalkyl; wherein said alkyl, alkenyl and alkynyl optionally contain one or more heteroatoms in or at the end of the hydrocarbon chain, said heteroatoms being independently selected from the group consisting of oxygen, sulfur and nitrogen;
- $X^4$ and $R^1$, or $X^5$ and $R^2$ may together form an amino-acid residue or polypeptide wherein a carboxyl function of said amino-acid residue being at a distance from the amidate nitrogen not further than 5 atoms is esterified;
- $X^4$ and $R^1$ or $X^5$ and $R^2$ may together form a group having the formula $-OC(R^9)_2OC(O)Y(R^{10})_a$ wherein Y=N or O, a=1 when Y is O and a=1 or 2 when Y is N;
- $R^9$ is selected from the group consisting of hydrogen, alkyl, aryl, alkenyl, alkynyl, alkenylaryl, alkynylaryl or alkylaryl, wherein each of said alkyl, alkenyl, alkynyl and aryl groups is optionally substituted with one or more atoms or groups selected from the group consisting of halo, cyano, azido, nitro and $OR^{14}$;
- $R^{10}$ is selected from the group consisting of hydrogen, alkyl, aryl, alkenyl, alkynyl, alkenylaryl, alkynylaryl and alkylaryl, wherein each of said alkyl, alkenyl, alkynyl and aryl groups is optionally substituted with one or more atoms or groups selected from the group consisting of halo, cyano, azido, nitro, $OR^{14}$ and $NR^{11}R^{12}$;
- $R^{11}$ and $R^{12}$ are each independently selected from the group consisting of hydrogen and alkyl;
- n is an integer representing the number of methylene groups between and P, each of said methylene groups being optionally and independently substituted with one or two substituents selected from the group consisting of halogen, hydroxyl, sulfhydryl and $C_{1-4}$ alkyl, and n being selected from 1, 2, 3, 4, 5 and 6; and
- m is 0 or 1, including pharmaceutically acceptable salts, solvates, isomers and prodrugs thereof.

More specific embodiments of the invention include subclasses of compounds being stereoisomers represented by any of the following formulae (XX) to (XXVI):

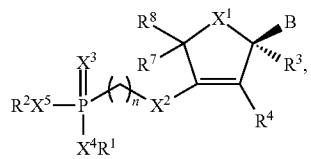

(XX)

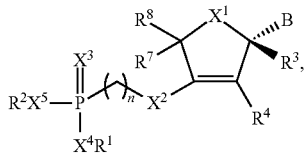

(XXI)

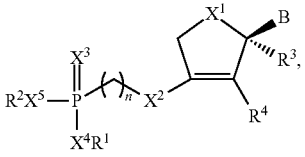

(XXII)

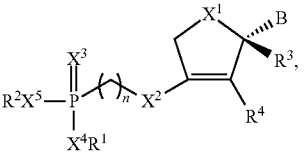

(XXIII)

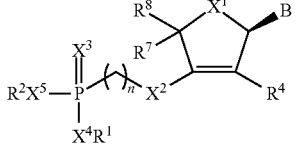

(XXIV)

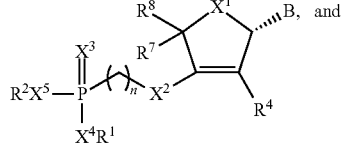

(XXV)

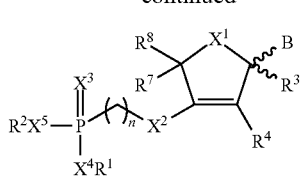

(XXVI)

wherein n, m, B, $X^1$, $X^2$, $X^3$, $X^4$, $X^5$, $R^1$, $R^2$, $R^3$, $R^4$, $R^7$, $R^8$, $R^9$, $R^{10}$, $R^{11}$, $R^{12}$, $R^{14}$, $R^{16}$, $R^{17}$ and $R^{18}$ are defined as in formula (XIX), and wherein the snake-like symbol stands for any stereochemical arrangement of the respective bond, including pharmaceutically acceptable salts, solvates, isomers and prodrugs thereof.

In a specific embodiment, this invention relates to compounds represented by any of the formulae (XIX) to (XXVI), wherein $R^4$ is hydroxy.

In a preferred embodiment, this invention relates to compounds represented by any of the formulae (XIX) to (XXVI), wherein at least one of $R^7$ and $R^8$ is hydrogen, more preferably wherein both $R^7$ and $R^8$ are hydrogen.

It should be understood that in the above embodiments of the invention, the novel compounds are as defined in any of the general formulae (I) to (XXVI), wherein:

each of the substituents B, $X^1$, $X^2$, $X^3$, $X^4$, $X^5$, $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{16}$, $R^{17}$ and $R^{18}$ may independently correspond to any of the definitions given above, in particular with any of the preferred ranges or individual meanings (such as illustrated above) of generic terms used for substituting radicals such as, but not limited to, "alkyl", "cycloalkyl", "alkenyl", "alkynyl", "aryl", "heterocyclic", "halogen", "cycloalkenyl", "alkylaryl", "arylalkyl", "alkoxy", "cycloalkoxy", "thioalkyl", "thiocycloalkyl", "aminoacid" and the like, each of the integers m and n may independently correspond to any of the individual values given above.

In each of the formulae (I) to (XXVI), the alkylene chain between $X^2$ and the phosphorus atom P is preferably a short chain, i.e. n is preferably 1 or 2. This alkylene chain may also include one or more substituents such as halogen, hydroxyl, sulhydryl and methyl, for instance it may be any of —CYY'—, —CHY—, —CYY'—CY"Y'"— or —CHY—CY'Y"—, each of Y, Y', Y" and Y'" being preferably independently selected from the group consisting of fluoro, chloro, hydroxyl, sulhydryl and methyl.

It should be understood that $R^1$ and $R^2$ refers to the definitions of phosphonate prodrugs such as described for example in U.S. Pat. Nos. 6,225,460 and 5,977,089.

Specific embodiments of bases B suitable for inclusion into the compounds of the present invention include, but are not limited to, hypoxanthine, guanine, adenine, cytosine, inosine, thymine, uracil, xanthine, 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 1-deaza derivatives of 2-aminopurine, 2,6-diaminopurine, 2-amino-6-chloropurine, hypoxanthine, inosine and xanthine; 7-deaza derivatives of 2-aminopurine, 2,6-diaminopurine, 2-amino-6-chloropurine, hypoxanthine, inosine and xanthine; 3-deaza derivatives of 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-meth-ylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil and 5-propynyluracil. Preferably, B is a 9-purinyl residue selected from guanyl, 3-deazaguanyl, 1-deazaguanyl, 8-azaguanyl, 7-deazaguanyl, adenyl, 3-deazaadenyl, 1-dezazadenyl, 8-azadenyl, 7-deazaadenyl, 2,6-diaminopurinyl, 2-aminopurinyl, 6-chloro-2-aminopurinyl and 6-thio-2-aminopurinyl.

A particular embodiment of the present invention provides the phosphonate substituted nucleosides having any of the formulae (I) to (XXVI) wherein B is selected from adenine and thymine. Another particular embodiment of the present invention provides novel 3'-phosphonate substituted threose nucleosides, more particularly 3'-phosphonalkoxy substituted threose nucleosides. In another particular embodiment of the present invention, the 3'-phosphonalkoxy substituent or the purine or pyrimidine bases coupled to the ring of the compounds of the invention are in the R or S configuration.

The present invention also relates to certain novel intermediates that are made and used during the course of manufacturing one or more of the phosphonate substituted nucleosides having any of the formulae (I) to (XXVI). Such novel intermediates may be represented by the following general formulae (XXVII) to (XXXVI):

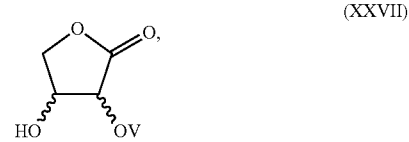
(XXVII)

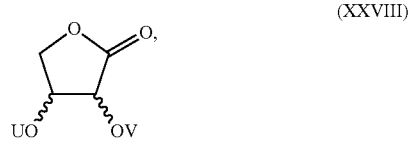
(XXVIII)

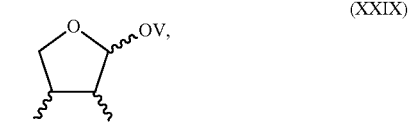
(XXIX)

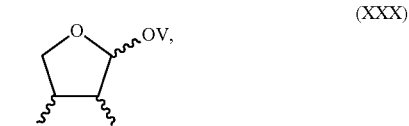
(XXX)

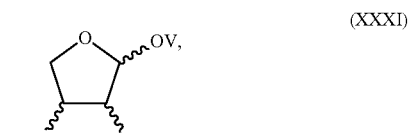
(XXXI)

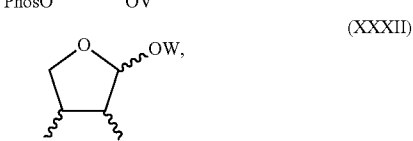
(XXXII)

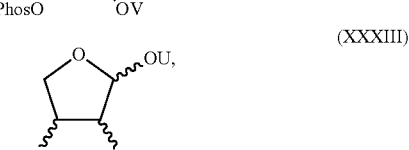
(XXXIII)

-continued

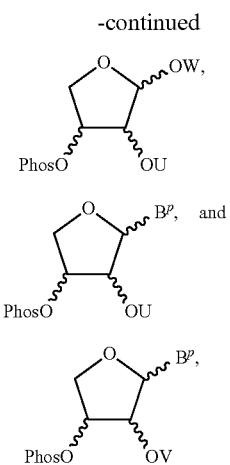

(XXXIV)

(XXXV)

(XXXVI)

wherein:
U is an acyl group,
V is a silyl group,
W is an alkyl group,
$B^p$ is an optionally protected heterocyclic nucleobase, wherein the protecting group may be acyl, silyl or benzyl ether, and
Phos is an O-protected phosphonoalkoxy or thiophosphonoalkoxy group or an S-protected phosphonothioalkyl or thiophosphonothioalkyl group, wherein the protecting group is one suitable for the protection of hydroxyl groups of a phosphonic or thiophosphonic acid.

The present invention relates in a particular embodiment to novel compounds and intermediates selected from the group consisting of:

1-($N^6$-benzoyladenin-9-yl)-2-O-benzoyl-3-O-(diisopropylphosphonomethyl)-L-threose (11),
1-(thymin-1-yl)-2-O-benzoyl-3-O-(diisopropylphosphonomethyl)-L-threose (12),
1-(uracil-1-yl)-2-O-benzoyl-3-O-(diisopropylphosphonomethyl)-L-threose (13),
1-($N^4$-acetylcytosin-1-yl)-2-O-benzoyl-3-O-(diisopropylphosphonomethyl)-L-threose (14),
1-(adenin-9-yl)-3-O-(diisopropylphosphonomethyl)-L-threose, also named (2R,3R,4S)—$N^9$-[tetrahydro-3-hydroxy-4-(di-O-isopropylphosphonomethoxy)-furanyl]adenine (15),
1-(thymin-1-yl)-3-O-(diisopropylphosphonomethyl)-L-threose, also named (2R,3R,4S)—$N^1$-[tetrahydro-3-hydroxy-4-(di-O-isopropylphosphonomethoxy)-furanyl]thymine (16),
1-(uracil-1-yl)-3-O-(diisopropylphosphonomethyl)-L-threose, also named (2R,3R,4S)—$N^1$-[tetrahydro-3-hydroxy-4-(di-O-isopropylphosphonomethoxy)-furanyl]uracile (17),
1-(cytosin-1-yl)-3-O-(diisopropylphosphonomethyl)-L-threose, also named (2R,3R,4S)—$N^1$-[tetrahydro-3-hydroxy-4-(di-O-isopropylphosphonomethoxy)furanyl]cytosine (18),
1-(adenin-9-yl)-2-deoxy-3-O-(diisopropylphosphonomethyl)-L-threose, also named (2R,4R)—$N^9$-[tetrahydro-4-(di-O-isopropylphosphonomethoxy)-furanyl]adenine (19),
1-(thymin-1-yl)-2-deoxy-3-O-(diisopropylphosphonomethyl)-L-threose, also named (2R,4R)—$N^1$-[tetrahydro-4-(di-O-isopropylphosphonomethoxy)-furanyl]thymine (20),
1-(uracil-1-yl)-2-deoxy-3-O-(diisopropylphosphonomethyl)-L-threose, also named (2R,4R)—$N^1$-[tetrahydro-4-(di-O-isopropylphosphonomethoxy)-furanyl]uracile (21),
1-(cytosin-1-yl)-2-deoxy-3-O-(diisopropylphosphonomethyl)-L-threose, also named (2R,4R)—$N^1$-[tetrahydro-4-(di-O-isopropylphosphonomethoxy)-furanyl]cytosine (22),
1-(adenin-9-yl)-3-O-(phosphonomethyl)-L-threose sodium salt, also named (2R,3R,4S)—$N^9$-[tetrahydro-3-hydroxy-4-(phosphonomethoxy)-furanyl]adenine sodium salt (3a),
1-(thymin-1-yl)-3-O-(phosphonomethyl)-L-threose sodium salt, also named (2R,3R,4S)—$N^9$-[tetrahydro-3-hydroxy-4-(phosphonomethoxy)-furanyl]thymine sodium salt (3b),
1-(uracil-1-yl)-3-O-(phosphonomethyl)-L-threose sodium salt, also named (2R,3R,4S)—$N^9$-[tetrahydro-3-hydroxy-4-(phosphonomethoxy)-furanyl]uracile sodium salt (3c),
1-(cytosin-1-yl)-3-O-(phosphonomethyl)-L-threose sodium salt, also named (2R,3R,4S)—$N^9$-[tetrahydro-3-hydroxy-4-(phosphonomethoxy)-furanyl]cytosine sodium salt (3d),
1-(adenin-1-yl)-2-deoxy-3-O-(phosphonomethyl)-L-threose sodium salt, also named (2R,4R)—$N^9$-[tetrahydro-4-(phosphonomethoxy)-furanyl]adenine sodium salt (3e),
1-(thymin-1-yl)-2-deoxy-3-O-(phosphonomethyl)-L-threose sodium salt, also named (2R,4R)—$N^9$-[tetrahydro-4-(phosphonomethoxy)-furanyl]thymine sodium salt (3f),
1-(uracil-1-yl)-2-deoxy-3-O-(phosphonomethyl)-L-threose sodium salt, also named (2R,4R)—$N^9$-[tetrahydro-4-(phosphonomethoxy)-furanyl]uracile sodium salt (3g),
1-(cytidin-1-yl)-2-deoxy-3-O-(phosphonomethyl)-L-threose sodium salt, also named (2R,4R)—$N^9$-[tetrahydro-4-(phosphonomethoxy)-furanyl]cytosine sodium salt (3h),
(3R,4S)-tetrahydro-4-hydroxy-3-O-tertbutyldimethylsilyl-furan-2-one,
(3R,4S)-tetrahydro-4-O-benzoyl-3-O-tertbutyldimethylsilyl-furan-2-one,
(2R/S,3R,4S)-tetrahydro-4-O-benzoyl-2-O-methyl-3-O-tertbutyldimethylsilyl-furan-2-one,
(2S,3R,4S)-tetrahydro-2,3-di-O-tertbutyldimethylsilyl-4-hydroxy-furane,
(2R,3R,4S)-tetrahydro-2,3-di-O-tertbutyldimethylsilyl-4-hydroxy-furane,
(2S,3R,4S)-tetrahydro-2,3-di-O-tertbutyldimethylsilyl-4-(di-O-isopropylphosphonomethoxy)-furane,
(2R,3R,4S)-tetrahydro-2,3-di-O-tertbutyldimethylsilyl-4-(di-O-isopropylphosphonomethoxy)-furane,
(2S,3R,4S)-tetrahydro-2,3-di-O-benzoyl-4-(di-O-isopropyl phosphonomethoxy)furane,
(2R,3R,4S)-tetrahydro-2,3-di-O-benzoyl-4-(di-O-isopropylphosphonomethoxy)furane,
(2R,3R,4S)—$N^6$-benzoyl-$N^9$-[tetrahydro-3-O-benzoyl-4-(di-O-isopropylphosphonomethoxy)-furanyl]adenine,
(2R,3R,4S)—$N^1$-[tetrahydro-3-O-benzoyl-4-(d i-O-isopropyl phosphonomethoxy)furanyl]thymine,
(2R,3R,4S)—$N^1$-[tetrahydro-3-O-benzoyl-4-(di-O-isopropylphosphonomethoxy)furanyl]uracile, and
(2R,3R,4S)—$N^6$-acetyl-$N^1$-[Tetrahydro-3-O-benzoyl-4-(di-O-isopropylphosphonomethoxy)-furanyl]cytosine.

According to a second aspect, the invention relates to the use of phosphonate substituted nucleosides of the formulae (I) to (XXXVI) as antiviral compounds, more particularly as compounds active against HIV. The invention also relates to the use of phosphonate substituted nucleosides of the formulae (I) to (XXXVI) for the manufacture of a medicine or as a pharmaceutically active ingredient, especially as a virus replication inhibitor, preferably a retrovirus replication inhibitor, for instance for the manufacture of a medicament or pharmaceutical composition having antiviral activity for the prevention and/or treatment of viral, preferably retroviral, infections in humans and mammals. The present invention further relates to a method of treatment of a viral infection, preferably a retroviral infection in a mammal, including a human, comprising administering to the mammal in need of such treatment a therapeutically effective amount of a compound of any of formulae (I) to (XXXVI) as an active ingredient, preferably in admixture with at least a pharmaceutically acceptable carrier.

The invention further relates to methods for the preparation of compounds of formulae (I) to (XXXVI). The process for preparing the phosphonoalkoxy substituted nucleosides of the present invention comprises the steps of selectively protecting the hydroxy functions present on the five-membered ring that can not react in the following step, reacting the remaining free hydroxy of the protected five-membered ring with protected phosphonylalkyl, followed by reaction with a pyrimidine or purine base, deprotection of the five-membered ring protecting groups and possible purine or pyrimidine base protecting groups, if necessary a deoxygenation step of the hydroxy funstions present on the five-membered ring and finally a deprotection of the phosphonate protecting groups.

The invention also relates to pharmaceutical compositions comprising a compound of the invention according to any of the previous formulae (I) to (XXXVI) as an active ingredient in admixture with at least a pharmaceutically acceptable carrier, the active ingredient being in a concentration of at least about 0.1%, preferably at least 1%, more preferably at least 3%, most preferably at least 5%, by weight of the composition. Preferably the active ingredient is in a concentration of at most about 50%, more preferably at most 30%, most preferably at most 20% by weight of the composition.

The invention further relates to a pharmaceutical composition comprising:
(a) one or more compounds having any of the general formulae (I) to (XXXVI), and
(b) one or more other anti-viral agents, preferably one or more retroviral enzyme inhibitors
as biologically active agents, in admixture with at least a pharmaceutically acceptable carrier, (a) and (b) preferably being in respective proportions such as to provide a synergistic effect against a viral infection (preferably a lentiviral infection and more preferably a retroviral infection) in a mammal. This composition for instance may be in the form of a combined preparation for simultaneous or sequential use in viral, preferably retroviral, infection therapy.

Within the framework of this embodiment of the invention, the retroviral enzyme inhibitors that may be used as therapeutically active ingredients (b) for co-administration include, among others, the following:
    HIV-1 integrase inhibitors such as reviewed for instance in WO 02/051419,
    reverse transcriptase inhibitors such as, but not limited to, delavirdine, dideoxyadenosine, foscarnet sodium, stavudine, suramin sodium, zalcitabine and the like,
    nucleoside reverse transcriptase inhibitors such as, but not limited to, for instance azidothymidine, zidovudine, lamivudine, didanosine, abacavir, adefovir and the like,
    nucleotide reverse transcriptase inhibitors such as, but not limited to, for instance tenofovir,
    non-nucleoside reverse transcriptase inhibitors such as, but not limited to, nevirapine, efavirenz and the like,
    HIV-1 protease inhibitors such as, but not limited to, saquinavir, ritonavir, indinavir, nelfinavir, amprenavir, fosamprenavir and the like, and
    HIV fusion inhibitors such as enfuvirtide, and inhibitors of HIV membrane fusion such as described in U.S. Pat. Nos. 6,818,710 and 6,841,657.

Other suitable antiviral agents for inclusion into the above antiviral compositions or combined preparations include for instance acyclovir, cidofovir, cytarabine, edoxudine, famciclovir, floxuridine, ganciclovir, idoxuridine, penciclovir, sorivudine, trifluridine, valaciclovir, vidarabine, kethoxal, methisazone, moroxydine, podophyllotoxin, ribavirine, rimantadine, stallimycine, statolon, tromantadine and xenazoic acid.

The invention also relates to compounds according to any of the general formulae (I) to (XXXVI) being used for inhibiting the proliferation of other viruses than HIV, preferably hepatitis B virus, hepatitis C virus, human papilloma virus or flaviviruses, in particular yellow fever virus or Dengue virus.

More generally, the invention relates to the compounds of formulae (I) to (XXXVI) being useful as agents having biological activity (preferably antiviral or antitumoral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Another aspect of the invention relates to a pharmaceutical composition comprising a phosphonalkoxy-substituted or phosphonothioalkyl-substituted nucleoside of the invention according to any of formulae (I) to (XXXVI), more in particular having antiviral activity, yet more in particular against HIV.

A further aspect of the invention provides for a method of treatment or prevention of a viral infection in a mammal, comprising administering to the mammal in need of such treatment a therapeutically effective amount of a phosphonalkoxy-substituted or phosphonothioalkyl-substituted nucleoside according to any of formulae (I) to (XXXVI).

The compounds of the invention optionally are bound covalently to an insoluble matrix and used for affinity chromatography (separations, depending on the nature of the groups of the compounds, for example compounds with aryl are useful in hydrophobic affinity separations.

The compounds of the invention are employed for the treatment or prophylaxis of viral infections, more particularly HIV infections. When using one or more compounds according to any of the formulae (I) to (XXXVI) as defined herein:
    the active ingredients of the compound(s) may be administered to the mammal (including a human) to be treated by any means well known in the art, i.e. orally, intranasally, subcutaneously, intramuscularly, intradermally, intravenously, intra-arterially, parenterally or by catheterization.
    the therapeutically effective amount of the preparation of the compound(s), especially for the treatment of viral infections in humans and other mammals, preferably is a retroviral enzyme inhibiting amount. More preferably, it is a retroviral replication inhibiting amount or a retroviral enzyme inhibiting amount of the compounds of formulae (I) to (XXXVI) as defined herein. Depending upon the pathologic condition to be treated and the patient's condition, the said effective amount may be divided into several sub-units per day or may be administered at more than one day intervals.

The present invention further relates to a method for preventing or treating a viral infections in a subject or patient by administering to the patient in need thereof a therapeutically effective amount of phosphonate nucleosides of the present invention.

The therapeutically effective amount of the preparation of the compound(s), especially for the treatment of viral infections in humans and other mammals, preferably is HIV protein/enzyme inhibiting amount. More preferably, it is a HIV replication inhibiting amount or a HIV enzyme inhibiting amount of the derivative(s) of the formulas as defined herein. Depending upon the pathologic condition to be treated and the patient's condition, the effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as subsynergistic, and when it is lower than 0.5, the combination is defined as synergistic. When the minimum FIC index is between 1.0 and 2.0, the combination is defined as subantagonistic and, when it is higher than 2.0, the combination is defined as antagonistic.

This principle may be applied to a combination of different antiviral drugs of the invention or to a combination of the antiviral drugs of the invention with other drugs that exhibit anti-HIV activity.

The invention thus relates to a pharmaceutical composition or combined preparation having synergistic effects against a viral infection and containing:
(a) a combination of two or more of the phosphonate nucleosides of the present invention, and
(b) optionally one or more pharmaceutical excipients or pharmaceutically acceptable carriers,
for simultaneous, separate or sequential use in the treatment or prevention of a viral infection, or
(c) one or more anti-viral agents, and
(d) at least one of the phosphonate nucleosides of the present invention, and
(e) optionally one or more pharmaceutical excipients or pharmaceutically acceptable carriers,
for simultaneous, separate or sequential use in the treatment or prevention of a viral infection.

Suitable anti-viral agents for inclusion into the synergistic antiviral compositions or combined preparations of this invention include practically all known anti-HIV compounds known at this moment such as nucleoside and non-nucleoside reverse transcriptase inhibitors, protease inhibitors and integrase inhibitors.

The pharmaceutical composition or combined preparation with synergistic activity against viral infection according to this invention may contain the phosphonate nucleosides of the present invention, compounds according to any of the formulae (I) to (XXXVI), over a broad content range depending on the contemplated use and the expected effect of the preparation.

According to a particular embodiment of the invention, the compounds of the invention may be employed in combination with other therapeutic agents for the treatment or prophylaxis of HIV infections. The invention therefore relates to the use of a composition comprising:
(a) one or more compounds represented by any of formulae (I) to (XXXVI), and
(b) one or more HIV/protein-enzyme inhibitors as biologically active agents in respective proportions such as to provide a synergistic effect against a viral infection, particularly a HIV infection in a mammal, for instance in the form of a combined preparation for simultaneous, separate or sequential use in viral infection therapy, such as HIV.

When using a combined preparation of (a) and (b):
the active ingredients (a) and (b) may be administered to the mammal (including a human) to be treated by any means well known in the art, i.e. orally, intranasally, subcutaneously, intramuscularly, intradermally, intravenously, intra-arterially, parenterally or by catheterization.
the therapeutically effective amount of the combined preparation of (a) and (b), especially for the treatment of viral infections in humans and other mammals, particularly is a HIV enzyme inhibiting amount. More particularly, it is a HIV replication inhibiting amount of derivative (a) and a HIV enzyme inhibiting amount of inhibitor (b). Still more particularly when the said HIV enzyme inhibitor (b) is a reverse transcriptase inhibitor, its effective amount is a reverse transcriptase inhibiting amount. When the said HIV enzyme inhibitor (b) is a protease inhibitor, its effective amount is a protease inhibiting amount.
ingredients (a) and (b) may be administered simultaneously but it is also beneficial to administer them separately or sequentially, for instance within a relatively short period of time (e.g. within about 24 hours) in order to achieve their functional fusion in the body to be treated.

The invention also relates to the compounds of the invention, compounds according to any of the formulae (I) to (XXXVI) which can be screened for inhibition of the proliferation of other viruses than HIV, particularly for the inhibition of other retroviruses and lentiviruses and also for the inhibition of flaviviruses or picornaviruses such as BVDV, HCV, HBV or Coxsackie virus, with in particular yellow fever virus, Dengue virus, hepatitis B virus, hepatitis G virus, Classical Swine Fever virus or the Border Disease Virus. Als other viruses may be inhibited such as HSV, CMV and Sars-virus.

The present invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

More generally, the invention relates to the compounds according to any of the formulae (I) to (XXXVI) being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state, any and all protonated forms of the compounds are intended to fall within the scope of the invention.

The term "pharmaceutically acceptable salts" as used herein means the therapeutically active non-toxic salt forms which the compounds according to the formulas of the application like (I), (II), (III) are able to form. Therefore, the compounds of this invention optionally comprise salts of the compounds herein, especially pharmaceutically acceptable non-toxic salts containing, for example, $Na^+$, $Li^+$, $K^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds according to the formulas of the application like (I), (II), (III) as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or an alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

The term "isomers" as used herein means all possible isomeric forms, including tautomeric and sterochemical forms, which the compounds according to formulae (I) to (XXXVI) may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds according to the above formulae have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds" (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional, crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched compounds of the invention. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (e.g. see WO96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds according to the above formulae (I) to (XXXVI) may easily be determined by those skilled in the art while using well-known methods such as, for example, X-ray diffraction or NMR.

The compounds of the invention may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

The pharmaceutical compositions of this invention can suitably be prepared and used in the form of concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by inicronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphosphatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxy-polyethoxyethanol, polyethyleneglycol and octylphenoxy-polyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw", 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s). When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

The present invention also provides synthetic methods and processes for making compounds according to the general formulae (I) to (XXVI), as detailed herein after. The processes described further are only meant as examples and by no means are meant to limit the scope of the present invention. For a better understanding of the following description, reference is made to FIGS. 1 to 15.

The synthetic schemes in FIGS. 1 to 15 illustrate syntheses of the 3'-O-phosphonate-tetrose and 3'-S-phosphonate-tetrose nucleoside derivatives of five naturally-occurring nucleobases (adenine, thymine, uracil, cytosine, guanine) starting from commercially available lactone compounds, but these syntheses can be adapted to any heterocyclic nucleobase without inventive effort. Each figure will now be described in details.

Figure 1B:
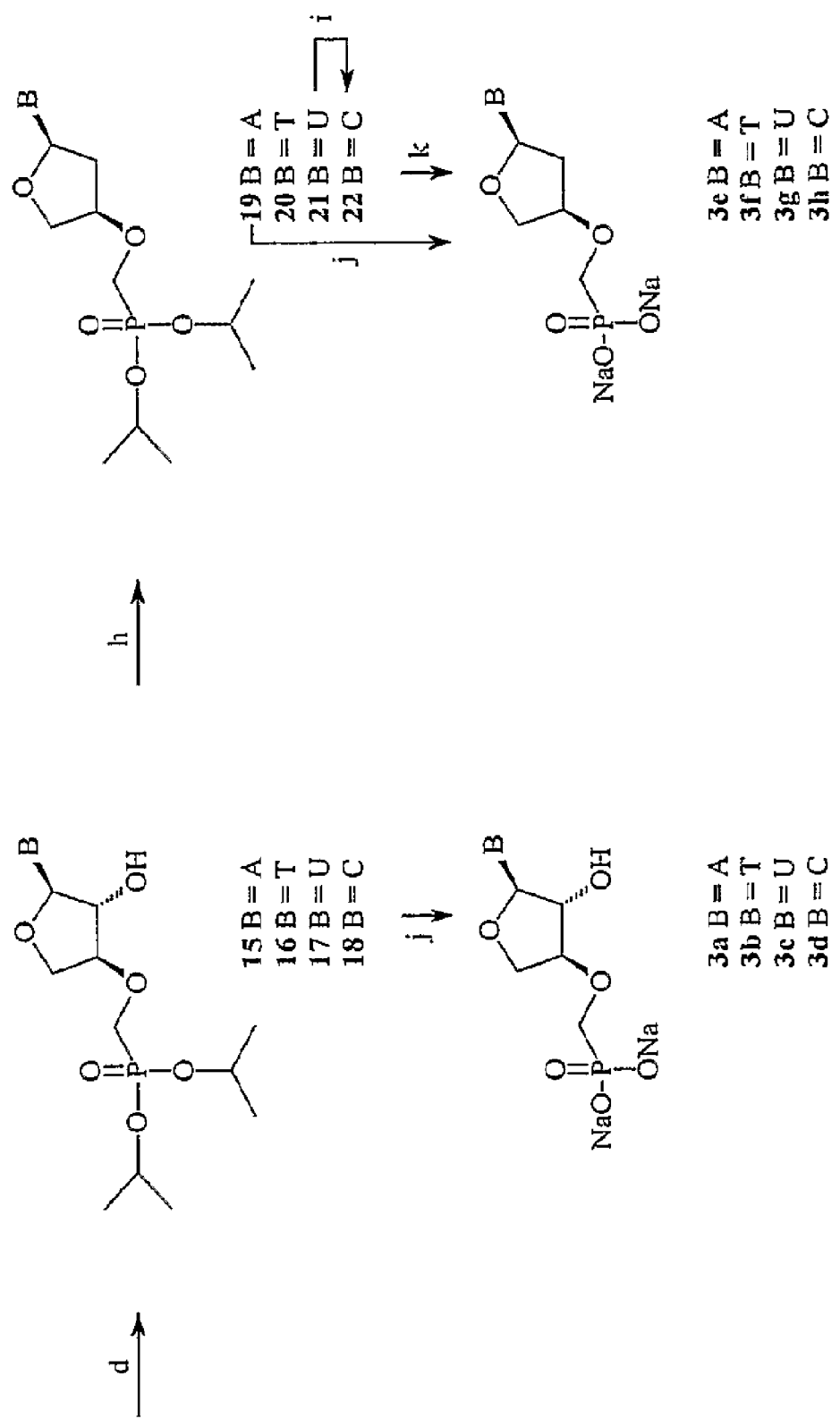

FIGS. 1A and 1B

The synthetic scheme as shown in FIGS. 1A and 1B comprises 11 steps for the synthesis of the 3'-O-phosphonate and 3'-O-phosphonate, 2'-deoxy-tetrose nucleoside derivatives of 4 naturally-occurring nucleobases (adenine, thymine, uracil, cytosine) starting from (R,S)-2,3-dihydroxy-dihydro-furan-1-one (4).

In the first step (a), the 2'-hydroxy group is selectively protected. The hydroxyl group in position 2 is selectively protected, preferably by silylation, more specifically with a tert-butyl dimethylsilyl (hereinafter referred to as TBDMS) group using TBDMS-chloride (hereinafter referred to as TBDMSCl) in the presence of a reactant, preferably imidazole, in an organic solvent, for example acetonitrile (hereinafter referred to as ACN). Protection of the hydroxy group on this position does not affect the stereochemical orientation at the carbon atom that same position. Preferably, silyl-protection is carried out starting at 0° C. up to room temperature.

In the second step of the synthesis, the free hydroxyl group on position 3 is then independantly protected, preferably by a base-labile protecting group for example by acylation, preferably by benzoylation. The benzoyl group is introduced using benzoylchloride under basic conditions in an organic solvent, for example in pyridine. Derivatisation of the hydroxy group on this position does not affect the stereochemical orientation at the carbon atom that same position. Preferably, acylation (here benzoylation) is carried out starting at 0° C. up to room temperature.

In the third step the lactone is reduced to a hemiketal. This reduction is effected using a hydride based reduction agent for example using diisobutylaluminium-hydride (hereinafter referred to as Dibal-H), preferably in a solvent such as tetrahydrofuran (hereinafter referred to as THF) or toluene. Through this reaction an anomeric centre is created. This reduction is carried out below 0° C., preferably below $-60°$ C., for example at $-78°$ C.

The fourth step involves two subsequent reactions whereby first the anomeric hydroxyl group is protected prior to deprotection of the hydroxy group on position 3. The anomeric hydroxy group is preferably protected with the same protecting group as the hydroxy group on position 2. For example also with a TBDMS group using TBDMSCl in the presence of a reactant, preferably imidazole, in an organic solvent, for example ACN. The base-labile protecting group on position 3 is removed under the appropriate conditions. For example the O-benzoyl group is removed with saturated ammonia in methanol. Upon protection of the anomeric hydroxy group, two stereoisomers are formed at that position, alpha and beta. The resulting mixture does not need to be separated because the stereo-orientation of the anomeric centre at this stage in the line of synthesis does not affect the stereochemistry of the final compounds. Deprotection of the hydroxy group on position 3 does not affect the stereochemistry of the carbon atom at that same position.

In the next step, step five in scheme 1, the hydroxy group on position 3 is phosphonoalkylated using the appropriately protected phosphonoalkyl reagent. For example, a phosphonate function is introduced using the triflate of diisopropylphosphonomethyl alcohol and NaH in THF. Derivatisation of the hydroxy group on this position does not affect the stereochemical orientation at the carbon atom of that position. Preferably, this phosphonylation reaction is carried out starting at $-78°$ C. up to room temperature.

The sixth step of the synthesis in scheme 1 consists of replacing the protection groups on the anomeric centre and on position 2 by a different one comprising first, a deprotection step and second, a protection step with the alternative protecting group. In a working example an acyl group replaces the silyl protecting group. Preferably, the TBDMS groups are removed by treatment with acid, preferably an aqueous acid solution, for example trifluoroacetic acid (hereinafter referred to as TFA) in water. Subsequent acylation is done analogous to the procedure described for step 2 of this synthetic pathway. Preferably the di-benzoyl ester is formed.

In the next step, the nucleobase is introduced on position 1 of the thus appropriately protected phosphonylated tetrose derivative. The nucleobases that are optionally N-acyl-protected (uracil, thymine, $N^6$-benzoyladenine, $N^4$-acetylcytosine) are first silylated, preferably with TMS using hexamethyldisilane (hereinafter referred to as HMDS) in the presence of ammoniumsulphate. Using a Lewis acid catalyst, preferably $SnCl_4$, the nucleobase is coupled with the tetrose moiety. The presence of a 2-O-acyl group, preferably the 2-O-benzoyl group, allows stereoselective introduction in the presence of a Lewis acid of the base moiety onto the anomeric centre. Using this method, the nucleobase is introduced at the side opposite to the hydroxy substituent on position 2. Preferably, nucleobase introduction is carried out starting at 0° C. up to room temperature.

The eighth step of the synthetic scheme is characterized by the deprotection of hydroxy on position 2 and (in case of N-acyl protected nucleobases as possibly adenine and cytosine) deprotection of the nucleobase. The 2-O-acyl group and nucleobase protecting benzoyl or acetyl groups are removed in basic conditions. For example, removal of these acyl protecting groups is done with saturated ammonia in methanol (yielding compounds 15-18).

In order to obtain the 3'-O-phosphonate tetrose derivatives, the final step now is removal of the phosphonate protecting groups by hydrolysis. For example, hydrolysis of the preferable diisopropyl protecting groups is achieved successfully by treatment with a trimethylsilyl-halogenide (hereinafter referred to as TMSX) (giving 3a-d). Preferably these compounds are treated with TMS-bromide (TMSBr) at room temperature in an organic solvent such as dichloromethane.

In order to obtain the 2'-deoxygenated analogues (3'-O-phosphonate, 2'-deoxy tetrose derivatives) the 2'-OH group of 15-17 is removed. In case of the adenine, thymine and uracil derivatives, this is achieved by a mild method involving derivatisation of the hydroxy group into a thionocarbonate or dithiocarbonate prior to radical reduction, giving 19-21. An appropriate reaction process is known as Barton deoxygenation where for example the compound is first added to a solution of phenyl(chloro)thiocarbonate in ACN in the presence of a catalytic amount of dimethylaminopyridine (hereinafter referred to as DMAP). Preferably, this first reaction of the barton deoxygenation is carried out starting at room temperature. The resulting compound is then treated with tributyltinhydride and 2,2'-Azobisisobutyronitrile (hereinafter referred to as AIBN) in a dry organic solvent for example dry toluene and allowed to react under reflux. Preferably, this second reaction of the barton deoxygenation is carried out at reflux temperature of the solvent used.

The 2'-deoxygenated cytosine derivative is obtained from the 2'-deoxygenated uracil derivative. Hereto, the oxygen on position 4 of the pyrimidine base is activated by treatment with a mixture of 1,2,4-triazole and phosphorus oxychloride in pyridine and subsequently displaced by nitrogen due to treatment with ammonia gas.

The final step in the synthesis of these 3'-O-phosphonate, 2'-deoxy-tetrose derivatives is the removal of the phosphonate protection groups by hydrolysis. For example, hydrolysis of the preferable diisopropyl protecting groups is achieved successfully by treatment with a TMSX. Preferably, the adenine derivative is treated with TMSBr and the thymine, uracil and cytosine derivatives are preferably treated with TMS-iodine (hereinafter referred to as TMSI).

All the resulting compounds of this synthetic pathway are purified using one or a combination of several methods known to the person skilled in the art such as chromatographic methods on conventional silica gel and/or ion-exchange columns and/or macroscopic synthetic beads from a dextran polymer.

FIG. 2

Figure 2:
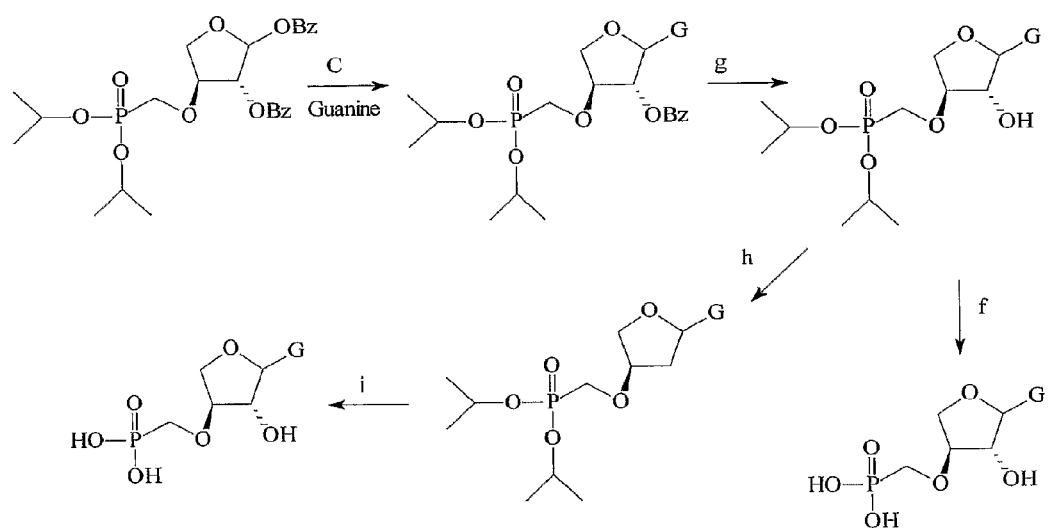

The synthetic pathway shown in scheme on FIG. 2 illustrates the synthesis of the 3'-O-phosphonate and 3'-O-phosphonate, 2'-deoxy-tetrose guanosine derivatives starting from (R,R)-2,3-dihydroxy-dihydro-furan-1-one.

The phosphonylated and protected tetrose starting material of this pathway is obtained following the steps 1-5 of the synthetic pathway given in FIG. 1.

From there on, similar to the pathway in FIG. 1, the guanosine base is introduced onto the sugar on position 1 optionally after silylation for example with HMDS together with ammoniumsulphate. Using a Lewis acid catalyst, preferably $SnCl_4$, the nucleobase is coupled with the tetrose moiety. The presence of a 2-O-acyl group, preferably the 2-O-benzoyl group, allows stereoselective introduction in the presence of a Lewis acid of the base moiety onto the anomeric centre. Using this method, the nucleobase is introduced at the side opposite to the hydroxy substituent on position 2

Subsequent deprotection of the hydroxy group on position two is achieved in the same way as step 8 of the scheme in FIG. 1.

The final step in order to obtain the 3'-O-phosphonate tetrose guanosine derivative is phosphonate deprotection achieved by hydrolysis. For example, hydrolysis of the preferable diisopropyl protecting groups is achieved successfully by treatment with a TMSX, more specifically with TMSBr at room temperature in an organic solvent such as dichloromethane.

In order to obtain the 2'-deoxygenated analogues (3'-O-phosphonate, 2'-deoxy tetrose derivatives) the 2'-OH group is removed in a similar way as for the deoxy compounds of in FIG. 1: by a mild method involving derivatisation of the hydroxy group into a thionocarbonate or dithiocarbonate prior to radical reduction, preferably using the reaction process that is known as Barton deoxygenation.

The final step in the synthesis of the 3'-O-phosphonate, 2'-deoxy guanosine tetrose derivatives is the removal of the phosphonate protection groups by hydrolysis. Hydrolysis of the preferable diisopropyl protecting groups is achieved successfully by treatment with TMSI.

The resulting compounds of this synthetic pathway are purified using one or a combination of several methods known to the person skilled in the art such as chromatographic methods on conventional silica gel, reversed phase silica gel and/or ion-exchange columns and/or macroscopic synthetic beads from a dextran polymer.

FIG. 3

Figure 3:
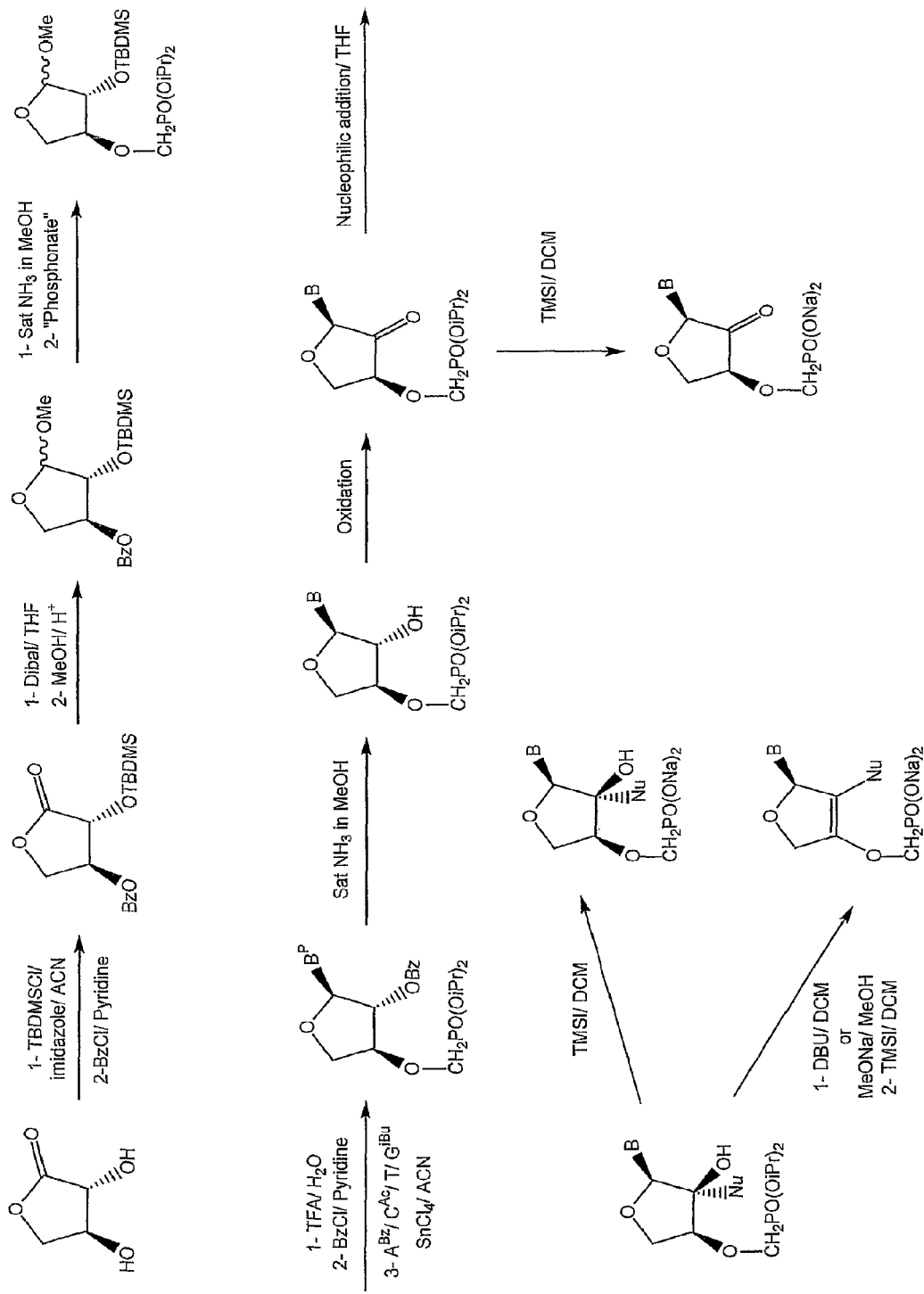

The reaction scheme given in FIG. 3 comprises 10 steps and illustrates the synthesis of 3'-O-phosphonate and tetrose derivatives with different substituents on position 2, starting from (R,S)-2,3-dihydroxy-dihydro-furan-1-one.

The first step of the synthesis comprises two reactions that are identical to the two first steps of the pathway represented by FIG. 1. The second step of the synthesis also comprises two reactions of which the first one is identical to step 3 in the pathway of FIG. 1. In the subsequent reaction, the anomeric hydroxy group is protected, for example with an alkyl group, for example methyl, by acid catalysed transacetalisation (for example in methanol when the methyl hemiketal is envisaged) or using methyl iodide/silver oxide in a polar solvent such as DMF or ACN.

The next step comprises deprotection on position 3 followed by phosphonylation on position 3. These reactions have been described in detail for the pathway represented by FIG. 1. Deprotection on position 3 embraces the removal of the base-labile protecting group. For example, the O-benzoyl group is removed with saturated ammonia in methanol. Subsequently, the phosphonoalkoxy group is introduced on position 3 following the same procedures as described for step 5 in the pathway of FIG. 1.

In the fourth step, three subsequent reactions lead to the coupling of the tetrose with the nucleobase. All three reaction-procedures are known from the pathway in FIG. 1, namely the reaction comprised by step 6 and 7 of the pathway in FIG. 1. Albeit that the intermediary products (before introduction of the nucleobase) differ with those in FIG. 1 at the level of derivatisation on position 1. However, the resulting products correspond to compounds 11-14 of FIG. 1.

Hence, the first 4 steps of this synthesis pathway can be considered as another new orthogonal protection strategy in the synthesis of 3'-phosphonylated tetrose nucleosides.

In the next step, the acyl protection group on position 2 is removed by a method as described for removal of the same type of protecting group in step 4 in FIG. 1.

Following the deprotection of the 2'-OH, an oxidation takes place at this same position in the step 6. The oxidation on position 2 is achieved using one of the many reagents known to the person skilled in the art to oxidize the 2' or 3'-hydroxy group of a nucleoside, for instance chromic acid/acetic anhydride under acidic conditions or a Dess-Martin reagent or treatment with dimethylsulfoxide (hereinafter referred to as DMSO) in combination with dicyclohexylcarbodiimide (hereinafter referred to as DCC) under acidic conditions is used.

A novel class of 3'-O-phosphonylated tetrose nucleosides is obtained when removing the phosphonyl protecting groups as described for phosphonyl deprotection in the pathway of FIG. 1.

Alternatively, the oxidation product of step 6, is used for the synthesis of other derivatives by first introducing a second substituent on position 2 by nucleophilic addition. For the nucleophilic addition reaction, reagent and reaction conditions are chosen appropriate for the desired substituent. For example, the methyl group is introduced using methyllithium/methylbromide magnesium, the trifluoromethyl group is introduced using trifluoromethyltrimethylsilane (hereinafter referred to as $TMSCF_3$) in the presence of a catalytic amount of tetra-n-butylammonium fluoride (hereinafter referred to as TBAF) and for example, the ethinyl group is introduced using trimethylsilylethinylbromide magnesium.

The nucleophilic addition reaction proceeds stereospecifically: the nucleophile attacks from the least sterically hindered side and, since the bulky substituents on positions 1 and 3 are both on the same side, the nucleophile attacks at the opposite side, resulting in the stereoconformation illustrated by the figure.

Deprotection of the phosphonyl group as described above at this point, leads to 2'-di-substituted analogs. Alternatively, a double bond can be formed by dehydration between position 2 and position 3 prior to phosphonyl deprotection.

In a preferred embodiment of the invention this is achieved by base treatment, for example by treatment with sodium methanolate (hereinafter referred to as MeONa) in methanol.

Though in a preferred embodiment, this is done under aprotic conditions for example using DBU in an aprotic solvent such as dichloromethane (hereinafter referred to as DCM).

FIG. 4

Figure 4:
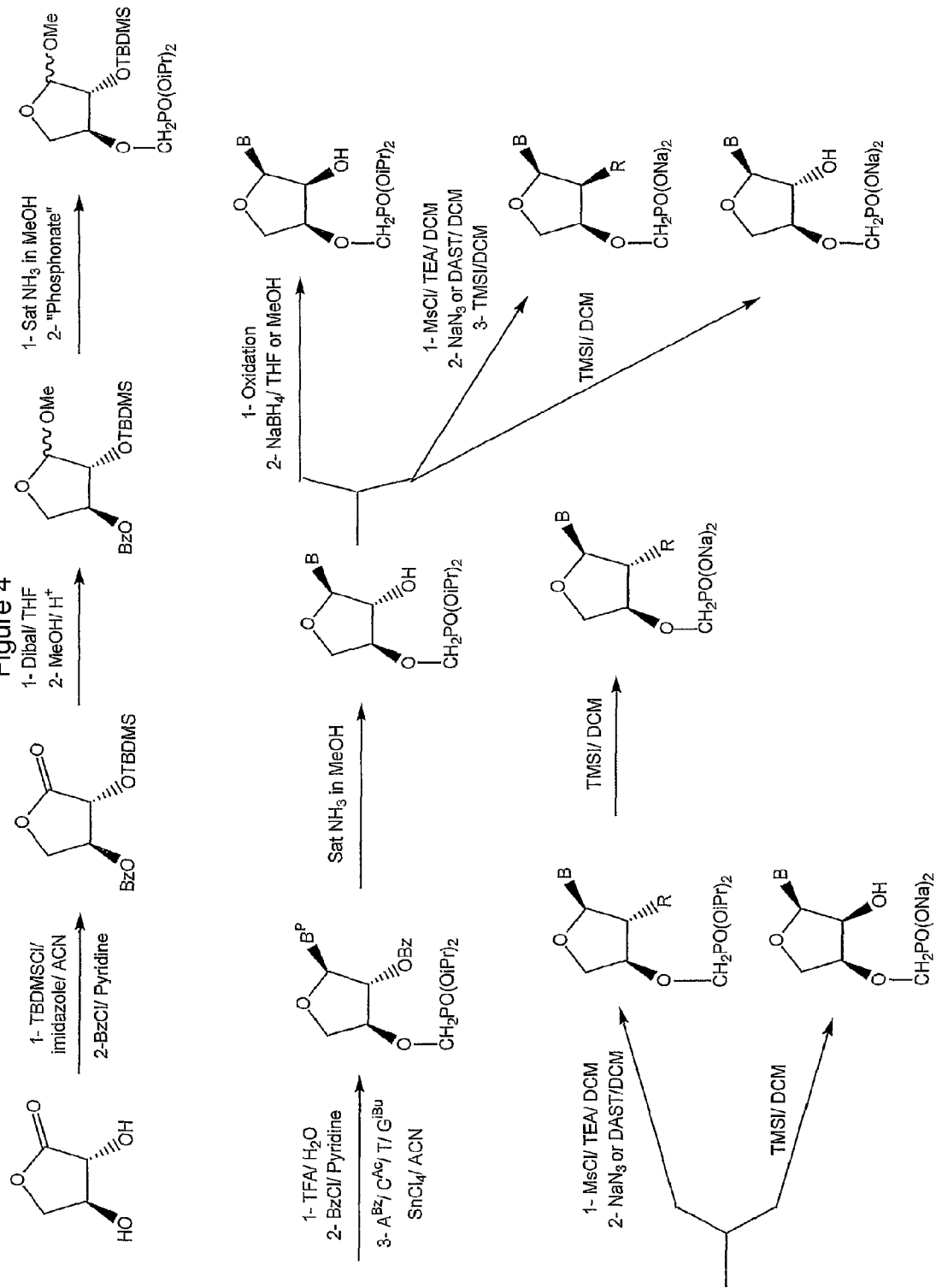

The reaction scheme given in FIG. 4 illustrates the synthesis of 3'-O-phosphonate and tetrose derivatives with different substituents on position 2 through an alternative pathway. The synthesis of these compounds is achieved in 10 steps, starting from (R,S)-2,3-dihydroxy-dihydro-furan-1-one.

The first 5 steps of the pathway in FIG. 4 are identical to the first 5 steps of the pathway in FIG. 3 resulting both in the same key intermediate. The hydroxy on position 2 of this intermediate is replaced by a substituent other than OH by a nucleophilic substitution optionally after activation of the hydroxy group as a leaving group. Activation of the hydroxy as a good leaving group is preferably done by mesylation, for example by reacting the hydroxy group with mesylchloride (hereinafter referred to as MsCl) in a base catalysed environment with for example TEA in an organic solvent such as DCM. The (activated) hydroxy group is substituted by nucleophilic attack resulting in inversion of the configuration at that carbon, for example the hydroxy is replaced by an azido group after treatment with sodiumazide. Alternatively a fluoride is introduced on position 2 replacing the hydroxy after reaction with N,N'-diethylaminosulfur trifluoride (DAST) as reagent.

Subsequent phosphonyl deprotection levers the next phosphonylated tetrose nucleoside.

The conformation of the hydroxy on position 2 of this key-intermediate is also inverted by an oxidation/reduction process. First the compound is treated by an oxidising agent identical to the ones described for step 6 in the pathway of FIG. 3. after the oxidation, the compound is reduced again, preferably by treatment with a metal hydride in an organic solvent for using sodiumborohydride (hereinafter referred to as NaBH$_4$) example THF or methanol.

The resulting compound of this oxidation/reduction process has a combination of configuration on positions 1, 2 and 3 that is novel. Therefore, in a next step, the remaining protecting groups, being the phosphonyl protecting groups, are removed by the same treatment as described above.

Alternatively, the intermediate resulting from the oxidation/reduction process undergoes nucleophilic substitution as described for an earlier step in this pathway. After, subsequent phosphonyl protecting group removal, another set of novel 3'-phosphonylated tetrose nucleoside analogs is synthesised.

FIG. 5

Figure 5:
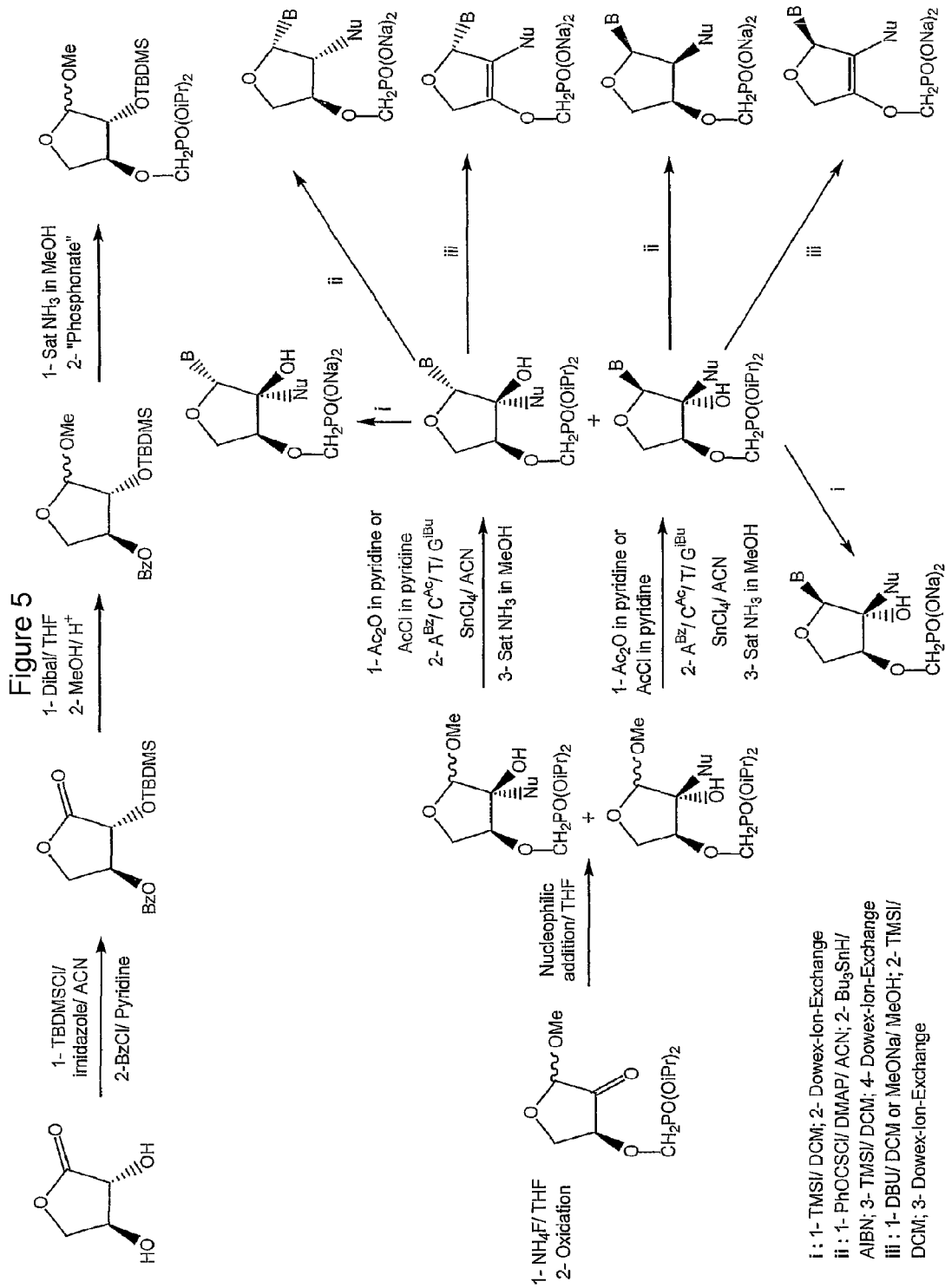

The reaction scheme given in FIG. 5 illustrates the synthesis of another set of 3'-O-phosphonate tetrose nucleoside derivatives with different substituents on position 2 through another pathway. The presented pathway comprises mostly steps or reactions that were used at some stage in the synthetic pathways of FIGS. 1-4 and which are described above, except for two reactions or steps. Starting with (R,S)-2,3-dihydroxy-dihydro-furan-1-one, the first three steps are identical to the first three steps in FIG. 3.

In the next step, the first reaction is a new one and is an alternative way of removal of silylprotecting groups namely a method using a fluoride reagent, preferably using ammonium fluoride in THF. The second reaction in this step is oxidation on position 2 for which the method has been described above for FIG. 3. The next step is nucleophilic addition on position 2 as described for FIG. 3 as well. The resulting product is a mixture of two diastereoisomers that are separated based on the difference of their fysicochemical properties yielding substantially pure stereoisomers by methods know to the person skilled in the art. The nucleophilic attack of this nucleophilic addition reaction is not stereospecific because the position is much less sterically hindered due to the much smaller substituent on position 1.

Next, the free hydroxy group on position 2 is protected by acylation, preferably benzoylation, followed by introduction of the nucleobase on position 1 and subsequent removal of the all the base-labile protecting groups, namely the protection of the nucleobase and the protection of the hydroxy on position 2. All three of these reactions have been described for steps four and five in FIG. 3.

The resulting compounds are then derivatized in three different ways. In one possible final step, the phosphonate protecting groups are removed using the same method as described for phosphonate deprotection in FIG. 1.

The second way is characterized by removal of the hydroxy on position 2. This is achieved by a mild method involving derivatization of the hydroxy group into a thionocarbonate or dithiocarbonate prior to radical reduction. An appropriate reaction process is known as Barton deoxygenation. Subsequent removal of the phosphonate protecting groups by the methods described above yields another set of 2'-nucleophile substituted derivatives. The third way involves a dehydration step as described for a final step in FIG. 3. In a preferred embodiment of the invention the dehydration is achieved by base treatment, for example by treatment with sodium methanolate (hereinafter referred to as MeONa) in methanol. Though in a preferred embodiment, this is done under aprotic conditions for example using DBU in an aprotic solvent such as dichloromethane (hereinafter referred to as DCM).

FIG. 6

Figure 6:
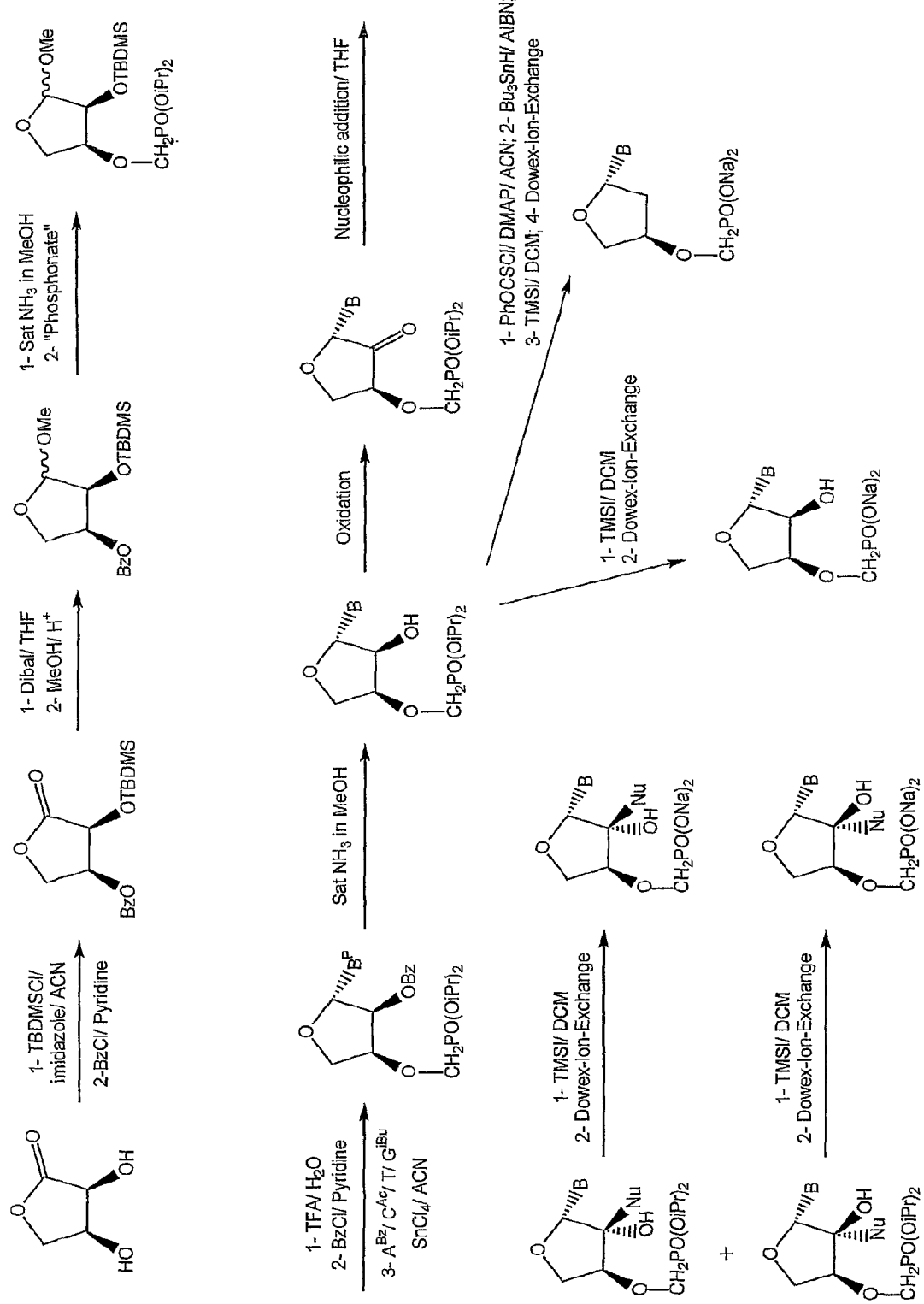

The reaction scheme given in FIG. 6 illustrates the synthesis of another set of 3'-O-phosphonate tetrose nucleoside derivatives with different substituents on position 2 through another pathway. "Different substituents" should be understood both in terms of different chemical composition as well as the same chemical substituents in a different stereoconformation. The presented pathway comprises only steps or reactions that were used at some stage in the synthetic pathways of FIGS. 1-5 and which are described above. This scheme illustrates how the use of a different stereoisomer of the starting material leads to different possibilities for synthesis.

More specifically, the first 6 steps of this synthetic route are identical to the first 6 steps of the synthetic pathway of FIG. 3. However, due to the fact that the orientation of the nucleobase relative to the orientation of the substituent on position 3 in the oxidation product is different from this relative orientation of the same compound in FIG. 3, subsequent nucleophilic addition, although performed under the same conditions, leads to nucleophilic attack from both sides in the pathway of FIG. 6 contrary to the stereoselectivity of this step in FIG. 3 (due to steric hindrance). The difference of stereoconfiguration of this key intermediate is due to the different stereoconformation of the starting material: (S,S)-2,3-dihydroxy-dihydro-furan-1-one. This leads to the formation of mixture of two diastereoisomers that can be separated as described above.

FIG. 7

Figure 7:
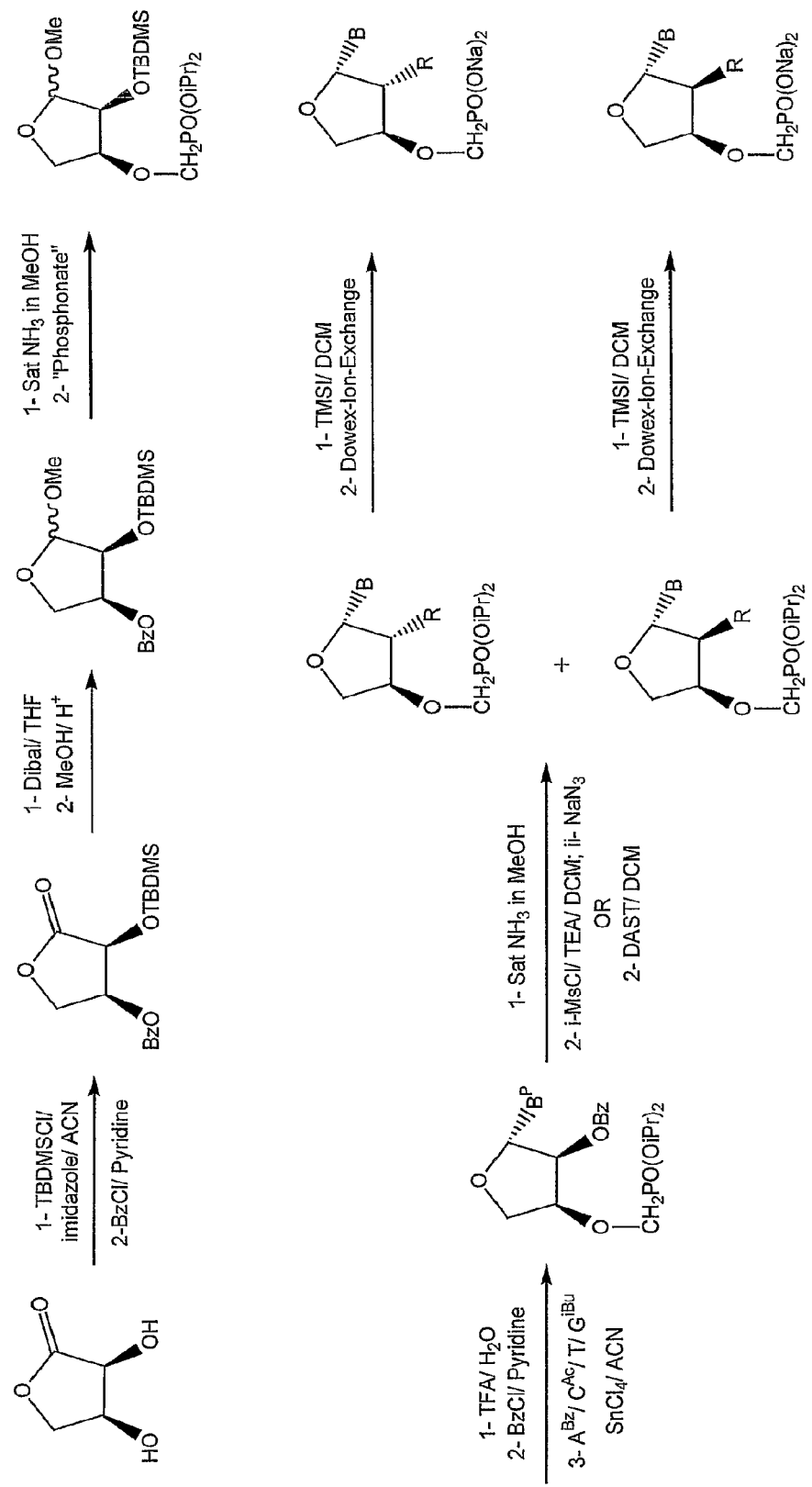

The same accounts for FIG. 7 as for FIG. 6. All the reactions used in the synthetic pathway of FIG. 7 are already described for the other synthetic pathways. However, due to the fact that the orientation of the nucleobase relative to the orientation of the substituent on position 3 in the oxidation product is different from this relative orientation of the same compound in FIG. 3, subsequent nucleophilic substitution, although performed under the same conditions, leads to nucleophilic attack from both sides in the pathway of FIG. 7 contrary to the stereoselectivity of this step in FIG. 4 (due to steric hindrance). The difference of stereoconfiguration of this key intermediate is due to the different stereoconformation of the starting material, (S,S)-2,3-dihydroxy-dihydrofuran-1-one. This leads to the formation of mixture of two diastereoisomers that can be separated as described above.

FIG. 8

Figure 8:
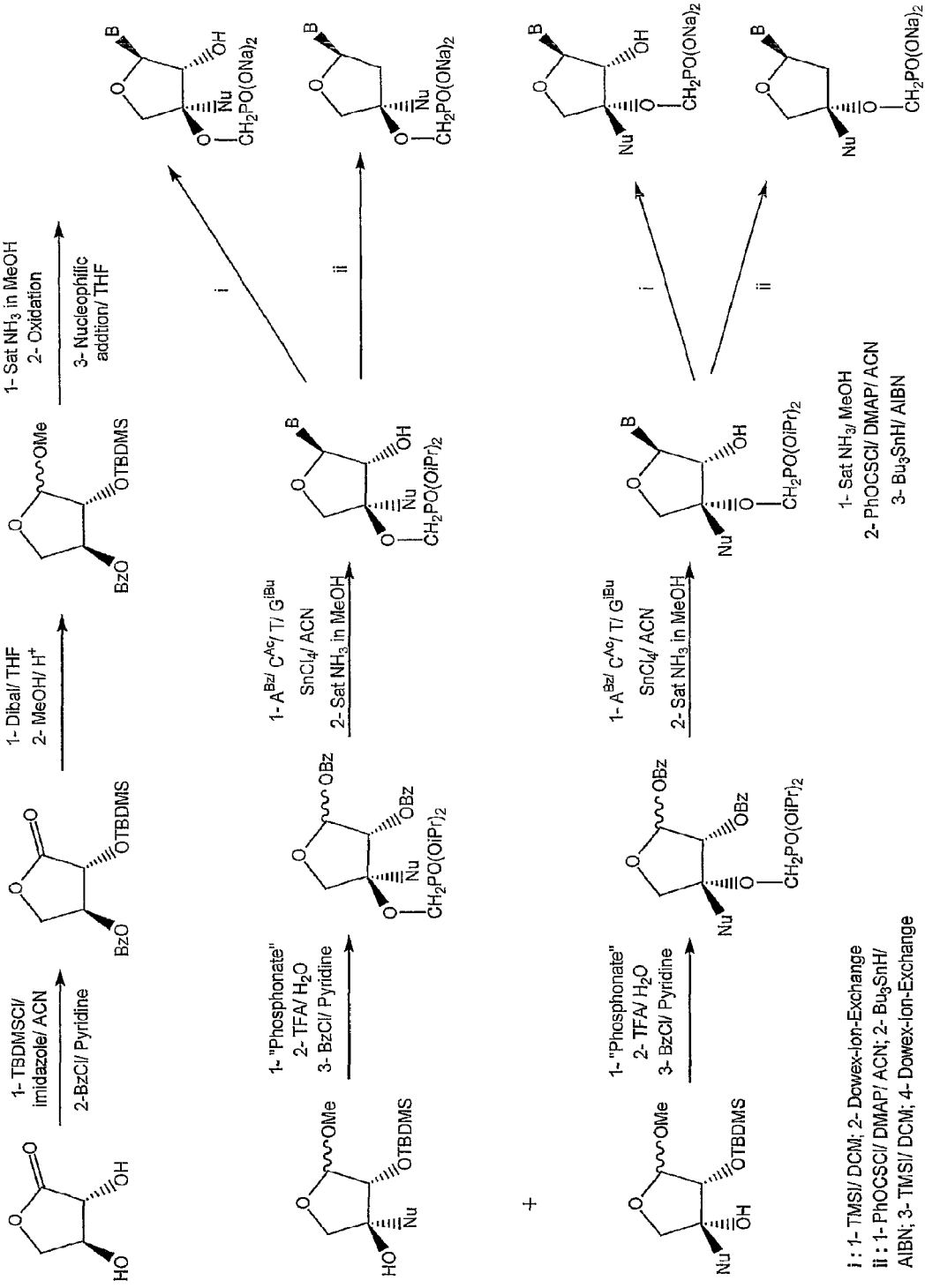

The reaction scheme given in FIG. 8 illustrates the synthesis of another set of 3'-O-phosphonate tetrose nucleoside derivatives with a second substituent on position 3. The pathway comprises 11 steps in total, start with (R,S)-2,3-dihydroxy-dihydro-furan-1-one and results in the synthesis of 4 end product groups (see boxed structures). The presented pathway comprises mostly steps or reactions that were used at some stage in the synthetic pathways of FIGS. 1-7 and which are described above but used in a different order (at a different stage of the chronological order of the synthetic pathway) and for some of the reactions to execute a modification at a different site of the molecule when compared to the previous synthetic pathways. For example, the oxidation reaction in step 3 of the pathway is carried out under the same conditions as described above (see FIG. 3) but is used to oxidize at position 3.

This synthetic pathway therefore very well illustrates the diversification of end products enabled by the reactions described in all FIGS. 1 to 15.

FIG. 9

Figure 9:
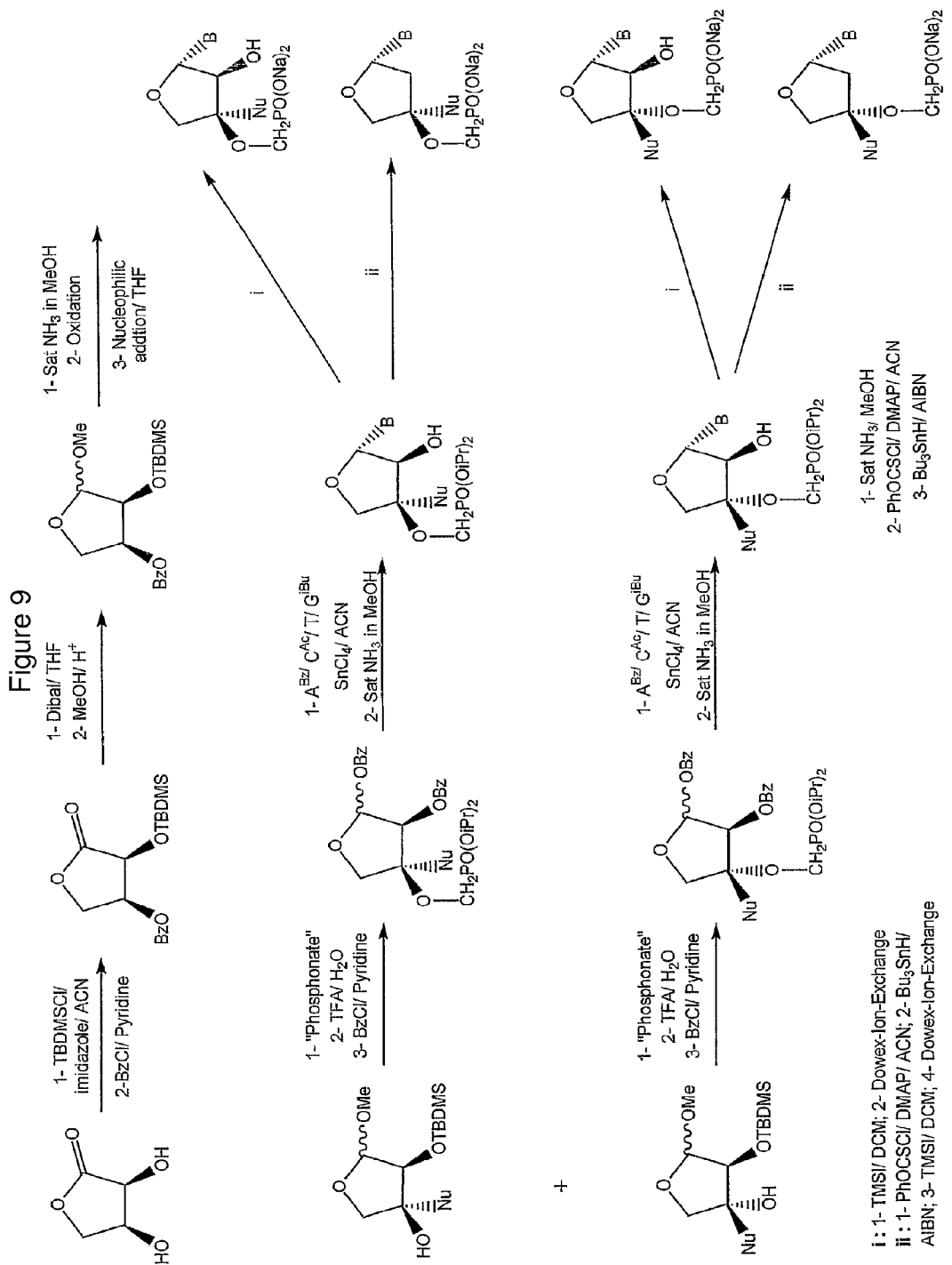

The reaction scheme given in FIG. 9 illustrates the synthesis of a set of 3'-O-phosphonate tetrose nucleoside derivatives similar to the compounds resulting from the synthesis in FIG. 8 but with different stereoconformation due to the use of the same starting material but in a different conformation. The starting material is (S,S)-2,3-dihydroxy-dihydro-furan-1-one.

FIG. 10

Figure 10:
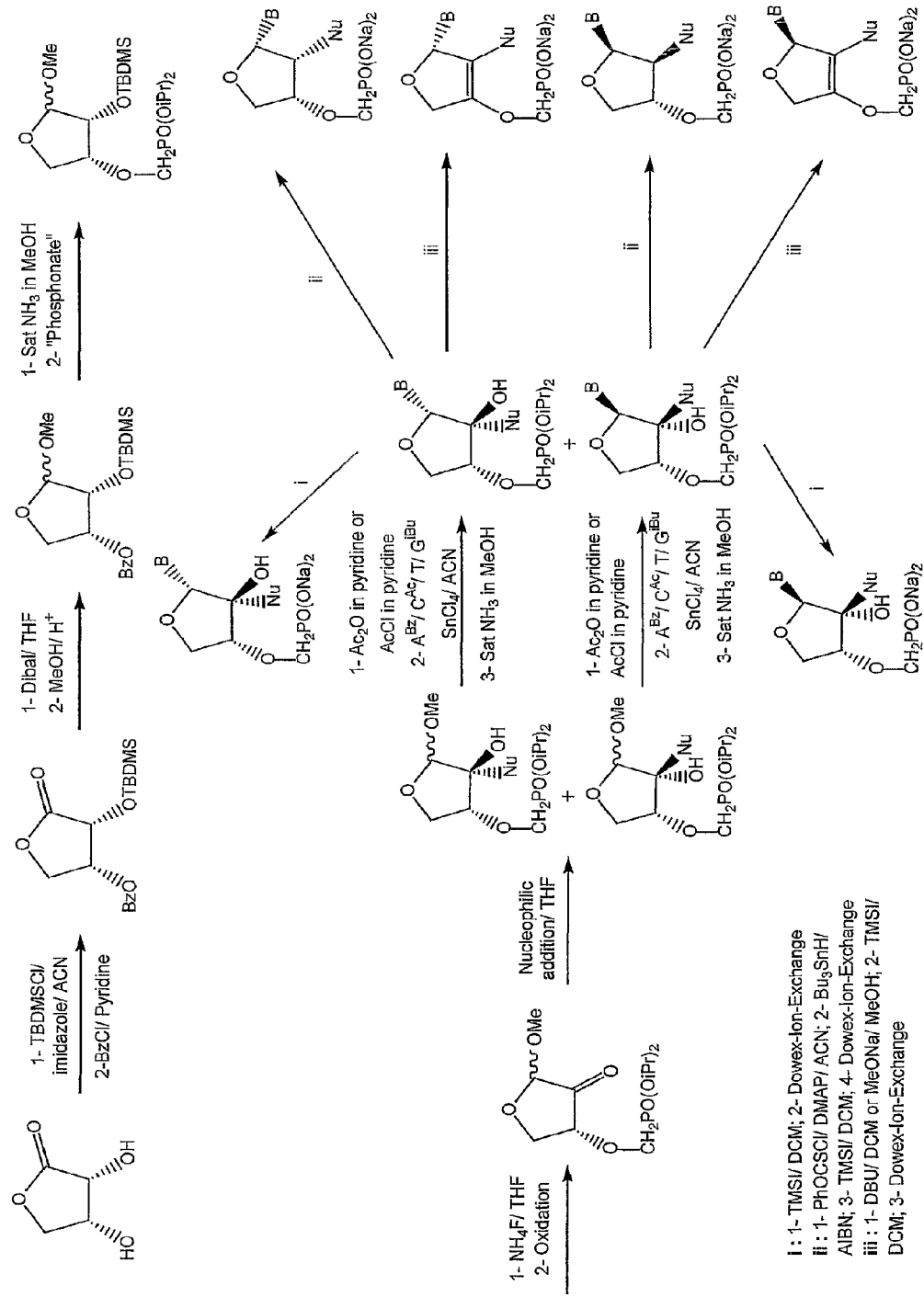

The reaction scheme given in FIG. 10 illustrates the synthesis of a set of 3'-O-phosphonate tetrose nucleoside derivatives similar to the compounds resulting from the synthesis in FIG. 5 but with different stereoconformation due to the use of the same starting material but in a different conformation. The starting material is (R,R)-2,3-dihydroxy-dihydro-furan-1-one.

FIG. 11

Figure 11:
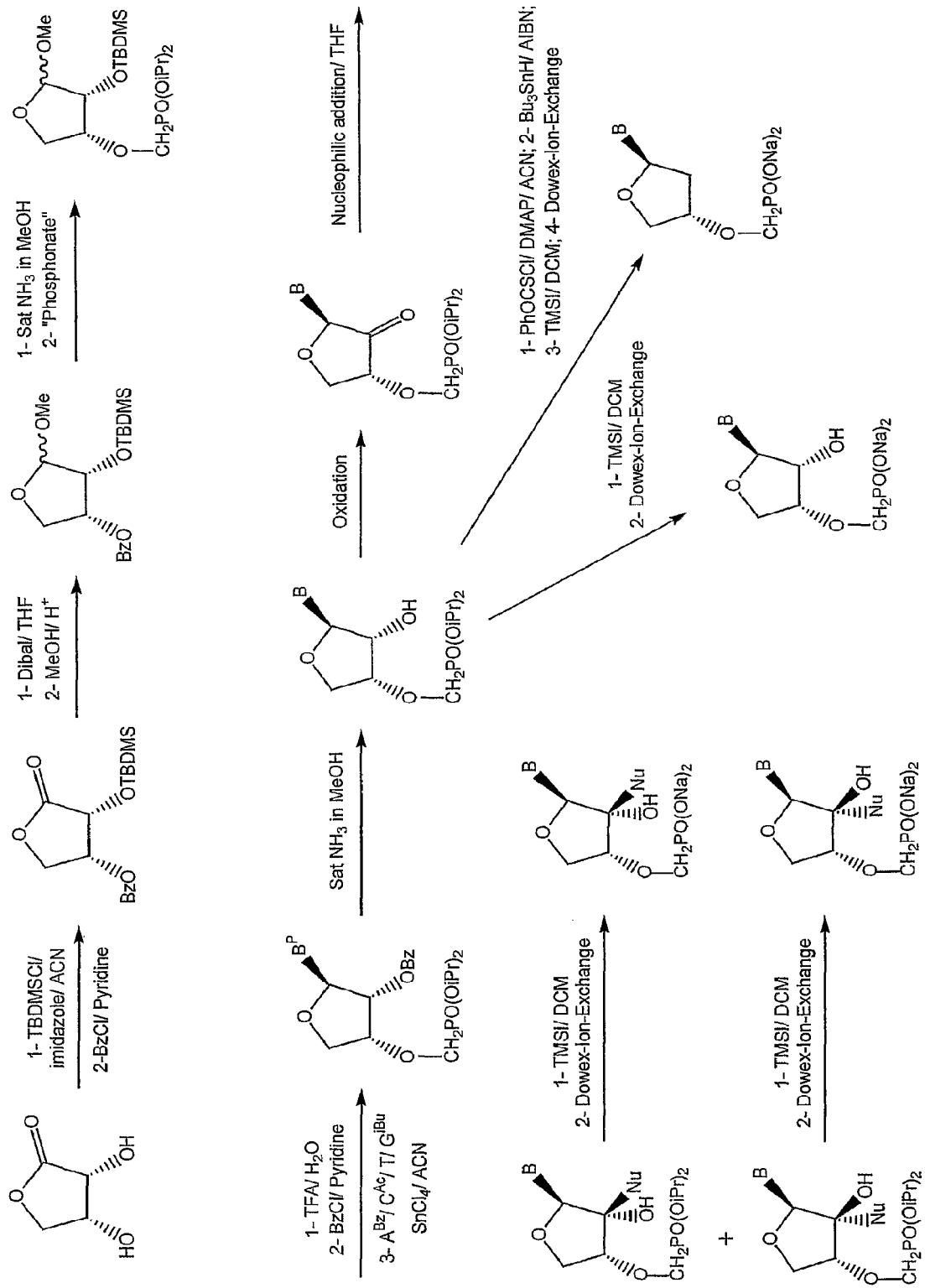

The reaction scheme given in FIG. 11 illustrates the synthesis of a set of 3'-O-phosphonate tetrose nucleoside derivatives similar to the compounds resulting from the synthesis in FIG. 6 but with different stereoconformation due to the use of the same starting material but in a different conformation. The starting material is (R,R)-2,3-dihydroxy-dihydro-furan-1-one.

FIG. 12

Figure 12:
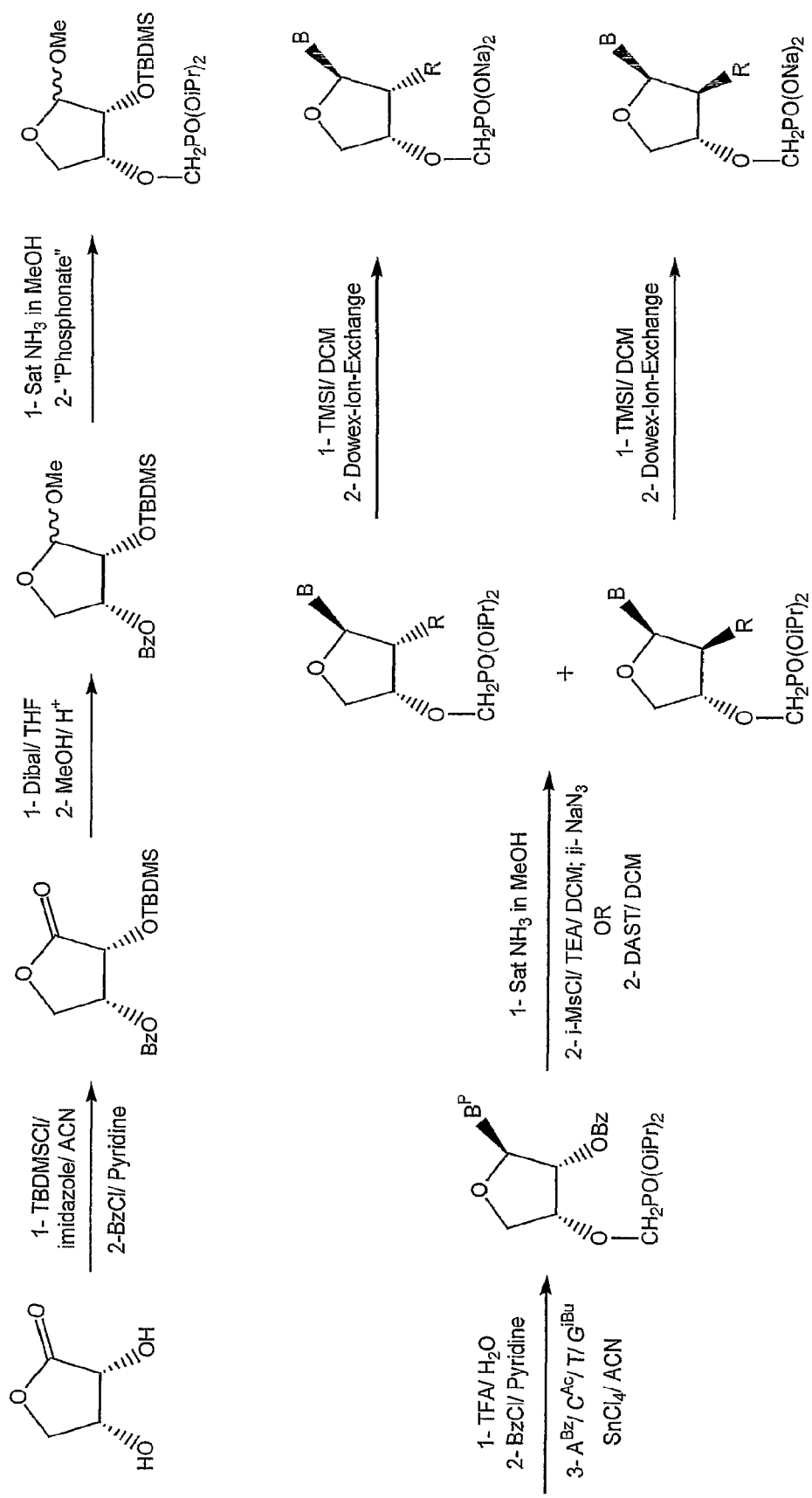

The reaction scheme given in FIG. 12 illustrates the synthesis of a set of 3'-O-phosphonate tetrose nucleoside derivatives similar to the compounds resulting from the synthesis in FIG. 7 but with different stereoconformation due to the use of the same starting material but in a different conformation. The starting material is (R,R)-2,3-dihydroxy-dihydro-furan-1-one.

FIG. 13

Figure 13:
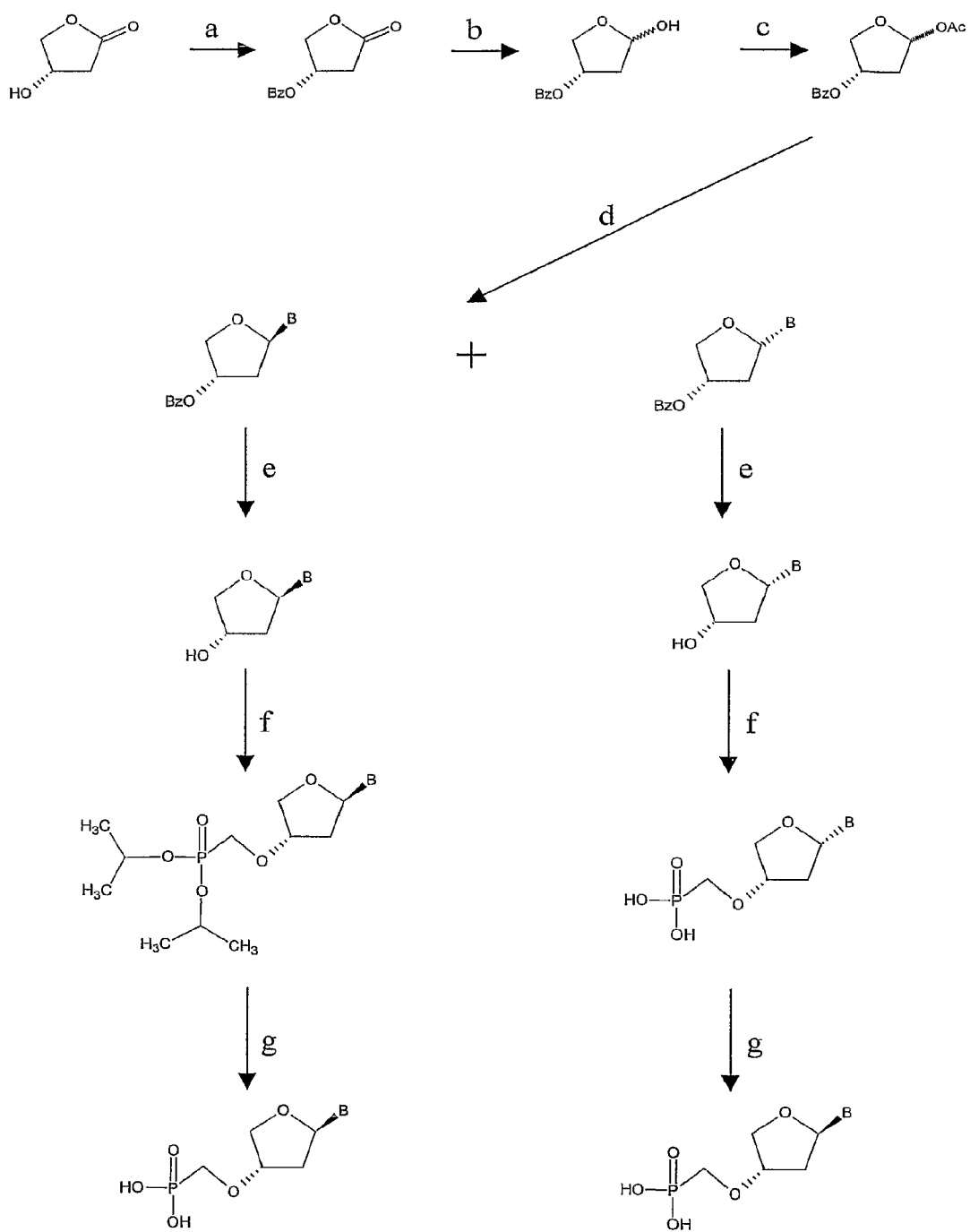

The reaction scheme in FIG. 13 illustrates the synthesis of a set of 3'-O-phosphonate tetrose nucleoside derivatives characterized by the absence of a substituent other than H on position 2. Although similar compounds have been synthesized through one of the pathways illustrated by FIGS. 1 to 12, the scheme in FIG. 13 describes an alternative pathway for the synthesis of these compounds by using different starting material: starting from β-Hydroxy-γ-butyrolactone which is commercially available. For the example given in FIG. 13, the stereoisomer (S)-β-Hydroxy-γ-butyrolactone is used.

In the first step, the hydroxyl group in position 3 is protected by benzoylation (reaction conditions see FIG. 1, step 2). In the second step, the lacton is reduced (reaction conditions see FIG. 1, step 3). The anomeric hydroxyl group is protected by acylation, preferably acetylation for example using acetic acid anhydride in triethylamine as the solvent and a catalytic amount of DMAP starting at 0° Celsius. and allow the reaction to proceed while warming up till room temperature. Subsequently, in the fourth step, the nucleobase is introduced, preferably using $SnCl_4$ as Lewis catalyst, giving a mixture of two stereoisomers with the base moiety in β and α configuration respectively. This mixture is separated based on the difference of physico-chemical properties of diastereoisomers preferably using chromatographic techniques for example preparative thin layer chromatography.

In the next step, both compounds undergo deprotection of the hydroxy group on position 3 using the same procedure as previously described removal of base labile-protecting groups for step 4 in FIG. 1. Next, the phosphonate function is introduced using the same procedure as step 5 in FIG. 1. Finally, the phosphonate protection groups are removed and the compounds purified following the same procedures as previously described for the compounds in FIGS. 1-13.

FIG. 14

Figure 14:
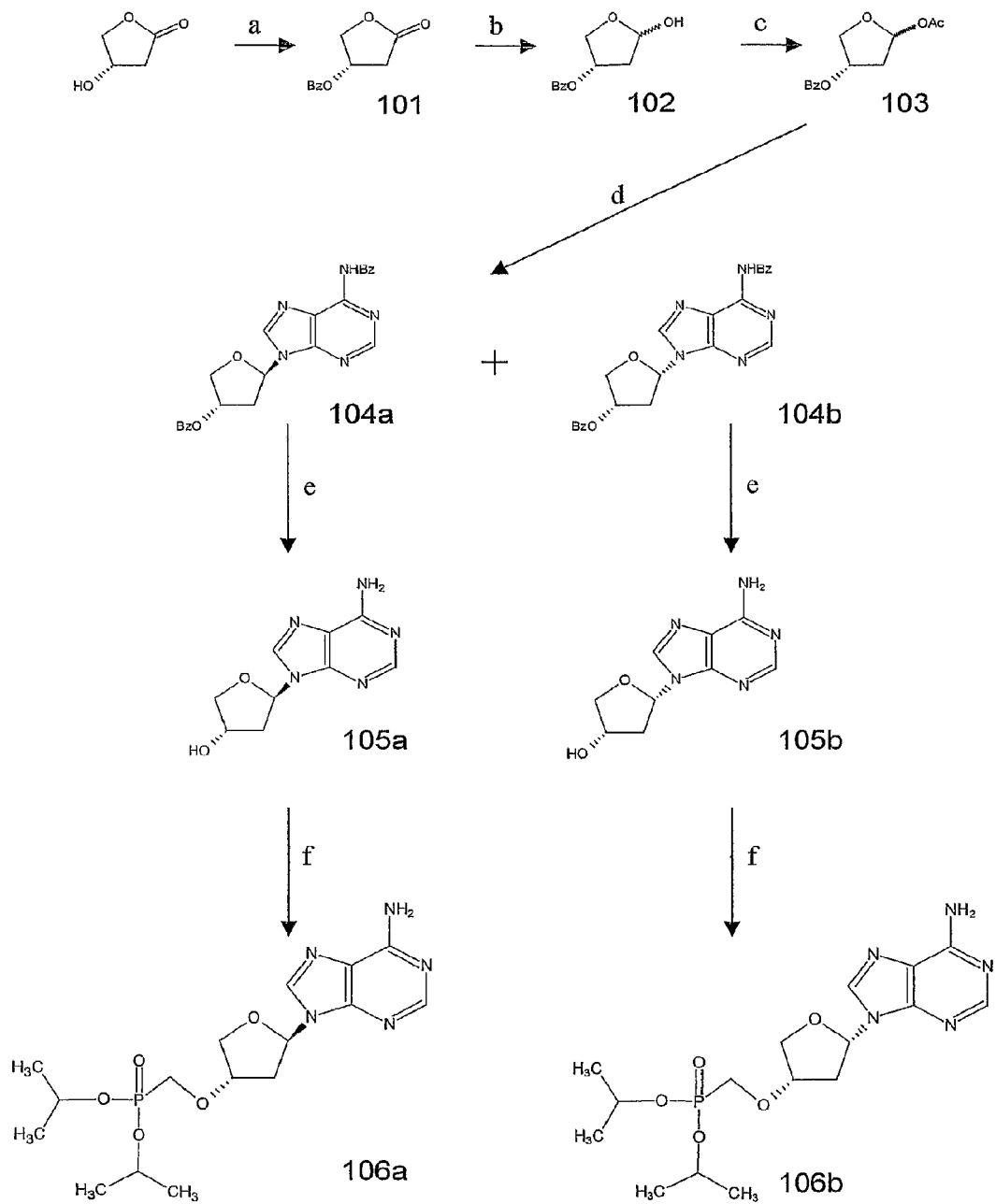

FIG. 14 exemplifies the synthetic pathway illustrated by FIG. 13 for the adenine derivatives.

FIG. 15

Figure 15:
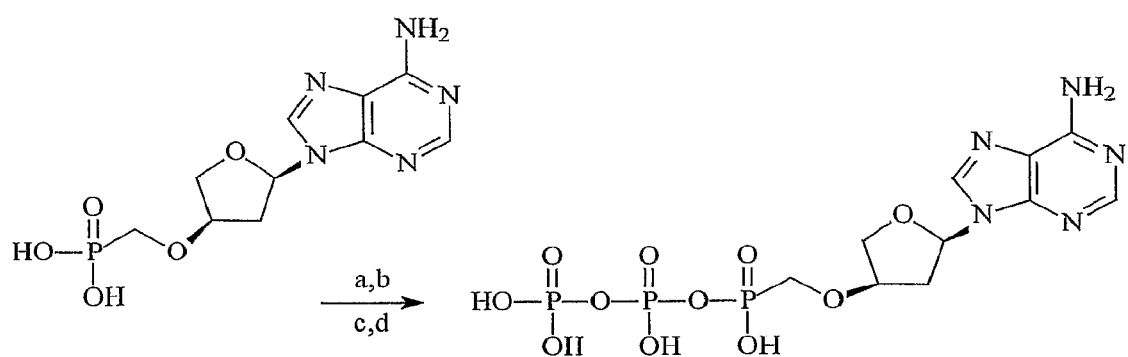

FIG. 15 illustrates a possible way to synthesize the triphosphate analogue of the of the present invention. Several methods for transforming a nucleoside monophosphate into a tri-phosphate are known to the person skilled in the art and all these methods are suitable for introducing two phosphate groups onto the phosphonyl group of the phosphonoalkyloxytetrose nucleoside analogs of the present invention. Preferably, a diphosphate is introduced onto the phosphonyl group of the phosphonylated tetrose nucleoside derivatives synthesized following one of the pathways as illustrated by FIGS. 1-14, by first treatment of a solution of the compound in an organic solvent for example DMF, with dimethylformamide dimethyl acetal at room temperature overnight. After subsequent evaporation of the solvent, the residue is dissolved in an organic solvent again, preferably DMF, and treated with N,N'-carbonyldiimidazole. After 12 h a solution of dibutylammonium pyrophosphate is added and the mixture is kept at room temperature for 2 h. Then the mixture is treated with NH$_4$OH and subsequently concentrated under reduced pressure. The resulting phosphonyl-diphosphate is purified by methods known to the person skilled in the art, preferably column chromatography, for example reversed phase chromatography.

General Methods for Antiviral Screening

General methods that can be used for testing the anti-viral activity of the compounds of this invention include, but are not limited to, the following:

Anti-HIV Assay:

The inhibitory activity of compounds of the invention can be tested for their potential to inhibit the replication of HIV and SIV in a cell culture model for acute infection. Compounds can be tested against HIV-1 strains (NL43, III$_B$), HIV-2 strains (ROD, EHO), and SIV (MAC251) for inhibition of virus-induced cytopathicity in MT-4 cells (or CEM or C8166 or Molt4/C8 cells), using the colorimetric test described by Pauwels et al. in *J. Virol. Methods* (1988) 20:309-321 or a microscopic investigation of the cytopathogenic effect, evaluation being made 4 to 5 days post-infection. For example microtiter 96-well plates containing ~3×10$^5$ CEM cells/ml, infected with 100 CCID$_{50}$ of HIV per ml and containing appropriate dilutions of the test compounds can be used. A rapid and automated assay procedure can be used for the in vitro evaluation of anti-HIV agents. An HTLV-1 transformed T4-cell line MT-4, which was previously shown to be highly susceptible to and permissive for HIV infection, can serve as the target cell line. Inhibition of the HIV-induced cytopathogenic effect is used as the end point. The viability of both HIV- and mock-infected cells is also assessed spectrophotometrically via in situ reduction of 3(4,5-dimethylthiazol-2-yl)-2,5-diphenyltetrazolium bromide (MTT). Methods comprise for example the microscopic examination of CEM, C8166 or Molt4/C8 giant (syncytium) cell formation, after 4 to 5 days of incubation at 37° C. in a CO$_2$-controlled humidified atmosphere. The 50% cytotoxic concentration (CC$_{50}$ in µg/ml) is defined as the concentration of compound that reduces the absorbance of the mock-infected control sample by 50%. The percent protection achieved by the compound in HIV-infected cells is calculated by the following formula:

$$\frac{(OD_T)_{HIV} - (OD_C)_{HIV}}{(OD_C)_{MOCK} - (OD_C)_{HIV}} \text{ expressed in \%}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values are determined at 540 nm. The dose achieving 50% protection according to the above formula is defined as the 50% inhibitory concentration (IC$_{50}$ in µg/ml). The ratio of CC$_{50}$ to IC$_{50}$ is defined as the selectivity index (SI).

Cells: MT-4 cells (Miyoshi et al., 1982) are grown and maintained in RPMI 1640 medium supplemented with 10% heat-inactivated fetal calf serum, 2 mM L-glutamine, 0.1% sodium bicarbonate, and 20 µg of gentamicin per ml.

Viruses: The HIV-1 (IIIB, NL4.3) strain (Adachi et al., 1986) is a molecular clone obtained from the National Institutes of Health (Bethesda, Md.). The HIV-1 strain SO561945 (RT, K103N; Y181C) is a strain resistant to non-nucleoside reverse transcriptase inhibitors. The HIV-2 (ROD, EHO) (Barré-Sinoussi et al., 1983) stock is obtained from culture supernatant of HIV-2 infected cell lines. Mac251 is a SIV strain.

Cytostatic Activity Assays:

All assays are performed in 96-well microtiter plates. To each well are added 5-7.5×10$^4$ cells and a given amount of the test compound. The cells are allowed to proliferate for 48 h (murine leukemia L1210) or 72 h (human lymphocyte CEM and Molt4/clone 8) at 37° C. in a humidified CO$_2$-controlled atmosphere. At the end of the incubation period, the cells can be counted in a Coulter counter. The IC$_{50}$ (50% inhibitory concentration) was defined as the concentration of the compound that reduced the number of cells by 50%.

Anti-BVDV Assay:

Cells and viruses: Madin-Darby Bovine Kidney (MDBK) cells are maintained in Dulbecco's modified Eagle medium (DMEM) supplemented with BVDV-free 5% fetal calf serum (DMEM-FCS) at 37° C. in a humidified, 5% CO$_2$ atmosphere. BVDV-1 (strain PE515) is used to assess the antiviral activity in MDBK cells. Vero cells (ATCC CCL81) are maintained in MEM medium supplemented with 10% inactivated calf serum, 1% L-glutamine and 0.3% bicarbonate.

96 well cell culture plates are seeded with MDBK cells in DMEM-FCS so that cells reach 24 hr later confluency. Then medium is removed and serial 5-fold dilutions of the test compounds are added in a total volume of 100 ul, after which the virus inoculum (100 ul) can be added to each well. The virus inoculum used results normally in a greater than 90% destruction of the cell monolayer after 5 days incubation at 37° C. Uninfected cells and cells receiving virus without compound can be included in each assay plate. After 5 days, medium is removed and 90 µl of DMEM-FCS and 10 ul of MTS/PMS solution (Promega) are added to each well. Following a 2 hours incubation period at 37° C., the optical density of the wells is read at 498 nm in a microplate reader. The 50% effective concentration (EC$_{50}$) value is defined as the concentration of compound that protects 50% of the cell monolayer from virus-induced cytopathic effect.

Anti-HCV Assay/Replicon Assay:

Huh-5-2 cells [a cell line with a persistent HCV replicon I389luc-ubi-neo/NS3-3'/5.1; replicon with firefly luciferase-ubiquitin-neomycin phosphotransferase fusion protein and EMCV-IRES driven NS3-5B HCV polyprotein] are cultured in RPMI medium (Gibco) supplemented with 10% fetal calf serum, 2 mM L-glutamine (Life Technologies), 1× non-essential amino acids (Life Technologies); 100 IU/ml penicillin and 100 ug/ml streptomycin and 250 ug/ml G418 (Geneticin, Life Technologies). Cells are seeded at different densities, particularly in a density of 7000 cells per well in 96 well View Plate™ (Packard) in medium containing the same components as described above, except for G418. Cells are then allowed to adhere and proliferate for 24 hours. At that time, culture medium is removed and serial dilutions of the test compounds are added in culture medium lacking G418. Interferon alfa 2a (500 IU) are included as a positive control. Plates are further incubated at 37° C. and 5% CO$_2$ for 72 hours. Replication of the HCV replicon in Huh-5 cells results in luciferase activity in the cells. Luciferase activity is measured by adding 50 µl of 1× Glo-lysis buffer (Promega) for 15 minutes followed by 50 µl of the Steady-Glo Luciferase assay reagent (Promega). Luciferase activity is measured with a luminometer and the signal in each individual well is expressed as a percentage of the untreated cultures. Parallel cultures of Huh-5-2 cells, seeded at a density of 7000 cells/well of classical 96-well cell culture plates (Becton-Dickinson) are treated in a similar fashion except that no Glo-lysis buffer or Steady-Glo Luciferase reagent is added. Instead the density of the culture is measured by means of the MTS method (Promega).

Anti-Coxsackie Virus Assay:

96-well cell culture plates is seeded with Vero cells in DMEM medium containing 10 fetal calf serum (FCS) so that cells reache confluency 24 to 48 hours later. Medium are then removed and serial 5-fold dilutions of the test compounds are added in a total volume of 100 ul, after which the virus inoculum (100 µl) is added to each well. The virus inoculum used results normally in a 90-100% destruction of the cell monolayer after 5 days incubation at 37° C. Uninfected cells and cells receiving virus without compound can be included in each assay plate. After 5 days, the medium is removed and 90 µl of DMEM-FCS and 10 µl of MTS/PMS solution (Promega) is added to each well. Following a 2 hours incubation period at 37° C., the optical density of the wells can be read at 498 nm in a microplate reader. The 50% effective concentration (EC50) value is defined as the concentration of compound that protects 50% of the cell monolayer from virus-induced cytopathic effect.

Anti-Herpes simplex virus, varicella-zoster virus and cytomegalovirus assays: The antiviral assays HSV-1, HSV-2, VZV, CMV are based on inhibition of virus-induced cytopathicity in HEL cell cultures. Confluent cell cultures in microtiter 96-well plates are inoculated with 100 $CCID_{50}$ of virus, 1 $CCID_{50}$ being the virus dose required to infect 50% of the cell cultures. After a 1 hour to 2 hours virus adsorption period, residual virus is removed, and the cell cultures is incubated in the presence of varying compound concentrations of the test compounds. Viral cytopathicity is recorded as soon as it reaches completion in the control virus-infected cell cultures that are not treated with the test compounds.

Feline Corona Virus Assay:

Feline Crandel kidney cells are seeded in 96-well microtiter plates at 24,000 cells/well. Then, 24 hrs later, an appropriate inoculum of FCV can be added together with 5-fold dilutions of the test compounds. After 4 days, a MTS/PMS solution can be added to each well. Following a 90 min incubation period at 37° C., the optical density of the wells can be read at 498 nm in a microplate reader.

SARS virus assay: Vero cells can be seeded in 96-well microtiter plates and grown till confluency. Then, an appropriate inoculum of SARS virus able to kill the cell culture (cytopathicity) within 72 hrs can be added together with 5-fold dilutions of the test compounds. After 3 days, a MTS/PMS solution can be added to each well. Following a 3 h incubation period at 37° C. the optical density of the wells can be read at 498 nm in a microplate reader.

Anti-Hepatitis B Virus Assay:

The tetracycline-responsive cell lines HepAD38 are used (Ladner et al. in *Antimicrob Agents Chemother.* (1997) 41:1715-1720). These are hepatoma cells that have been stably transfected with a cDNA copy of the pregenomic RNA of wild-type virus. Withdrawal of tetracycline from the culture medium results in the initiation of viral replication. Cells are cultured at 37° C. in a humidified 5% $CO_2$/air atmosphere in seeding medium, DMEM/Ham's F12 (50/50) supplemented with 10% by volume heat-inactivated fetal calf serum, 100 IU/ml penicillin, 50 µg/ml streptomycin, 100 µg/ml kanamycin, 400 µg/ml G418 and 0.3 µg/ml tetracycline. When the assay is started, the cells are seeded in 48-well plates at a density of $5 \times 10^5$/well. After 2 to 3 days the cultures are induced for viral production by washing with prewarmed PBS and are fed with 200 µl assay medium (seeding medium without tetracycline and G418) with or without the antiviral compounds. Medium is changed after 3 days. The antiviral effect is quantified by measuring levels of viral DNA in culture supernatant at day 6 post-induction, by a real time quantitative PCR (Q-PCR). The Q-PCR is performed with 3 µl of culture supernatant in a reaction volume of 25 µl using the TaqMan Universal PCR Master Mix (Applied Biosystems, Branchburg, N.J.) with forward primer (5'-CCG TCT GTG CCT TCT CAT CTG-3'(SEQ ID NO:1); final concentration: 600 nM), reversed primer (5'-AGT CCA AGA GTY CTC TTA TRY AAG ACC TT-3'(SEQ ID NO: 2); final concentration: 600 nM), and Taqman probe (6-FAM-CCG TGT GCA CTT CGC TTC ACC TCT GC-TAMRA (SEQ ID NO:3); final concentration 150 nM). The reaction is analyzed using a SDS 7000 (Applied Biosystems, Foster City, Calif.). A plasmid containing the full length insert of the HBV genome is used to prepare the standard curve. The amount of viral DNA produced in treated cultures is expressed as a percentage of the mock treated samples. The cytostatic effect of the various compounds is assessed employing the parent hepatoma cell line HepG2. The effect of the compounds on exponentially growing HepG2 cells is evaluated by means of the MTS method (Promega). Briefly, cells are seeded at a density of 3000/well (96 well plate) and are allowed to proliferate for 3 days in the absence or presence of compounds, after which time cell density is determined.

EXAMPLE 1

Materials and General Preparation Methods

For all reactions, analytical grade solvents are used. All moisture sensitive reactions were carried out in oven-dried glassware (135° C.) under a nitrogen atmosphere. Anhydrous THF was refluxed over sodium/benzophenone and distilled. A Varian Unity 500 MHz spectrometer and a 200 MHz Varian Gemini apparatus were used for $^1$H NMR and $^{13}$C NMR. Exact mass measurements were performed on a quadrupole time-of-flight mass spectrometer (Q-Tof-2, Micromass, Manchester, UK) equipped with a standard electrospray-ionization (ESI) interface; samples were infused in i-PrOH/$H_2O$ 1:1 at 3 µL/min. Precoated aluminum sheets (Fluka Silica gel/TLC-cards, 254 nm) were used for TLC. The spots were examined with UV light. Column chromatography was performed on ICN silica gel 63-200 60 Å.

The nucleosides (3a-h) were synthesized starting from (R,R)-2,3-dihydroxy-dihydro-furan-1-one (4) according to FIG. 1. The hydroxyl group in position 2 can be selectively protected with a TBDMS group. The free hydroxyl group of 5 is then protected by benzoylation and the lacton is reduced to the hemiketal using Dibal-H in THF. The anomeric hydroxyl group is protected with a TBDMS group and the O-benzoyl group is removed with ammonia in methanol. At the stage of 8, the phosphonate function is introduced using the triflate of diisopropylphosphonomethyl alcohol and NaH in THF. The two silyl protecting groups of 9 are removed and replaced by benzoyl protecting groups. The presence of a 2-O-benzoyl group allows selective introduction of the base moiety in the β-configuration. The nucleobases (uracil, thymine, $N^6$-benzoyladenine, $N^4$-acetylcytosine) are introduced after silylation and using $SnCl_4$ as Lewis catalyst. Deprotection of 11-14 is done in two steps, first, removal of the benzoyl protecting groups with ammonia in methanol (yielding 15-18), and, second, hydrolysis of the diisopropyl protecting groups with TMSBr at room temperature (giving 3a-d). In order to obtain the 2'-deoxygenated analogues, the 2'-OH group of 15-17 is removed by Barton deoxygenation,[16,17] giving 19-21. Compound 22 is obtained from 21. Hydrolysis of the phosphonate ester function of 19 was carried out with TMSBr at room temperature. However, for the compounds 20-22, TMSBr rapidly cleaved the nucleobase from the sugar even at 0° C. For this reason, TMSI was used for hydrolysis of the (diisopropylphosphono)-methyl group of 20-22. After purification by silica gel chromatography, sephadex-DEAE A-25 resin and Dowex-sodium ion exchange resin, nucleoside phosphonates acid 3 e-h were obtained.

Conditions for each step of FIG. 1 may be summarized as follows: a) TBDMSCl, imidazole, MeCN b) BzCl, pyridine c) Dibal-H, THF d) Sat. $NH_3$ in MeOH e) Trifluoromethanesulfonate of diisopropylphosphonylmethanol, NaH, THF f) $TFA/H_2O$ g) $SnCl_4$, MeCN h) 1. $\phi OC(S)Cl$, DMAP, MeCN 2.$Bu_3SnH$, AIBN i) $P(O)Cl_3$, 1,2,4-triazole, DCM 2. j) 1. TMSBr, DCM sephadex-DEAE, Dowex-$Na^+$·k) 1. TMSI, DCM 2. sephadex-DEAE, Dowex-$Na^+$.

EXAMPLE 2

Preparation of Intermediate Compounds

2-O-tributyldimethylsilyl-L-threonolactone (5)

To the solution of (3R,4S)-dihydro-3,4-dihydroxyfuran-2 (3H)-one 4 (10.8 g, 92 mmol) and imidazole (12.5 g, 184 mmol) in 250 mL MeCN was added TBDMSCI (31.2 g, 3.17 mmol) at 0° C. in one portion. The reaction mixture was slowly warmed to room temperature and stirred overnight. The reaction mixture was concentrated. The residue was partitioned between $H_2O$ and EtOAc. The organic layer was washed with water and brine, and concentrated in vacuo. The residue was purified by chromatography on a silica gel column (n-hexane/EtOAC=6:1) to afford 5 (15.2 g, 65.4 mmol, yield 71%) as a colorless solid which was characterized as follows:

$^1$H NMR (200 MHz, DMSO-d6) $\delta_H$ 0.12 (s, 6H, $SiCH_3$), 0.90 (s, 9H, $CH_3$), 3.86 (dd, $J_1$=6.96 Hz, $J_2$=7.70 Hz, 1H, C(4')$H_a$), 4.11-4.36 (m, 3H, OH, C(3')H, C(4')$H_b$), 5.82 (d, J=5.13 Hz, 1H, C(2')H);

$^{13}$C NMR (200 MHz, DMSO-d6) $\delta_C$ -4.93 ($SiCH_3$), 17.99 (C($CH_3$)$_3$), 25.61 (C($\overline{CH_3}$)$_3$), 69.62 (C-4'), 72.62 (C-2), $\overline{74.59}$ (C-3'), 174.60 ($\overline{C}$-1');

calcd for $C_{10}H_{20}O_4Si_1Na_1$ $[M+Na]^+$ 255.1028, found 255.1010.

2-O-tributyldimethylsilyl-3-O-benzoyl-L-threonolactone (6)

To the solution of 5 (18.00 g, 77.5 mmol) in 200 mL pyridine was added dropwise BzCl (11.2 mL, 96.9 mmol) at 0° C. The reaction mixture was warmed to room temperature and stirred overnight. The reaction mixture was concentrated and coevaporated with 20 mL toluene two times in vacuo. The residue was partitioned between $H_2O$ (100 mL) and EtOAc (350 mL). The organic layer was washed with water and brine, and concentrated in vacuo. The residue was purified by chromatography on a silica gel column (n-hexane/EtOAc=8: 1) to afford 6 (25.9 g, 77.0 mmol) as a colorless solid in 99% yield which was characterized as follows:

$^1$H NMR (500 MHz, DMSO-d6) $\delta_H$ 0.14 (d, $J_1$=13.2, 6H, $SiCH_3$), 0.87 (s, 9H, $CH_3$), 4.23 (dd, $J_1$=6.8 Hz, $J_2$=9.3 Hz, 1H, C(4') $H_a$), 4.68 (dd, $J_1$=7.3 Hz, $J_2$=9.3 Hz, 1H, C(4') $H_b$), 4.96 (d, J=6.8 Hz, 1H, C(2')H), 5.48 (dd, $J_1$=7.3 Hz, $J_2$=13.0 Hz, 1H, C(3')H), 7.57-8.01 (m, 5H, Ar—H);

$^{13}$C NMR (500 MHz, DMSO-d6) $\delta_c$ -5.16 ($SiCH_3$), -4.84 ($SiCH_3$), 17.84 (C($CH_3$)$_3$), 25.42 (C($\overline{CH_3}$)$_3$), 67.20 (C-$\overline{4}$'), 71.67 (C-$\overline{2}$'), 75.46 (C-3'), 128.$\overline{65}$ (aroma-C), 128.90 (aroma-C), 129.36 (aroma-C), 133.94 (aroma-C), 165.08 (Bz-CO), 172.76 (C-1');

mass calcd for $\overline{C_{17}}H_{25}O_5Si_1$ $[M+H]^+$ 337.1471, found 337.1465.

2-O-tributyldimethylsilyl-3-O-benzoyl-L-threose (7)

To the solution of 6 (10.0 g, 29.7 mmol) in 100 mL dry THF was slowly dropwise added 1.0 M diisopropyl aluminiumhydride (37.1 mL, 37.1 mmol) in toluene at -78° C. The reaction mixture was stirred at -78° C., and as soon as the starting material was completely consumed (TLC, 4 to 10 hours), methanol (10 mL) was added over a period of 5 minutes in order to quench the reaction. The cooling bath was removed, 100 mL of a sat. aq. sodium potassium tartrate solution and 200 mL of EtOAc were added and the mixture stirred vigorously for 3 hours. The organic layer was washed with water and brine, and concentrated in vacuo. The residue was purified by chromatography on a silica gel column (n-hexane/EtOAc=8:1) to afford 7 (7.40 g, 21.8 mmol) as a colorless solid in 73% yield, which was characterized as follows:

$^1$H NMR (200 MHz, DMSO-d6) $\delta_H$ 0.10 (s, 6H, Si—$CH_3$), 0.87 (s, 9H, $CH_3$), 3.93 (dd, $J_1$=9.89 Hz, $J_2$=3.66 Hz, 1H, C(4')$H_a$), 4.16 (br s, 1H, OH), 4.24 (dd, $J_1$=10.26 Hz, $J_2$=5.86 Hz, 1H, C(4')$H_b$), 5.02-5.07 (m, 2H, C(2')H, C(3')H), 6.54 (d, J=4.76 Hz, 1H, C(1')H), 7.51-8.00 (m, 5H, Ar—H);

$^{13}$C NMR (200 MHz, DMSO-d6) $\delta_C$ -7.39 ($SiCH_3$), -7.30 ($SiCH_3$), 15.41 (C($CH_3$)$_3$), 23.27 (C($CH_3$)$_3$), 67.06 (C-4')), 77.14 (C-$\overline{2}$')), 78.87 (C-3'), $\overline{1}$00.23 (C-1'), 126.58 (aroma-C), 127.09 (aroma-C), 131.40 (aroma-C), 163.18 (Bz-CO);

mass calcd for $C_{17}\overline{H}_{26}O_5Si_1Na_1$ $[M+Na]^+$ 361.1447, found 361.1452.

1α,2-di-O-tributyldimethylsilyl-L-threose (8a) and 1β,2-di-O-tributyldimethylsilyl-L-threose (8b)

To the solution of 7 (7.30 g, 21.6 mmol) and imidazole (2.94 g, 43.1 mmol) in 100 mL MeCN was added TBDMSCI (0.98 g, 23.8 mmol) at 0° C. in one portion. The reaction mixture was slowly warmed to room temperature and stirred overnight. The reaction mixture was concentrated. The residue was partitioned between $H_2O$ and EtOAc. The organic layer was washed with water and brine, and concentrated in vacuo. The residue was dissolved in MeOH saturated with ammonia (100 mL), and the reaction mixture was stirred at room temperature overnight. The mixture was concentrated, and the residue was purified by column chromatography (n-hexane:EtOAc, 20:1, 10:1) to give compound 8a (2.22 g, 1.40 mmol) as colorless oil in 42% yield and 8b (1.00 g, 1.40 mmol) as colorless oil in 19% yield which were characterized as follows.

Compound 8a:

$^1$H NMR (200 MHz, DMSO-d6) $\delta_H$ 0.06-0.08 (m, 12H, Si—$CH_3$), 0.87 (s, 18H, $CH_3$), 3.59-3.65 (m, C(2')H, 1H,), 3.87-3.99 (m, 3H, C4' $H_a$ C(3')H, C(4') $H_b$), 5.00 (d, J=1.1 Hz, C(1')H), 5.07-5.10 (m, 1H, OH);

$^{13}$C NMR (200 MHz, DMSO-d6) $\delta_C$ -5.14 ($Si\overline{CH_3}$), -4.92 ($SiCH_3$), -4.65 ($SiCH_3$), -4.38 ($SiCH_3$),$\overline{}$ 17.66 (C($\overline{CH_3}$)$_3$), 17.81 (C($C\overline{H_3}$)$_3$), 25.61 (C($\overline{CH_3}$)$_3$), 25.73 (C($\overline{CH_3}$)$_3$), 71.92 (C-$\overline{4}$'), 76.66 (C-2'), 85.$\overline{58}$ (C-3'), 103.91 ($\overline{C}$-1');

mass calcd for $C_{16}H_{36}O_4Si_2Na_1$ 371.2050, found 371.2059.

Compound 8b:

$^1$H NMR (200 MHz, DMSO-d6) $\delta_H$ 0.05 (s, 6H, SiCH$_3$), 0.06 (d, J$_1$=5.2 Hz, SiCH$_3$), 0.86 (s, 9H, CH$_3$), 0.87 (s, 9H, CH$_3$), 3.41 (dd, J$_1$=8.0 Hz, J$_2$=3.7 Hz, C(2')H); 3.81 (dd, J$_1$=5.2 Hz, J$_2$=3.7 Hz, C(3')H), 3.94-4.07 (m, 2H, C(4')H$_a$ C(4')H$_b$), 5.12-5.15 (m, 2H, OH, C(1')H);

$^1$H NMR 200 MHz (DMSO-d6+1D D$_2$O) $\delta_H$ 0.02 (s, 6H, SiCH$_3$), 0.04 (d, J$_2$=4.4 Hz, SiCH$_3$), 0.84 (s, 18H, CH$_3$), 3.39 (dd, J$_1$=7.7 Hz, J$_2$=3.6 Hz, C(2')H); 3.79 (dd, J$_1$=4.4 Hz, J$_2$=4.4 Hz, C(3')H), 3.92-4.07 (m, 2H, C(4')H$_a$ C(4')H$_b$) 5.10 (d, 1H, J$_2$=3.6 Hz, C(1')H);

$^{13}$C NMR (200 MHz, DMSO-d6) $\delta_C$ −4.95 (SiCH$_3$), −4.74 (SiCH$_3$), −4.67 (SiCH$_3$), 17.45 (C(CH$_3$)$_3$), 25.64 (C(CH$_3$)$_3$), 25.79 (C(CH$_3$)$_3$), 70.80 (C-4'), 74.17 (C-2'), 79.45 (C-3'), 97.11 (C-1');

mass calcd for C$_{16}$H$_{36}$O$_4$Si$_2$Na$_1$ 371.2050, found 371.2052.

1α,2-di-O-tributyldimethylsilyl-3-O-(diisopropylphosphonomethyl)-L-threose (9a) and 1β,2-di-O-tributyldimethylsilyl-3-O-(diisopropylphosphonomethyl)-L-threose (9b)

To a solution of 8a (3.41 g, 9.8 mmol) in dried THF (25 mL) was added sodium hydride (80% dispersion in mineral oil 0.56 mg, 19.6 mmol) at −78° C. Then the solution of the triflate of diisopropylphosphonomethanol (5.80 g, 19.6 mmol) in dried THF (10 mL) was dropwise added, and the reaction mixture was slowly warmed to room temperature. The reaction was quenched with sat. NaHCO$_3$ and concentrated. The residue was partitioned between H$_2$O and EtOAc. The organic layer was washed with water and brine, and concentrated in vacuo. The residue was purified by chromatography on a silica gel column (n-hexane/EtOAC=2:1) to afford 9a (4.75 g, 9.0 mmol, 92%) as colorless oil which was characterized as follows:

$^1$H NMR (200 MHz, DMSO-d6) $\delta_H$ 0.06-0.10 (m, 12H, SiCH$_3$), 0.86 (s, 9H, C(CH$_3$)$_3$), 0.87 (s, 9H, C(CH$_3$)$_3$), 1.22-1.26 (m, 12H, C(CH$_3$)$_2$), 3.75 (d, J=9.2 Hz, 2H, CH$_2$), 3.78 (d, J=9.2 Hz, 1H, C(4')H$_a$), 3.88-3.95 (m, 1H, C(3')H), 3.99 (s, 1H, C(2')H), 4.10 (dd, J$_1$=9.2 Hz, J$_2$=8.6 Hz, 1H, C(4')H$_b$), 4.52-4.68 (m, 2H, CH), 5.02 (s, 1H, C(1')H);

Exact mass for C$_{23}$H$_{52}$O$_7$P$_1$Si$_2$ [M+H]$^+$ Calcd. 527.2989, found 527.2988.

The synthesis of 9b started from 8b (2.00 g, 5.7 mmol) and followed the same procedure as for the synthesis of 9a from 8a resulting in a product (2.7 g, 5.1 mmol, yield 90%) as a colorless oil that which was characterized as follows:

$^1$H NMR (200 MHz, CDCl$_3$) $\delta_H$ 0.08-0.11 (m, 12H, SiCH$_3$), 0.93 (br s, 18H, C(CH$_3$)$_3$), 1.33 (d, J=6.2 Hz, 12H, C(CH$_3$)$_2$), 3.66-3.94 (m, 3H, C(4')H, PCH$_2$), 4.02-4.22 (m, 3H, C(2')H, C(3')H, C(4')H$_b$), 4.67-4.83 (m, 2H, CH(CH$_3$)$_2$), 5.13 (d, J=3.7 Hz, 1H, C(1')H);

$^1$H NMR (200 MHz, DMSO-d6) $\delta_H$ 0.06-0.93 (m, 12H, SiCH$_3$), 0.87 (s, 18H, C(CH$_3$)$_3$), 1.22-1.26 (m, 12H, C(CH$_3$)$_2$), 3.58-3.65 (m, 1H, C(4') H$_a$), 3.78 (d, J=9.2 Hz, PCH$_2$), 3.96-4.08 (m, 3H, C(2')H, C(3')H, C(4') H$_b$), 4.51-4.67 (m, 2H, CH(CH$_3$)$_2$), 5.15 (d, J=3.7 Hz, 1H, C(1')H);

$^{13}$C NMR (200 MHz, DMSO-d6) $\delta_C$ −5.22 (SiCH$_3$), −5.07 (SiCH$_3$), −4.58 (SiCH$_3$), 17.88 (C(CH$_3$)$_3$), 23.98 (OCH(CH$_3$)$_2$), 25.62 (C(CH$_3$)$_3$), 25.71 (C(CH$_3$)$_3$), 65.12 (d, J$_{P,C}$=173.6 Hz, PCH2), 68.38 (C-4'), 70.87 (OCH(CH$_3$)$_2$), 70.96 (OCH(CH$_3$)$_2$), 78.88 (C-2'), 85.68 (d, J$_{P,C}$=12.0 Hz, C-3'), 97.3 (C-1');

mass calcd for C$_{23}$H$_{52}$O$_7$P$_1$Si$_2$ [M+H]$^+$ 527.2989, found 527.2972.

1α,2-O-benzoyl-3-O-(diisopropylphosphonomethyl)-L-threose (10a) and 1β,2-O-benzoyl-3-O-(diisopropylphosphonomethyl)-L-threose (10b)

A solution of 9a (4.25 g, 8.1 mmol) in TFA-H$_2$O (3:1, 20 mL) was allowed to stand at room temperature for 2 hours. The reaction mixture was neutralized with saturated NaHCO$_3$ solution. Then the mixture was partitioned between the DCM (400 mL) and water (20 mL). The organic layer was washed with water and brine, dried over MgSO$_4$, and then concentrated in vacuo. The residue was purified by chromatography on silica gel (DCM:MeOH=20:1) to give 3-O-diisopropylphosphonomethyl-L-threose (2.20 g, 7.3 mmol) as a colorless amorphous solid in 92% yield.

To the solution of 3-O-(diisopropylphosphonomethyl)-L-threose (687 mg, 2.3 mmol) in 100 mL pyridine was added dropwise BzCl (0.67 g, 5.8 mmol) at 0° C. The reaction mixture was warmed to room temperature and stirred overnight. The reaction mixture was concentrated and coevaporated with 20 mL toluene two times in vacuo. The residue was partitioned between H$_2$O (20 mL) and EtOAc (150 mL). The organic layer was washed with water and brine, and concentrated in vacuo. The residue was purified by chromatography on a silica gel column (n-hexane/EtOAc=1:1) to afford 10a and 10b (1.0 g, 2.0 mmol) as colorless oils in 87% yield which were characterized as follows:

Compound 10a:

$^1$H NMR (200 MHz, DMSO-d6) $\delta_H$ 1.20-1.26 (m, 12H, C(CH$_3$)$_2$), 3.40-4.11 (m, 3H, PCH$_2$, C(4')H$_a$), 4.40-4.54 (m, 2H, C(3')H, C(4')H$_b$), 4.56-4.71 (m, 2H, OCH(CH$_3$)$_2$), 5.51 (s, 1H, C(2')H), 6.47 (s, 1H, C(1')H), 7.43-8.07 (m, 10H, Ar—H);

$^{13}$C NMR (200 MHz, DMSO-d6) $\delta_C$ 23.82 (CH$_3$), 64.45 (d, J=155.4 Hz, PCH$_2$), 70.59 (CH(CH$_3$)), 73.23 (C-4'), 80.12 (O-2'), 80.30 (C-2'), 99.78 (C-1'), 129.04 (aroma-C), 129.83 (aroma-C), 134.14 (aroma-C), 164.61 (Bz-CO), 165.07 (Bz-CO);

mass calcd for C$_{25}$H$_{31}$O$_9$P$_1$Na$_1$ [M+Na]$^+$ 529.1603, found 529.1601.

EXAMPLE 3

Preparation of Final Compounds 1-(N$^6$-benzoyladenin-9-yl)-2-O-benzoyl-3-O-(diisopropylphosphonomethyl)-L-threose (11)

To a mixture of 10a (425 mg, 0.83 mmol) and silylated N$^6$-benzoyladenine (401 mg, 1.6 mmol) in dry MeCN (30 mL) was dropwise added SnCl$_4$ (0.3 mL, 2.5 mmol) under N$_2$ at room temperature. The reaction mixture was stirred at room temperature for 4 to 5 hours. Then the reaction was quenched with saturated NaHCO$_3$. and concentrated. The residue was partitioned between H$_2$O (20 mL) and EtOAc (100 mL). The organic layer was washed with water and brine, and concentrated in vacuo. The residue was purified by chromatography on a silica gel column (DCM/MeOH=40:1) to afford 11 (431 mg, 0.69 mmol) as a colorless amorphous solid in 83% yield which was characterized as follows:

$^1$H NMR (500 MHz, CDCl$_3$) $\delta_H$ 1.31-1.36 (m, 12H, CH$_3$), 3.94 (dd, J$_1$=14.0 Hz, J$_2$=8.6 Hz, 1H, PCH$_a$), 4.01 (dd, J$_1$=14.0 Hz, J$_2$=8.6 Hz, 1H, PCH$_b$), 4.38 (dd, J$_1$=11.0 Hz, J$_2$=4.6 Hz, 1H, C(4')H$_a$), 4.50-4.52 (m, 2H, C(3')H, C(4') H$_b$), 4.73-4.80 (m, 2H, OCH), 5.08 (s, 1H, C(2')H), 6.56 (s, 1H, C(1')H), 7.48-7.65 (m, 6H, Ar—H), 8.02-8.08 (m, 4H, Ar—H), 8.50 (s, 1H, Adinie-C(8)-H), 8.82 (s, 1H, Adinie-C(2)-H), 9.07 (br s, 1H, NH);

$^{13}$C NMR (500 MHz, CDCl$_3$) δ$_C$ 23.97 (CH$_3$), 24.01 (CH$_3$), 24.03 (CH$_3$), 24.06 (CH$_3$), 65.36 (J$_{P,C}$=168.9 Hz, PCH$_2$), 71.45 (POOH), 71.51 (POCH), 73.55 (C-4')), 80.27 (0-2')), 83.74 (J$_{P,C}$=9.8 Hz, C-31 '), 87.86 (C-1')), 122.72 (A-C(5)), 127.80 (aroma-C), 128.65 (aroma-C), 128.67 (aroma-C), 128.86 (aroma-C), 129.93 (aroma-C), 132.31 (aroma-C), 133.99 (aroma-C), 141.98 (A-C(8)), 149.45 (A-C(6), 151.59 (A-C(4)), 152.93 (A-C(2)), 164.44 (OBz(CO)), 165.17 (NBz (CO));

mass calcd for C$_{30}$H$_{35}$N$_5$O$_8$P$_1$ [M+H]$^+$ 624.2223, found 624.2222.

1-(thymin-1-yl)-2-O-benzoyl-3-O-(diisopropylphosphonomethyl)-L-threose (12)

Thymine (0.34 g, 2.7 mmol), ammonia sulfate (10 mg, 0.07 mmol) and 6 mL of HMDS were added to dried flask. The mixture was refluxed overnight under nitrogen. HDMS was removed in vacuo. To the flask with residue was added the solution of compound 10a (0.92 g, 1.8 mmol) in 10 mL of dry MeCN followed by dropwise addition of SnCl$_4$ (640 μL 5.4 mmol) under N$_2$ at room temperature The reaction mixture was stirred for 4 hours. The reaction was quenched with sat. aq. NaHCO$_3$ and concentrated to a small volume. The residue was partitioned between H$_2$O (30 mL) and EtOAc (150 mL). The organic layer was washed with water and brine, and concentrated in vacuo. The residue was purified by chromatography on a silica gel column (n-hexane/EtOAc=1:1) to afford 12 (0.76 g, 1.4 mmol) as a colorless amorphous solid in 78% yield which was characterized as follows:

$^1$H NMR (200 MHz, CDCl$_3$) δ$_H$ 1.35 (d, J=6.2 Hz, 12H, CH$_3$), 1.99 (d, J=1.5 Hz, 3H, T-CH$_3$), 3.86-4.05 (m, 2H, PCH$_2$), 4.11-4.16 (m, 1H, C(4')H$_a$), 4.26 (br t, 1H, C(3')H), 4.40 (d, J=10.6 Hz, 1H, C(4') H$_b$), 4.70-4.86 (m, 2H, OCH(CH$_3$)$_2$), 5.38 (s, 1H, C(2')H), 6.29 (t, J=2.2 Hz, 1H, C(1')H), 7.43-7.66 (m, 4H, Ar—H, T-C(6)H), 8.02-8.07 (m, 2H, Ar—H), 9.13 (s, 1H, NH);

$^{13}$C NMR (200 MHz, CDCl$_3$) δ$_C$ 12.42 (T-CH$_3$), 23.83 (CH(CH$_3$)$_3$), 23.92 (CH(CH$_3$)$_3$), 64.48 (d, J$_{P,C}$=168.5 Hz, $\overline{P}$CH$_2$), 71.29 (CH($\overline{C}$H$_3$)$_3$), 71.45 (CH(CH$_3$)$_3$), 72.72 (C-4'), 80.28 ($\overline{C}$-2'), 83.70 (J$_{P,C}$=10.6 Hz, C-3'), 89.02 (C-1'), 111.39 (T-C(5)), 128.60 (aroma-C), 129.90 (aroma-C), 133.84 (T-C(6), 136.12 (aroma-C), 150.42 (T-C(2), 163.86 (T-C(4), 165.32 (Bz-CO);

mass calcd for C$_{23}$H$_{31}$N$_2$O$_9$P$_1$ [M+H]$^+$ 511.1845, found 511.1831.

1-(uracil-1-yl)-2-O-benzoyl-3-O-(diisopropylphosphonomethyl)-L-threose (13)

Uracil (0.81 g, 7.2 mmol), ammonia sulfate (10 mg, 0.07 mmol) and 20 mL of HMDS were added to dried flask. The mixture was refluxed overnight under nitrogen. HDMS was removed in vacuo. To the residue was added the solution of compound 10a (2.43 g, 4.8 mmol) in 50 mL of dry MeCN followed by a dropwise addition of SnCl$_4$ (1.7 mL, 14.4 mmol). The reaction mixture was stirred for 4 hours. The reaction was quenched with sat. aq. NaHCO$_3$ and concentrated to small volume. The residue was partitioned between H$_2$O (30 mL) and EtOAc (100 mL). The organic layer was washed with water and brine, and concentrated in vacuo. The residue was purified by chromatography on a silica gel column (DCM/MeOH=25:1) to afford 13 (2.09 g, 4.2 mmol) as a colorless amorphous solid in 84% which was characterized as follows:

$^1$H NMR (500 MHz, DMSO-d6) δ$_H$ 1.23-1.26 (m, 12H, CH$_3$), 3.97 (d, J=9.0 Hz, 2H, PCH$_2$), 4.16 (dd, J$_1$=10.7 Hz, J$_2$=4.2 Hz, 1H, C(4')H$_a$), 4.36 (d, J=10.7 Hz, 1H, C(4')H$_b$), 4.39-4.40 (m, 1H, C(3')H), 4.58-4.64 (m, 2H, OCH(CH$_3$)$_2$), 5.41 (s, 1H, C(2')H), 5.61 (d, J=8.1 Hz, 1H, U-C(5)H), 6.02 (d, J=2.0 Hz, 1H, C(1')H), 7.55-7.60 (m, 2H, Ar—H), 7.63 (d, J=8.1 Hz, 1H, U-C(5)H), 7.70-7.73 (m, 1H, Ar—H), 8.02-8.04 (m, 2H, Ar—H), 11.4 (s, 1H, NH);

$^{13}$C NMR (500 MHz, DMSO-d6) δ$_C$ 23.74 (CH(CH$_3$)$_3$), 23.84 (CH(CH$_3$)$_3$), 63.10 (d, J$_{P,C}$=168.5 Hz, $\overline{P}$CH$_2$), 70.53 (CH($\overline{C}$H$_3$)$_3$), 72.32 (C-4'), 79.83 (C-2'), 82.78 (C-3'), $\overline{89}$.06 (C-1'), 101.91 (U-C(5), 128.95 (aroma-C), 129.63 (aroma-C), 134.07 (aroma-C), 140.72 (U-C(6), 150.39 (U-C(2)), 163.19 (U-C(4), 164.73 (Bz-CO);

mass calcd for C$_{22}$H$_{29}$N$_2$O$_9$P$_1$Na$_1$ [M+Na]$^+$ 519.1508, found 519.1506.

1-(N$^4$-acetylcytosin-1-yl)-2-O-benzoyl-3-O-(diisopropylphosphonomethyl)-L-threose (14)

N$^4$-Acetylcytosine (0.41 g, 2.7 mmol) and ammonia sulfate (10 mg, 0.07 mmol) and 6 mL of HMDS were added to dried flask. The mixture was refluxed overnight under nitrogen. HDMS was removed in vacuo. To the residue was added the solution of compound 10a (0.92 g, 1.8 mmol) in 10 mL of dry MeCN followed by a dropwise addition of stannic chloride (640 μL 5.4 mmol). The reaction mixture was stirred for 4 hours. The reaction was quenched with sat. aq. NaHCO$_3$ and concentrated to small volume. The residue was partitioned between H$_2$O (30 mL) and EtOAc (150 mL). The organic layer was washed with water and brine, and concentrated in vacuo. The residue was purified by chromatography on a silica gel column (n-hexane/EtOAc=2:1) to afford 14 (0.51 g, 0.94 mmol) as a colorless amorphous solid in 52% yield which was characterized as follows:

$^1$H NMR (200 MHz, DMSO-d6) δ$_H$ 1.17-1.23 (m, 12H, CH(CH$_3$)$_2$), 2.10 (s, 3H, CH$_3$), 3.80-4.00 (m, 2H, PCH$_2$), 4.24-4.36 (m, 2H, C(4')H$_a$, C(3')H), 4.48-4.63 (m, 3H, C(4') H$_b$, OCH(CH$_3$)$_2$), 5.44 (s, 1H, C(2')H), 6.04 (s, 1H, C(1')H), 7.27 (d, J=7.7 Hz, 1H, C-C(5)H), 7.54-7.77 (m, 3H, Ar—H), 8.03-8.07 (m, 3H, Ar$_o$—H, C-C(6)H), 10.95 (s, 1H, NH);

$^{13}$C NMR (200 MHz, DMSO-d6) δ$_C$ 23.76 (CH(CH$_3$)$_3$), 24.39 (Ac-CH$_3$), 63.77 (d, J$_{P,C}$=166.4 Hz, PCH$_2$$\overline{)}$, 70.44 (CH(CH$_3$)$_3$), 70.59 (CH($\overline{C}$H$_3$)$_3$), 73.56 (C-4'), 79.75 ($\overline{C}$-3') 82.83 (d, J$_{P,C}$=13.7 Hz, C-3'), 90.74 (C-1'), 94.74 (C-C(5), 128.86 (aroma-C), 129.14 (aroma-C), 134.07 (aroma-C), 129.77 (aroma-C), 134.23 (aroma-C), 145.40 (C-C(6), 154.69 (C-C(2)), 162.95 (Bz-CO), 164.77 (C-C(4)); 171.26 (Ac-00);

mass calcd for C$_{24}$H$_{33}$N$_3$O$_9$P$_1$ [M+H]$^+$ 538.1954, found 538.1956.

1-(adenin-9-yl)-3-O-(diisopropylphosphonomethyl)-L-threose (15)

A solution of 11 (431 mg, 0.80 mmol) in MeOH saturated with ammonia (100 mL) was stirred at room temperature overnight. The mixture was concentrated, and the residue was purified by column chromatography (CH$_2$Cl$_2$:MeOH=9:1) to give compound 15 (278 mg, 0.67 mmol) as a white powder in 84% yield which was characterized as follows:

¹H NMR (500 MHz, DMSO-d6): δ$_H$ 1.21-1.26 (m, 12H, CH$_3$), 3.85-3.94 (m, 2H, PCH$_2$), 4.10-4.13 (m, 2H, C(4') H$_a$, C(3')H), 4.24-4.27 (m, 1H, C(4') H$_b$), 4.57-4.63 (m, 3H, CH(CH)$_3$, C(2')H), 5.93 (d, J=2.1 Hz, 1H, C(1')H), 6.05 (br s, 1H, OH), 7.24 (s, 2H, NH$_2$), 8.15 (s, 1H, C(2)H), 8.18 (s, 1H, C(8)H);

¹³C NMR (200 MHz, DMSO-d6): δ$_C$ 23.82 (CH$_3$), 63.5 (J$_{P,C}$=164.6 Hz, PCH$_2$), 70.41 (OCH), 70.53 (OCH), 71.65 (C-4'), 78.27 (C-2'), 85.62 (J$_{P,C}$=13.6 Hz, C-3'), 89.53 (C-1'), 118.79 (A-C(5), 139.39 (A-C(8)), 149.47 (A-C(6), 152.90 (A-C(4)), 156.24 (A-C(2));

mass calcd for C$_{16}$H$_{27}$N$_5$O$_6$P$_1$ [M+H]$^+$ 416.1699, found 416.1681.

1-(thymin-1-yl)-3-O-(diisopropylphosphonomethyl)-L-threose (16)

A solution of 12 (715 mg, 1.7 mmol) in MeOH saturated with ammonia (100 mL) was stirred at room temperature overnight. The mixture was concentrated, and the residue was purified by column chromatography (CH$_2$Cl$_2$:MeOH=10:1) to give compound 16 (515 mg, 1.2 mmol) as a white powder in 71% yield which was characterized as follows:

¹H NMR (200 MHz, CDCl$_3$) δ$_H$ 1.27-1.33 (m, 12H, CH$_3$), 1.93 (d, J=1.7 Hz, 3H, T-CH$_3$), 3.75 (d, J=8.8 Hz, 2H, PCH$_2$), 4.13 (br t, 1H, C(3')H), 4.24-4.31 (m, 2H, C(4') H$_2$), 4.38 (s, 1H, C(2')H), 4.61-4.80 (m, 2H, OCH (CH$_3$)$_2$), 5.81 (s, 1H, C(1')H), 7.41 (d, J=1.46 Hz, T-C (6)H), 10.27 (br s, 1H, NH);

¹³C NMR (200 MHz, CDCl$_3$) δ$_c$ 2.42 (T-CH$_3$), 23.89 (CH(CH$_3$)$_3$), 64.46 (d, J$_{P,C}$=168.5 Hz, PCH$_2$), 71.26 (CH(CH$_3$)$_3$), 73.54 (C-4'), 78.94 (C-2'), 85.33 (d, J$_{P,C}$=10.6 Hz, C-3'), 93.12 (C-1'), 110.12 (T-C(5)), 136.40 (T-C(6), 151.08 (T-C(2)), 164.56 (T-C(4));

mass calcd for C$_{16}$H$_{28}$N$_2$O$_8$P$_1$ [M+H]$^+$ 407.1583, found 407.1568.

1-(uracil-1-yl)-3-O-(diisopropylphosphonomethyl)-L-threose (17)

A solution of 13 (2.03 g, 4.0 mmol) in MeOH saturated with ammonia (300 mL) was stirred at room temperature overnight. The mixture was concentrated, and the residue was purified by column chromatography (CH$_2$Cl$_2$:MeOH=20:1) to give compound 17 (1.52 g, 3.8 mmol) as a white powder in 96% yield which was characterized as follows:

¹H NMR (200 MHz, DMSO-d6): δ$_H$ 1.19-1.25 (m, 12H, CH$_3$), 3.78 (dd, J$_1$=13.9 Hz, J$_2$=9.2 Hz, PCH$_a$) 3.85 (dd, J$_1$=13.9 Hz, J$_2$=9.2 Hz, PCH$_b$), 3.98-4.28 (m, 4H, C(2') H, C(3')H, C(4')H$_2$), 4.50-4.66 (m, 2H, CH(CH$_3$), 5.50 (d, J=8.0 Hz, U-C(5)H), 5.66 (d, J=1.5 Hz, OH), 5.93 (d, J=4.4 Hz, C(1')H), 7.54 (d, J=8.0 Hz, U-C(6)H);

¹³C NMR (200 MHz, DMSO-d6) δ$_c$ 23.70 (CH(CH$_3$)$_3$), 23.79 (CH(CH$_3$)$_3$), 63.29 (d, J$_{P,C}$=166.3 Hz, PCH$_2$), 70.34 (CH(CH$_3$)$_3$), 70.47 (CH(CH$_3$)$_3$), 72.29 (C-4'), 77.84 (C-2'), 85.23 (J$_{P,C}$=10.7 Hz, C-3'), 91.68 (C-1'), 101.12 (U-C(5)), 141.12 (U-C(6), 150.72 (U-C(2)), 163.46 (C-C(4));

mass calcd for C$_{15}$H$_{26}$N$_2$O$_8$P$_1$ [M+H]$^+$ 393.1427, found 393.1425.

1-(cytosin-1-yl)-3-O-(diisopropylphosphonomethyl)-L-threose (18)

A solution of 14 (450 mg, 0.84 mmol) in MeOH saturated with ammonia (100 mL) was stirred at room temperature overnight. The mixture was concentrated, and the residue was purified by column chromatography (CH$_2$Cl$_2$:MeOH=20:1) to give compound 18 (281 mg, 0.72 mmol) as a white powder in 86% yield which was characterized as follows:

¹H NMR (200 MHz, DMSO-d6) δ$_H$ 1.18-1.25 (m, 12H, CH$_3$), 3.72 (dd, J$_1$=13.6 Hz, J$_2$=8.8 Hz, PCH$_a$) 3.84 (dd, J$_1$=13.6 Hz, J$_2$=8.8 Hz, PCH$_b$), 3.95-4.05 (m, 3H, C(2') H, C(3')H, C(4')H$_a$), 4.25 (d, J=9.5 Hz, C(4')H$_b$), 4.48-4.64 (m, 2H, CH(CH$_3$), 5.65 (d, J=7.6 Hz, C-C(5)H), 5.70 (d, J=1.5 Hz, OH), 5.85 (d, J=15.4 Hz, C(1')H), 7.04 (br s, NH$_a$), 7.14 (br s, NH$_b$), 7.50 (d, J=7.6 Hz, C-C(6) H);

¹³C NMR (200 MHz, DMSO-d6): δ$_c$ 23.68 (CH(CH$_3$)$_3$), 23.78 (CH(CH$_3$)$_3$), 64.46 (d, J$_{P,C}$=164.8 Hz, PCH$_2$), 70.30 (CH(CH$_3$)$_3$), 70.42 (CH(CH$_3$)$_3$), 72.00 (C-4'), 78.19 (C-2'), 85.66 (d, J$_{P,C}$=12.2 Hz, C-3'), 92.30 (C-1'), 93.46 (C-C(5)), 141.63 (C-C(6), 155.47 (C-C(2)), 165.94 (C-C(4));

mass calcd for C$_{15}$H$_{27}$N$_3$O$_7$P$_1$ [M+H]$^+$ 392.1586, found 392.1577.

1-(adenin-9-yl)-2-deoxy-3-O-(diisopropylphosphonomethyl)-L-threose (19)

To a solution of phenyl(chloro)thiocarbonate (0.25 mL, 1.8 mmol) and DMAP (426 mg, 3.5 mmol) in dried MeCN (25 mL) was added compound 15 (483 mg, 1.2 mmol) at room temperature. The reaction mixture was stirred for 12 hours. The mixture was concentrated, and the residue was purified by column chromatography (CH$_2$Cl$_2$:MeOH/10:1) to give 1-(adenin-9-yl)-2-O-phenoxythiocarbonyl-3-O-diisopropylphosphonomethyl-L-threose as a colorless oil. To the solution of 1-(adenin-9-yl)-2-O-phenoxythiocarbonyl-3-O-diisopropylphosphonomethyl-L-threose in dried 50 mL of toluene was added tributylinhydride (339 µL, 1.2 mmol) and AIBN (48 mg, 0.3 mmol). The reaction mixture was refluxed for 6 hours and concentrated in vacuo. The residue was purified by column chromatography (CH$_2$Cl$_2$:MeOH/10:1) to give compound 19 (110 mg, 0.27 mmol) as a colorless oil in 23% yield which was characterized as follows:

¹H NMR (200 MHz, CDCl$_3$) δ$_H$ 1.27-1.34 (m, 12H, CH$_3$), 2.54-2.75 (m, 2H, C(2)H$_2$), 3.62-3.82 (m, 2H, PCH$_2$), 4.04 (dd, J$_1$=10.3 Hz, J$_2$=4.0 Hz, 1H, C(4')H$_a$), 4.35 (d, J=10.3 Hz, C(4')H$_b$), 4.43-4.48 (m, 1H, C(3')H), 4.62-4.84 (m, 2H, OCH(CH$_3$)$_2$), 6.21 (br s, 2H, NH$_2$), 6.47 (dd, J$_1$=7.2 Hz, J$_2$=2.7 Hz, 1H, C(1')H), 8.31 (s, 1H, A-C(2)H), 8.33 (s, 1H, A-C(8)H);

¹³C NMR (200 MHz, CDCl$_3$) δ$_C$ 23.89 (CH(CH$_3$)$_3$), 38.05 (C-2'), 64.10 (d, J$_{P,C}$=169.4 Hz, PCH$_2$), 71.31 (CH(CH$_3$)$_3$), 71.46 (CH(CH$_3$)$_3$), 73.68 (C-4'), 80.49 (d, J$_{P,C}$=10.7 Hz, C-3'), 83.42 (C-1'), 119.50 (A-C(5)), 136.63 (A-C(8)), 149.73 (A-C(6), 153.07 (A-C(4)), 155.62 (A-C(2));

mass calcd for C$_{16}$H$_{27}$N$_5$O$_5$P$_1$ [M+H]$^+$ 400.1750, found 400.1740.

1-(thymin-1-yl)-2-deoxy-3-O-(diisopropylphosphonomethyl)-L-threose (20)

This compound was prepared as described for 19, using 16 (450 mg, 1.1 mmol) as a starting material. Column chromatographic purification (CH$_2$Cl$_2$:MeOH=10:1) gave compound 20 (275 mg, 0.70 mmol) as a colorless oil in 64% yield which was characterized as follows:

¹H NMR (200 MHz, CDCl$_3$) δ$_H$ 1.31 (d, 6H, CH$_3$), 1.34 (d, 6H, CH$_3$), 1.97 (d, J=1.1 Hz, 3H, T-CH$_3$), 2.16 (d, J=15.0 Hz, 1H, C(2') H$_a$), 2.46-2.62 (m, 1H, C(2') H$_a$), 3.72 (d, J=9.2 Hz, 2H, PCH$_2$), 3.84 (dd, J$_1$=10.6 Hz, J$_2$=3.7 Hz,

1H, C(4') H$_a$), 4.29-4.37 (m, 2H, C(4') H$_b$, C(3')H), 4.66-4.84 (m, 2H, OCH(CH$_3$)$_2$), 6.24 (dd, J$_1$=8.0 Hz, J$_2$=2.6 Hz, 1H, C(1')H), 7.55 (d, J=1.1 Hz, 1H, T-C(6) H), 8.48 (s, 1H, NH);
$^{13}$C NMR (200 MHz, CDCl$_3$) δ$_C$ 12.45 (T-CH$_3$), 23.92 (CH(CH$_3$)$_3$), 38.27 (C-2'), 63.99 (d, J=169.2 Hz, PCH$_2$), 71.26 (CH(CH$_3$)$_3$, 73.36 (C-4'), 80.23 (d, J=10.5 Hz, C-3'), 84.83 (C-1'), 110.72 (T-C(5)), 136.55 (T-C(6)), 150.57 (T-C(2)), 163.80 (T-C(4));
mass calcd for C$_{16}$H$_{27}$N$_{12}$O$_7$P$_1$Na$_1$ [M+Na]$^+$ 413.1454, found 413.1447.

1-(uracil-1-yl)-2-deoxy-3-O-(diisopropylphosphonomethyl)-L-threose (21)

This compound was prepared as described for 19, using 17 (1.1 g, 2.8 mmol) as a starting material. Column chromatographic purification (CH$_2$Cl$_2$:MeOH=40:1) gave compound 21 (500 mg, 1.3 mmol) as a colorless oil, in 46% yield, which was characterized as follows:
$^1$H NMR (200 MHz, CDCl$_3$) δ$_H$ 1.29-1.34 (m, 12H, CH$_3$), 2.21 (d, J=15.4, 1H, C(2')H$_a$), 2.44-2.60 (m, 1H, C(2') H$_b$), 3.69 (d, J=9.2 Hz, 2H, PCH$_2$), 3.86 (dd, J$_1$=10.6 Hz, J$_2$=3.3 Hz, 1H, C(4')H$_a$), 4.30-4.38 (m, 2H, C(4')H$_b$, C(3')H), 4.65-4.81 (m, 2H, OCH(CH$_3$)$_2$), 5.74 (d, J=8.1 Hz, 1H, U-C(5)H), 6.21 (dd, =8.0 Hz, J$_2$=2.0 Hz, 1H, C(1')H), 7.71 (d, J=8.0 Hz, 1H, U-C(6)H), 9.16 (s, 1H, NH);
$^{13}$C NMR (200 MHz, CDCl$_3$) δ$_P$ 23.98 (CH(CH$_3$)$_3$)), 38.42 (C-2')), 63.86 (d, J$_{P,C}$=170.7 Hz, PCH$_2$), 71.26 (CH(CH$_3$)$_3$), 71.36 (CH(CH$_3$)$_3$), 73.94 (C-4'), 80.11 (d, J$_{P,C}$=11.2 Hz, C-3'), 85.44 (C-1'), 101.95 (U-C(5)), 140.92 (U-C(6)), 150.63 (U-C(2)), 163.47 (U-C(4));
mass calcd for C$_{15}$H$_{26}$N$_2$O$_7$P$_1$ [M+H]$^+$ 377.1478, found 377.1479.

1-(cytosin-1-yl)-2-deoxy-3-O-(diisopropylphosphonomethyl)-L-threose (22)

To the solution of 1,2,4-triazole (662 mg, 9.6 mmol) in 15 mL pyridine was added phosphorousoxychloride (223 μL, 2.4 mmol) at room temperature. The mixture was stirred for 10 minutes. Then the solution of 21 (289 mg, 0.80 mmol) was added to the mixture. The reaction mixture was stirred for 4 hours. Then ammonia gas was bubbled in to the reaction mixture for 1-3 hours and the reaction mixture was concentrated in vacuo. The residue was purified by column chromatography (CH$_2$Cl$_2$:MeOH=12:1) to give compound 22 (220 mg, 0.58 mmol) as a colorless foam, in 73% yield, which was characterized as follows:
$^1$H NMR (200 MHz, CDCl$_3$) δ$_H$ 1.22-1.30 (m, 12H, CH$_3$), 2.27 (d, J=15.0, 1H, C(2')H$_a$), 2.41-2.55 (m, 1H, C(2') H$_b$), 3.63 (d, J=9.5 Hz, 2H, PCH$_2$), 3.91 (dd, J$_1$=10.3, J$_2$=3.5, 1H, C(4')H$_a$), 4.22-4.36 (m, 2H, C(4')H$_b$, C(3') H), 4.56-4.76 (m, 2H, OCH(CH$_3$)$_2$), 5.77 (d, J=7.3 Hz, 1H, C-C(5)H), 6.17 (dd, J$_1$=7.3, J$_2$=1.8, 1H, C(1')H), 7.67 (d, J=7.3 Hz, 1H, C-C(6)H), 8.18 (s, 2H, NH$_2$);
$^{13}$C NMR (200 MHz, CDCl$_3$) δ$_C$ 23.80 (CH(CH$_3$)$_3$), 38.46 (C-2'), 63.66 (d, J$_{P,C}$=172.2 Hz, PCH$_2$), 71.48 (CH(CH$_3$)$_3$), 71.60 (CH(CH$_3$)$_3$), 71.75 (CH(CH$_3$)$_3$), 74.12 (C-4'), 80.40 (d, J$_{P,C}$=11.2 Hz, C-3'), 86.68 (C-1'), 94.21 (C-C(5)), 141.9 (C-C(6)), 156.58 (C-C(2)), 165.83 (C-C(1));
mass calcd for C$_{15}$H$_{26}$N$_3$O$_6$P$_1$Na$_1$ [M+H]$^+$ 376.1637, found 376.1638.

1-(adenin-9-yl)-3-O-(phosphonomethyl)-L-threose Sodium Salt (3a)

To a solution of 15 (220 mg, 0.55 mmol) and Et$_3$N (1 at.) in DCM (9 mL) was added bromotrimethylsilane (290 μL, 2.2 mmol) at room temperature. The reaction mixture was stirred for 48 hours. The reaction was quenched with 1.0 M TEAB solution. The mixture was concentrated, and the residue was purified by column chromatography (CH$_2$Cl$_2$:MeOH/2:1, 1:1, 1:2) to give crude title compound. Purification using sephadex-DEAE A-25 with gradient TEAB solution from 0.01 M to 0.5 M and ion exchanges by the Dowex-Na+ resin offered 3a (96 mg, 0.25 mmol) as a colorless solid, in 45% yield, which was characterized as follows:
$^1$H NMR (500 MHz, D$_2$O) δ$_H$ 3.54-3.62 (m, 2H, PCH$_2$), 4.32-4.39 (m, 3H, C(4')H$_2$, C(3')H), 4.82 (dd, J$_1$=2.4 Hz, J$_2$=2.0 Hz, 1H, C(2')H), 6.09 (d, J=2.4 Hz, 1H, C(1')H), 8.23 (s, 1H, A-C(8)H), 8.45 (s, 1H, A-C(2)H);
$^{13}$C NMR (500 MHz, D$_2$O): δ$_C$ 70.1 (d, J$_{P,C}$=164.6 Hz, PCH$_2$), 75.38 (C-4'), 80.70 (C-2'), 87.56 (J$_{P,C}$=9.8 Hz, C-3'), 91.93 (C-1'), 121.21 (A-C(5), 143.74 (A-C(8)), 151.49 (A-C(6), 155.48 (A-C(4), 158.30 (A-C(2));
$^{31}$P NMR (500 MHz, D$_2$O). δ$_p$ 13.64;
mass calcd for C$_{10}$H$_{13}$N$_5$O$_6$P$_1$ [M−H]$^-$ 330.0603, found 330.0602.

1-(thymin-9-yl)-3-O-(phosphonomethyl)-L-threose sodium salt (3b)

This compound was prepared as described for 3a, using 16 (220 mg, 0.58 mmol) as starting material. Compound 3b (90 mg, 0.24 mmol) was obtained as a colorless solid in 42% yield, which was characterized as follows:
$^1$H NMR (500 MHz, D$_2$O) δ$_H$ 1.89 (s, 3H, T-CH$_3$), 3.60-3.68 (m, 2H, PCH$_2$), 4.16 (d, J=4.1 Hz, 1H, C(3')H), 4.24 (dd, J$_1$=10.7 Hz, J$_2$=4.1 Hz, 1H, C(4')H$_a$), 4.42 (d, J=10.7 Hz, 1H, C(4')H$_b$), 4.45 (s, 1H, C(2')H), 5.85 (d, J=1.2 Hz, 1H, C(1')H), 7.59-7.60 (m, 1H, T-C(6)H);
$^{13}$C NMR (500 MHz, D$_2$O): δ$_C$ 14.28 (T-CH$_3$), 67.95 (d, J$_{P,C}$=157.2 Hz, PCH$_2$), 75.78 (C-4'), 80.17 (C-2'), 87.27 (d, J$_{P,C}$=11.7 Hz, C-3'), 94.22 (C-1'), 113.36 (T-C(5)), 140.66 (T-C(6)), 154.30 (T-C(2)), 169.39 (T-C(4));
$^{31}$P NMR (500 MHz, D$_2$O) δ$_P$ 15.68;
mass calcd for C$_{10}$H$_{14}$N$_2$O$_8$P$_1$ [M−H]$^-$ 321.0488, found 321.0474.

1-(uracil-1-yl)-3-O-(phosphonomethyl)-L-threose sodium salt (3c)

This compound was prepared as described for 3a using 17 (200 mg, 0.53 mmol) as a starting material and TBMSBr (200 mL, 2.1 mmol). Compound 3c (93 mg, 0.26 mmol) was obtained as a colorless solid, in 49% yield, which was characterized as follows:
$^1$H NMR (500 MHz, D$_2$O) δ$_H$ 3.58-3.67 (m, 2H, PCH$_2$), 4.16 (d, J=3.3 Hz, 1H, C(3')H), 4.26 (dd, J$_1$=10.7 Hz, J$_2$=3.9 Hz, 1H, C(4')H$_a$), 4.45 (d, J=10.7 Hz, 1H, C(4') H$_b$), 4.47 (s, 1H, C(2')H), 5.85 (d, J=8.0 Hz, 1H, U-C(5) H), 5.85 (s, 1H, C(1')H), 7.80 (d, J=8.1 Hz, 1H, U-C(6) H);
$^{13}$C NMR (500 MHz, D$_2$O) δ$_C$ 67.98 (d, J=156.2 Hz, PCH$_2$), 76.22 (C-4'), 80.09 (C-2'), 87.15 (d, J=11.7 Hz, C-3'), 94.63 (C-1'), 104.09 (U-C(5)), 145.23 (U-C(6)), 154.26 (U-C(2)), 169.22 (U-C(4));
$^{31}$P NMR (500 MHz, D$_2$O) δ 15.37;

mass calcd for $C_9H_{12}N_2O_8P_1$ [M–H]⁻ 307.0331, found 307.0325.

1-(cytosin-1-yl)-3-O-(phosphonomethyl)-L-threose sodium salt (3d)

This compound was prepared as described for 3a, using 18 (150 mg, 0.38 mmol) as a starting material. Compound 3d (58 mg, 0.16 mmol) was obtained as a colorless solid, in 43% yield, which was characterized as follows:
¹H NMR (500 MHz, D₂O) $\delta_H$ 3.53-3.62 (m, 2H, PCH₂), 4.15 (d, J=3.7 Hz, 1H, C(3')H), 4.27 (dd, J₁=10.7 Hz, J₂=3.7 Hz, 1H, C(4')H$_a$), 4.42 (s, 1H, C(2')H), 4.44 (d, J=10.7 Hz, 1H, C(4')H$_b$), 5.86 (s, 1H, C(1')H), 6.01 (d, J=7.6 Hz, C-C(5)H), 7.77 (d, J=7.6 Hz, C-C(6)H);
¹³C NMR (500 MHz, D₂O) $\delta_C$ 68.0 (d, $J_{P,C}$=156.2 Hz, PCH₂), 76.17 (C-4')), 80.13 (C-2')), 87.27 (d, $J_{P,C}$=11.8 Hz, C-3')), 95.16 (C-1'), 98.23 (C-C(5)), 145.04 (C-C(6)), 160.06 (C-C(2)), 168.84 (C-C(4));
³¹P NMR (500 MHz, D₂O) $\delta_P$ 15.28;
mass calcd for $C_9H_{13}N_3O_7P_1$ [M–H]⁻ 306.0491, found 306.0481.

1-(adenin-1-yl)-2-deoxy-3-O-(phosphonomethyl)-L-threose sodium salt (3e)

This compound was prepared as described for 3a, using 19 (70 mg, 0.23 mmol) as a starting material. Compound 3e (38 mg, 0.11 mmol) was obtained as a colorless solid, in 43% yield, which was characterized as follows:
¹H NMR (500 MHz, D₂O, 60° C.) $\delta_H$ 2.63 (dd, J₁=15.5 Hz, J₂=1.3 Hz, 1H, C(2')H$_a$), 2.75-2.81 (m, 1H, C(2')H$_b$), 3.55-3.64 (m, 2H, PCH₂), 4.09 (dd, J₁=10.0 Hz, J₂=4.0 Hz, 1H, C(4')H$_a$), 4.33 (d, J=10.0 Hz, 1H, C(4')H$_b$), 4.51 (dd, J₁=5.5 Hz, J₂=4.5 Hz, 1H, C(3')H), 6.39 (dd, J₁=8.0 Hz, J₂=2.0 Hz, 1H, C(1')H), 8.22 (s, 1H, C(2)H), 8.49 (s, 1H, C(8)H);
¹³C NMR (500 MHz, D₂O) $\delta_C$ 39.78 (0-2'), 68.34 (d, $J_{P,C}$=155.2 Hz, PCH₂), 76.53 (0-4'), 82.79 (d, $J_{P,C}$=11.9 Hz, C-3'), 86.32 (C-1'), 121.13 (A-C(5)), 143.89 (A-C(8)), 151.33 (A-C(6)), 155.25 (A-C(4)), 158.18 (A-C(2));
³¹P NMR (500 MHz, D₂O) $\delta_p$ 154.46;
mass calcd for $C_{10}H_{13}N_5O_5P_1$ [M–H]⁻ 314.0654, found 314.0632.

1-(thymin-1-yl)-2-deoxy-3-O-(phosphonomethyl)-L-threose sodium salt (3f)

To a solution of 20 (260 mg, 0.67 mmol) and Et₃N (1 mL) in DCM (25 mL) was added iodotrimethysilane (0.73 mL, 5.36 mmol) at 0° C. The reaction mixture was stirred for 2 hours. The reaction was quenched with 1.0 M TEAB solution. The mixture was concentrated, and the residue was purified by column chromatography (CH₂Cl₂:MeOH/2:1, 1:1, 1:2) to give crude 3f. Purification using sephadex-DEAE A-25 with gradient TEAB solution from 0.01 M to 0.5 M and ion exchanges by the Dowex-Na⁺ resin offered 3f (95 mg, 0.27 mmol) as a colorless solid, in 40% yield, which was characterized as follows:
¹H NMR (500 MHz, D₂O) $\delta\delta_H$ 1.91 (s, 3H, T-CH₃), 2.29 (d, J=15.4 Hz, 1H, C(2')H$_a$), 2.58-2.64 (m, 1H, C(2')H$_a$), 3.57-3.65 (m, 2H, PCH₂), 3.95 (dd, J₁=10.5 Hz, J₂=3.4 Hz, 1H, C(4')H$_a$), 4.38-4.41 (m, 2H, C(4')H$_b$, C(3')H), 6.20 (dd, J₁=8.3 Hz, J₂=2.4 Hz, 1H, C(1')H), 7.78 (d, J=1.0 Hz, 1H, T-C(6)H);
¹³C NMR (500 MHz, D₂O) $\delta_C$ 14.50 (T-CH₃), 39.62 (0-2'), 67.81 (d, J=158.1 Hz, PCH₂), 76.63 (C-4'), 82.66 (d, J=11.3 Hz, C-3'), 88.41 (C-1'), 113.94 (T-(C(5)), 141.32 (T-(C(6)), 154.68 (T-(C(2)), 169.51 (T-C(4));
³¹P NMR (500 MHz, D₂O) $\delta_P$ 16.02;
mass calcd for $C_{10}H_{14}N_2O_7P_1$ [M–H]⁻ 305.0538, found 305.0537.

1-(uracil-1-yl)-2-deoxy-3-O-(phosphonomethyl)-L-threose sodium salt (3g)

This compound was prepared as described for 3f, using 21 (154 mg, 0.41 mmol) as a starting material and iodotrimethysilane (0.47 mL, 3.3 mmol). Compound 3g (50 mg, 0.14 mmol) was obtained as a colorless solid, in 34% yield, which was characterized as follows:
¹H NMR (500 MHz, D₂O) $\delta_H$ 2.31-2.35 (m, 1H, C(2')H$_a$), 2.57-2.62 (m, 1H, C(2')H$_b$), 3.54-3.62 (m, 2H, PCH₂), 3.97 (dd, J₁=10.5 Hz, J₂=3.7 Hz, 1H, C(4')H$_a$), 4.38-4.40 (m, 1H, C(3')H), 4.42 (dd, J₁=10.5 Hz, J₂=2.0 Hz, 1H, C(4')H$_b$), 5.88 (d, J=8.3 Hz, 1H, U-C(5)H), 6.21 (dd, J₁=8.2 Hz, J₂=2.0 Hz, 1H, C(1')H), 7.99 (d, J=8.2 Hz, 1H, U-C(6)H);
¹³C NMR (500 MHz, D₂O) $\delta_C$ 39.46 (C-2')), 67.56 (d, J=156.9 Hz, PCH₂), 76.77 (C-4'), 82.31 (d, J=13.8 Hz, C-3'), 88.57 (C-1'), 101.45 (U-C(5)), 145.81 (U-C(6), 169.23 (U-C(4));
³¹P NMR (500 MHz, D₂O) $\delta_P$ 15.72;
mass calcd for $C_9H_{12}N_2O_7P_1$ [M–H]⁻ 291.0382, found 291.0391.

1-(cytosin-1-yl)-2-deoxy-3-O-(phosphonomethyl)-L-threose sodium salt (3h)

This compound was prepared as described for 3f, using 22 (200 mg, 0.53 mmol) as a starting material and iodotrimethysilane (0.6 mL, 4.2 mmol). Compound 3h (130 mg, 0.38 mmol) was obtained as a colorless solid, in 73% yield, which was characterized as follows:
¹H NMR (500 MHz, D₂O) $\delta_H$ 2.32 (d, J=15.3, 1H, C(2')H$_a$), 2.56-2.61 (m, 1H, C(2')H$_b$), 3.52-3.61 (m, 2H, PCH₂), 4.01 (dd, J₁=10.5 Hz, J₂=3.6 Hz, 1H, C(4')H$_a$), 4.39-4.40 (m, 1H, C(3')H), 4.44 (dd, J1=10.7, J2=1.7 Hz, C(4') H$_b$), 6.06 (d, J=7.6 Hz, 1H, C-C(5)H), 6.20 (dd, J₁=7.8 Hz, J₂=2.0 Hz, 1H, C(1')H), 7.95 (d, J=7.6 Hz, 1H, C-C(6)H);
¹³C NMR (500 MHz, D₂O) $\delta_C$ 37.22 (C-2'), 64.88 (d, J=157.2 Hz, PCH₂), 74.37 (C-4'), 79.99 (d, J=11.7 Hz, C-3'), 86.71 (C-1'), 95.99 (C-C(5)), 143.02 (C-C(6), 157.56 (C-C(2)), 169.2 3(C-C(4));
³¹P NMR (500 MHz, D₂O) $\delta_p$ 15.96;
mass calcd for $C_9H_{13}N_3O_6P_1$ [M–H]⁻ 290.0535, found 290.0542.

EXAMPLE 4

Antiviral Activity

Compounds 3a-h were evaluated for their potential to inhibit the replication of HIV in a cell culture model for acute infection. The HIV-1 (III$_B$) virus stock and the HIV-2 (ROD) stock were obtained from the culture supernatant of HIV-1 or HIV-2 infected MT-4 cells, respectively. The inhibitory effect of the compounds on HIV-1 and HIV-2 replication was monitored by measuring the viability of MT-4 cells 5 days after infection. Cytotoxicity of the compounds was determined in parallel by measuring the viability of mock-infected cells on day 5, using a tetrazolium based colorimetric method to determine the number of viable cells.

PMDTA (abbreviation for compound 3e) shows an $IC_{50}$ value of 1.0 µg/mL both against HIV-1 and HIV-2. PMDTT (abbreviation for compound 3f) has an $IC_{50}$ value of 2.4 µg/mL against HIV-1 and HIV-2. No cytotoxicity was observed for PMDTA nor PMDTT at the highest concentration tested (125 µg/mL), giving the compounds a SI of >125 (PMDTA) and >50 (PMDTT) in these cellular systems.

In the cellular test system, both compounds are as active as PMEA and PMPA and their cytotoxicity is lower.

EXAMPLE 5

The nucleosides 106a and 106b were synthesized starting from (S)-β-Hydroxy-γ-butyrolactone (FIG. 1). The hydroxyl group in position 3 is protected by benzoylation and the lactone is reduced using Dibal-H in THF. The anomeric hydroxyl group is protected with acetic anhydride in pyridine. The nucleobase ($N^6$-benzoyladenine) is introduced using $SnCl_4$ as Lewis catalyst, giving a mixture of compound 104a and 104b with the base moiety in β and α configuration respectively.

Deprotection of 104a and 104b is done in one step, removing the benzoyl protecting groups with ammonia in methanol. Finally, the phosphonate function is introduced using the triflate of diisopropylphosphonomethyl alcohol and NaH in THF.

(S)-β-Benzoyloxy-γ-butyrolactone (101)

To the solution of (S)-(3-Hydroxy-γ-butyrolactone (1.0 g, 9.8 mmol) in 25 mL pyridine was added dropwise BzCl (1.4 mL, 12.2 mmol) at 0° C. The reaction mixture was warmed to room temperature and stirred overnight. The reaction was concentrated and coevaporated with toluene two times in vacuo. The residue was partitioned between $H_2O$ (15 mL) and EtOAc (40 mL). The organic layer was washed with water and brine, and concentrated in vacuo. The residue was purified by chromatography on a silica gel column (n-hexane/EtOAc=8:1) to afford 101 (1.78 g, 8.6 mmol) as a white solid, in 89% yield, which was characterized as follows:

$^1$H NMR (200 MHz, $CDCl_3$) $\delta_H$ 2.76-3.08 (m, 2H, C(2')$H_2$), 4.58-4.70 (m, 2H, C(4')$H_2$), 5.70-5.75 (m, 1H, C(3')H), 7.49-8.07 (m, 5H, Ar—H);

$^{13}$C NMR (200 MHz, $CDCl_3$) $\delta_H$ 33.21 (C-2'), 68.88 (C-4'), 71.73 (C-3'), 127.24 (arom-C), 128.43 (C-arom), 132.43 (C-arom), 169.05 (Bz-CO);

mass calcd. for $C_{11}H_{10}O_4Na_1$ 229.0477, found 229.0435.

3-O-benzoyl-2-deoxy-threose (102)

To a solution of 101 (0.780 g, 3.8 mmol) in 13 mL dry THF was slowly dropwise added 1.0 M diisopropyl aluminiumhydride (4.7 mL, 4.7 mmol) in toluene at −78° C. The reaction mixture was stirred at −78° C., and as soon as the starting material was completely consumed (TLC, 2 hours), methanol (2 mL) was slowly added in order to quench the reaction. The cooling bath was removed, 15 mL of a saturated aqueous sodium potassium tartrate solution and 25 mL of EtOAc were added and the mixture stirred vigorously for 3 hours. The organic layer was washed with water and brine, and concentrated under vacuo. The residue was purified by chromatography on a silica gel column (n-hexane/EtOAc=8:2) to afford 102 (590 mg, 2.8 mmol) as a colorless oil, in 75% yield, which was characterized as follows:

$^1$H NMR (200 MHz, $CDCl_3$) $\delta_H$ 2.30-2.40 (m, 2H, C(2')$H_2$), 4.05-4.36 (m, 2H, C(4')$H_2$), 5.30-5.82 (m, 2H, C(1'+3')H), 7.40-8.07 (m, 5H, Ar—H);

$^{13}$C NMR (200 MHz, $CDCl_3$) $\delta_H$ 71.38, 72.63, 73.94, 74.97, 128.44 (arom-C), 129.69 (arom-C), 133.27 (arom-C), 166.44 (Bz-CO);

mass calcd. for $C_{11}H_{12}O_4Na_1$ $[M+Na]^+$ 231.0633, found 231.0629.

1β-O-acetyl-3-O-benzoyl-2-deoxy-threose (103a) and 1α-O-acetyl-3-O-benzoyl-2-deoxy-threose (103b)

To the solution of 102 (150 mg, 0.72 mmol) in 6.5 mL $Et_3N$ was added dropwise $(CH_3CO)_2O$ (0.34 mL) and DMAP (8.8 mg, 0.072 mmol) at 0° C. the reaction mixture was warmed to room temperature and stirring for 3 hours. Then concentrated under vacuo and the residue was purified by chromatography on a silica gel column (n-hexane/EtOAc=9:1) to give compound 103a (117 mg, 0.47 mmol) as colorless oil, in 65% yield, and 103b (32 mg, 0.13 mmole) as colorless oil, in 18% yield, which were characterized as follows:

Compound 103a:

$^1$H NMR (200 MHz, $CDCl_3$) $\delta_H$ 2.07 (s, 3H, $CH_3$), 2.48-2.52 (m, 2H, C(2')$H_2$), 4.14 (dd, $J_1$=10.6 Hz, $J_2$=2.2 Hz, 1H, C(4')Hb), 4.26 (dd, $J_1$=10.6 Hz, $J_2$=4.2 Hz, 1H, C(4')Ha), 5.61-5.65 (m, 1H, C(3')H), 6.49 (t, J=4.0 Hz, 1H, C(1')H), 7.40-8.05 (m, 5H, Ar—H).

Compound 103b:

$^1$H NMR (200 MHz, $CDCl_3$) $\delta_H$ 2.07 (s, 3H, $CH_3$), 2.41-2.46 (m, 2H, C(2')$H_2$), 4.22 (dd, $J_1$=10.6 Hz, $J_2$=2.6 Hz, 1H, C(4')Hb), 4.36 (dd, $J_1$=10.6 Hz, $J_2$=5.2 Hz, 1H, C(4')Ha), 5.61-5.65 (m, 1H, C(3')H), 6.40 (d, J=4.4 Hz, 1H, C(1')H), 7.43-8.09 (m, 5H, Ar—H).

1β-($N^6$-benzoyladenin-9-yl)-3-O-benzoyl-2-deoxy-threose (104a) and 1α-($N^6$-benzoyladenin-9-yl)-3-O-benzoyl-2-deoxy-threose (104b)

To a mixture of 103 (210 mg, 0.84 mmol) and $N^6$-benzoyladenine (405 mg, 1.62 mmol) in dry MeCN (30 mL) was dropwise added $SnCl_4$ (0.3 mL, 2.5 mmol) under $N_2$ at 0° C. The reaction mixture was warmed to room temperature and stirred for 1.5 hours. Then the reaction was quenched with sat $NHCO_3$ and concentrated. The residue was partitioned between $H_2O$ (20 mL) and EtOAc (100 mL). The organic layer was washed with water and brine and concentrated under vacuum. The residue was purified by chromatography on a silica gel column ($CH_2Cl_2$:MeOH/40:0.5) to afford a mixture of β/α isomers (187 mg, 0.44 mmol) in 52% yield which were finally separated using preparative TLC and as eluent ($CH_2Cl_2$:MeOH/40:1) (3 times), which were characterized as follows:

Compound 104a:

H NMR (500 MHz, $CDCl_3$) $\delta_H$ 2.84-2.89 (m, 1H, C(2')Hb), 3.23-3.28 (m, 1H, C(2')Ha), 4.29 (d, J=10.6 Hz, 1H, C(4')Hb), 4.63 (dd, $J_1$=4.3, $J_2$=10.6 Hz, 1H, C(4')Ha), 5.92 (m, 1H, C(3')H), 6.50 (t, J=6.5 Hz, 1H, C(1')H), 7.45-8.15 (m, 10H, Ar—H);

$^{13}$C NMR (500 MHz, $CDCl_3$) $\delta_H$ 38.59 (0-2'), 73.43 (C-4'), 74.34 (C-3'), 85.15 (C-1'), 127.88 (arom-C), 128.45 (arom-C), 128.73 (arom-C), 129.64 (arom-C), 132.69 (arom-C), 133.40 (arom-C), 164.74 (Bz-CO), 166.00 (Bz-CO);

mass calcd. for $C_{23}H_{19}N_5O_4Na_1$ 452.1335, found 452.1339.

Compound 104b: $^1$H NMR (500 MHz, $CDCl_3$) $\delta_H$ 2.90-2.96 (m, 1H, C(2')Hb), 3.05 (d, J=15.4 Hz, 1H, C(2')Ha), 4.40 (dd, $J_1$=4.4 Hz, $J_2$=10.0 Hz, 1H, C(4')Hb), 4.46 (d, J=10.0 Hz, 1H, C(4')Ha), 5.74 (m, 1H, C(3')H), 6.56 (d, J=7.1 Hz, 1H, C(1')H), 7.38-8.03 (m, 10H, Ar—H);

$^{13}$C NMR (500 MHz, CDCl$_3$) $\delta_H$ 38.63 (0-2'), 73.45 (C-3'), 74.80 (C-4'), 85.19 (C-1'), 127.90 (arom-C), 128.59 (arom-C), 128.76 (arom-C), 129.36 (arom-C), 132.69 (arom-C), 133.54 (arom-C), 164.67 (Bz-CO), 165.79 (Bz-CO);

mass calcd. for C$_{23}$H$_{19}$N$_5$O$_4$Na1452.1335, found 452.1334.

1β-(adenin-9-yl)-2-deoxy-threose (105a) and 1α-(adenin-9-yl)-2-deoxy-threose (105b)

A solution of 104a (90 mg, 0.21 mmol) in methanol saturated with ammonium (26 mL) was stirred at room temperature overnight. The solution was concentrated under vacuum and the residue was purified by column chromatography (CH$_2$Cl$_2$:MeOH/9:1) to give compound 105a (40 mg, 0.18 mmol) as a white solid, in 86% yield, which was characterized as follows:

$^1$H NMR (200 MHz, DMSO-d$_6$) $\delta_H$ 2.27-2.34 (m, 1H, C(2')Hb), 2.78-2.85 (m, 1H, C(2')Ha), 3.76 (d, J=8.8 Hz, 1H, C(4')Hb), 4.21 (dd, $J_1$=3.6, $J_2$=8.8 Hz, 1H, C(4')Ha), 4.62 (bs, 1H, OH), 5.20 (d, J=3.6 Hz, 1H, C(3')H), 6.37 (t, J=8.6 Hz, 1H, C(1')H), 7.26 (bs, 2H, NH$_2$), 8.14 (s, 1H, H-8), 8.30 (s, 1H, H-2).

Compound 105b was prepared as described for 105a using 104b (110 mg, 0.26 mmol) as starting material and was obtained (48 mg, 0.22 mmol) as a white solid in 86% yield, which was characterized as follows:

$^1$H NMR (200 MHz, DMSO-d$_6$) $\delta_H$ 2.23-2.30 (m, 1H, C(2')Hb), 2.63-2.71 (m, 1H, C(2')Ha), 3.90-3.93 (m, 2H, C(4')H$_2$), 4.45 (m, 1H, OH), 5.80 (d, J=4.4 Hz, 1H, C(3')H), 6.26 (dd, $J_1$=2.2 Hz, $J_2$=8.0 Hz, 1H, C(1')H), 7.28 (s, 2H, NH$_2$), 8.13 (s, 1H, H-8), 8.35 (s, 1H, H-2);

$^{13}$C NMR (200 MHz, DMSO-d$_6$) $\delta_H$ 38.49 (C-2'), 66.99 (C-3'), 74.04 (C-4'), 80.90 (C-1'), 137.54 (C-8), 150.19 (C-2), 153.90 (C-6).

1β-(adenine-9-yl)-3-(diisopropylphosphonomethyl)-threose (106a) and 1α-(adenine-9-yl)-3-(diisopropylphosphonomethyl)-threose (106b)

To the solution of 105a (50 mg, 0.23 mmol) in 5 mL THF, which was cooled using dry-ice and acetone, was added sodium hydride 80% (11.4 mg, 0.46 mmol). The mixture was stirred for 10 min and the solution of thriflourate phosphonate (136 mg, 0.46 mmol) in THF was slowly dropped to the reaction flask. Then the mixture was slowly warm to room temperature. The reaction was quenched with sat. NaHCO$_3$ and concentrated. The residue was partitioned between H$_2$O and CH$_2$Cl$_2$. The organic layer was washed with water and brine, and concentrated in vacuo. The residue was purified by chromatography on a silica gel column (CH$_2$Cl$_2$/MeOH=98:2) to afford 106a as a white solid. Compound 106b was prepared as described for 106a using 105b as starting material and was obtained as a white solid, which was characterized as follows:

$^1$H NMR (200 MHz, CDCl$_3$) $\delta_H$ 1.25-1.35 (m, 12H, CH$_3$), 2.57-2.62 (m, 2H, C(2')H$_2$), 3.70 (dd, $J_1$=1.4 Hz, $J_2$=8.8 Hz, 2H, PCH$_2$), 4.04 (dd, $J_1$=4.2 Hz, $J_2$=10.4 Hz, C(4')Ha), 4.37 (d, J=10.4 Hz, C(4')Hb), 4.47 (m, 1H, C(3')H, 4.71-4.78 (m, 2H, OCH(CH$_3$)$_2$), 5.75 (m, 2H, NH$_2$), 6.47 (dd, $J_1$=2.7 Hz, $J_2$=7.0 Hz, C(1')H), 8.29 (s, 1H, H-8), 8.34 (s, 1H, H-2).

EXAMPLE 6

Incorporation of PMDTA into DNA Using Reverse Transcriptase

The antiviral activity of the phosphonate nucleosides of the invention may be mostly explained by their intracellular metabolisation into their diphosphates (hereinafter referred as pp) followed by incorporation into the viral genome and chain termination. We used a primer/extension assay in order to compare the ability of the HIV reverse transcriptase and the human DNA polymerase-α to accept PMDTApp (see FIG. 15) as a substrate in comparison to deoxyadenosine triphosphate (hereinafter referred as dATP). This will provide us with suitable information about the selectivity of the anti-HIV compound of the invention since the human DNA polymerase-α is mainly involved in replication of the nuclear genome while the HIV reverse transcriptase plays a key role in the replication of the viral genome.

The following incorporation study was effected with a DNA template and a DNA primer, as DNA polymerase-α and reverse transcriptase are both able to synthesize double stranded DNA (although reverse transcriptase is also able to synthesize a DNA strand using RNA as template). Both enzymes were able to extend a DNA primer with the phosphonate nucleotide, but the modified nucleotide was only a very poor substrate for the human DNA polymerase α. Only a high enzyme concentration (0.4 U/μL) resulted in the incorporation of PMDTApp, i.e. a concentration more than 100 times higher than the concentration used to incorporate the natural dATP substrate.

The HIV reverse transcriptase, on the other hand, accepted PMDTApp as easily as the natural building block. These results from primer/extension assays were confirmed by the following kinetic data.

Determination of K$_m$ and K$_{cat}$ values for the incorporation of dATP and PMDTApp in a DNA hybrid was carried out under steady-state conditions as described by Creighton et al. in *Methods in Enzymology* (1995) 262:232-256. For each determination eight different substrate concentrations in the range of 0.1 to 12.5 μM were used. Results given below are the average of three independent determinations. The reaction mixture contained 250 nM primer/template complex 0.025 U/μL HIV reverse transcriptase, and the triphosphate nucleotides to be incorporated (dATP and PMDTApp, respectively). The template sequence and the primer sequence used in this experiment are shown below. The reaction was quenched after 1, 2 and 3 minutes by adding a double volume of stop solution (90% formamide, 0.05% bromophenol blue, 0.05% xylene cyanol and 50 mM EDTA). Samples were analyzed by gel electrophoresis on a 16% polyacrylamide ureum gel in TBE buffer (89 mM Tris-borate, 2 mM EDTA buffer, pH 8.3) after heating the samples for 5 minutes at 70° C. Products were visualised by phosphorimaging. The amount of radioactivity in the bands corresponding to the products of the enzymatic reactions was determined using the Optiquant Image Analysis Software (Packard). Rate profiles were determined using GraphPad Prism® software.

Results of this experiment are shown in the Table below. These data show, for the incorporation of PMDTApp by the HIV reverse transcriptase, a small increase in K$_m$ value but also a slight increase in k$_{cat}$ value, compared to dATP. This indicates that, although the affinity of the enzyme for the phosphonate nucleotide of the invention might be slightly lower, the overall catalytic efficiency differs only with a factor of 2.5.

Since PMDTApp was such a poor substrate for the DNA polymerase-α, kinetic parameters could not be determined under steady-state conditions.

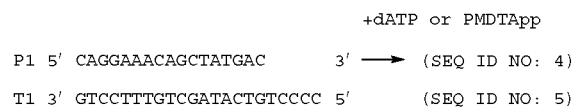

| | $K_m$ (in μM) | $K_{cat}$ (in min-1) | $K_{cat}/k_m$ (in min$^{-1}$, M$^{-1}$) |
|---|---|---|---|
| dATP | 0.10 | 0.66 | 6.6 |
| PMDTApp | 0.29 | 0.79 | 2.72 |

These data show that PMDTA can be incorporated into DNA, functioning as a chain terminator. A model was then built in order to analyse interactions between the incorporated nucleotide and reverse transcriptase. Therefore the adenine phosphonate nucleoside was built at the 3'-end of the primer and paired with a thymidine nucleotide in the template strand. This model revealed that the sugar ring is puckered in the C3'-endo conformation. Hydrophobic interactions between the phosphonate nucleotide and reverse transcriptase are occurring at Leu74, Tyr115 and Gln151, while no steric hindrance with Met184 is expected to occur during translocation. This model visualizes the experimental results of the incorporation study of PMDTA into DNA using reverse transcriptase.

The invention claimed is:

1. A compound represented by the general formula (II):

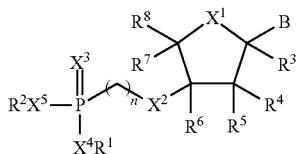 (II)

wherein:

$X^1$, $X^2$, $X^3$, $X^4$ and $X^5$ are each —O—,

B is selected from the group consisting of adeninyl, thyminyl, uracilyl, cytosinyl and guaninyl, $R^1$ and $R^2$ are each independently selected from the group consisting of hydrogen, alkyl and P(O)(OH)—O—$PO_3H_2$, provided that when one of $R^1$ and $R^2$ is P(O)(OH)—O—$PO_3H_2$, the other one is hydrogen;

$R^4$ and $R^5$ are each independently selected from the group consisting of hydrogen and $OR^{14}$;

$R^3$, $R^6$, $R^7$ and $R^8$ are each hydrogen;

$R^{14}$ is hydrogen or arylalkyl; and n is an integer representing the number of methylene groups between $X_2$ and P, and is selected from 1, 2, 3, 4, 5 and 6;

and pharmaceutically acceptable salts and stereoisomers thereof.

2. The compound of claim 1, being represented by one of the general formulae (III) to (XVIII):

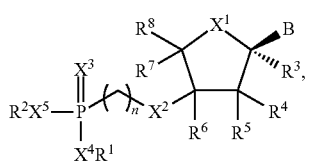 (III)

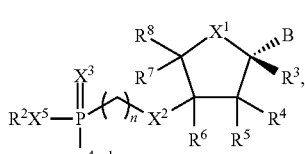 (IV)

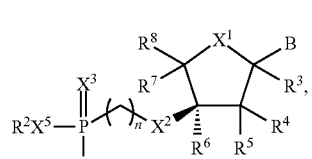 (V)

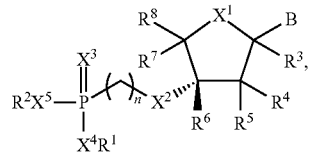 (VI)

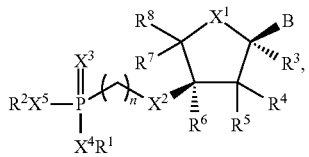 (VII)

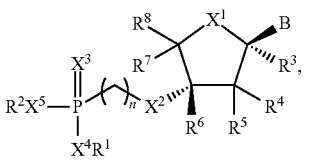 (VIII)

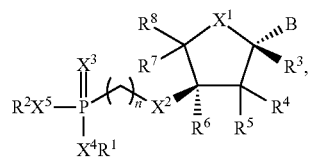 (IX)

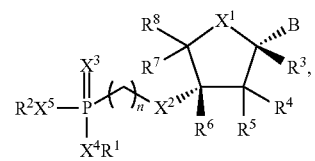 (X)

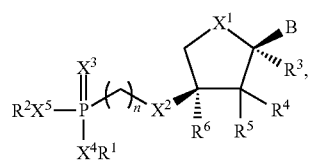 (XI)

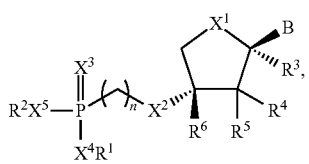 (XII)

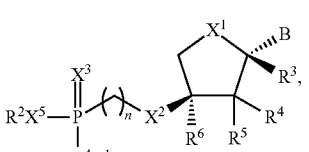 (XIII)

-continued

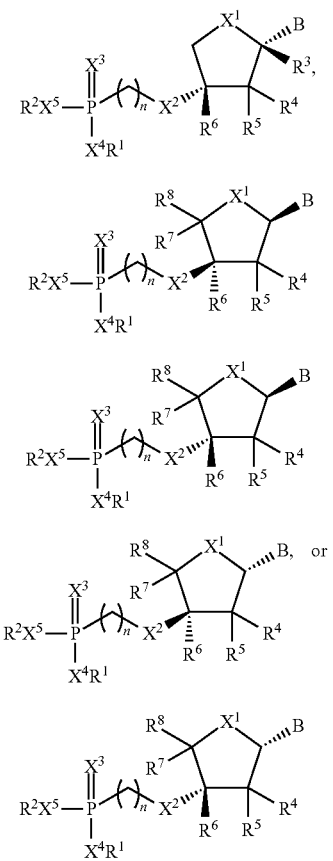

(XIV)

(XV)

(XVI)

(XVII)

(XVIII)

wherein n, B, $X^1$, $X^2$, $X^3$, $X^4$, $X^5$, $R^1$, $R^2$, $R^3$, $R^4$, $R^5$, $R^6$, $R^7$, $R^8$ and $R^{14}$ are defined as in formula (II), and pharmaceutically acceptable salts and stereoisomers thereof.

3. The compound of claim 2, wherein $R^1$ and $R^2$ are each isopropyl.

4. The compound of claim 2, wherein $R^{14}$ is benzyl.

5. The compound of claim 2, wherein n is 1.

6. The compound of claim 1, wherein $R^1$ and $R^2$ are each isopropyl.

7. The compound of claim 1, wherein $R^{14}$ is benzyl.

8. The compound of claim 1, wherein n is 1.

9. A method of treatment of a retroviral infection in a mammal in need thereof comprising the administration of a compound according to claim 1.

10. A method of treatment of an infection by the Human Immunodeficiency Virus (HIV) in a host in need thereof comprising the administration of a compound according to claim 1.

11. A pharmaceutical composition comprising a compound according to claim 1 as an active ingredient in admixture with at least one pharmaceutically acceptable carrier.

12. A compound represented by one of the following general formulae (XXXI) to (XXXVI):

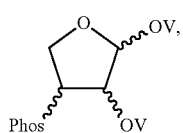

(XXXI)

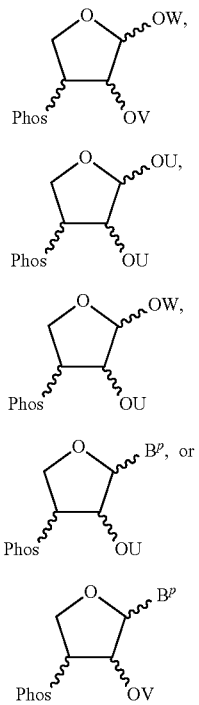

(XXXII)

(XXXIII)

(XXXIV)

(XXXV)

(XXXVI)

wherein:
U is an acyl or benzyl group,
V is a trimethylsilyl or tert-butyldimethylsilyl group,
W is a methyl group,
the snake-like symbol means any stereochemical arrangement of the respective bond,
$B^p$ is an optionally protected heterocyclic nucleobase moiety selected from the group consisting of adeninyl, thyminyl, uracilyl, cytosinyl and guaninyl, and
Phos is a phosphonate group having the following structure

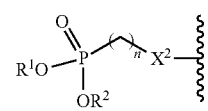

wherein $X^2$ is —O—; $R^1$ and $R^2$ are each independently selected from the group consisting of hydrogen, alkyl and $P(O)(OH)$—O—$PO_3H_2$, provided that when one of $R^1$ and $R^2$ is $P(O)(OH)$—O—$PO_3H_2$, the other one is hydrogen; and n is an integer representing the number of methylene groups between $X^2$ and P and is selected from 1, 2, 3, 4, 5 and 6.

13. The compound of claim 12, wherein n is 1.

14. A method of treatment of an infection by the Human Immunodeficiency Virus (HIV) in a host in need thereof comprising the administration of a compound according to claim 2.

15. A method of treatment of a retroviral infection in a mammal in need thereof comprising the administration of a compound according to claim 2.

16. A pharmaceutical composition comprising a compound according to claim 2 as an active ingredient in admixture with at least one pharmaceutically acceptable carrier.

* * * * *

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial
<220> FEATURE:
<223> OTHER INFORMATION: Hepatitis B virus forward primer

<400> SEQUENCE: 1
ccgtctgtgc cttctcatct g                                      21

<210> SEQ ID NO 2
<211> LENGTH: 29
<212> TYPE: DNA
<213> ORGANISM: Artificial
<220> FEATURE:
<223> OTHER INFORMATION: Hepatitis B virus reverse primer

<400> SEQUENCE: 2
agtccaagag tyctcttatr yaagaccttt                             29

<210> SEQ ID NO 3
<211> LENGTH: 26
<212> TYPE: DNA
<213> ORGANISM: Artificial
<220> FEATURE:
<223> OTHER INFORMATION: Hepatitis B virus Taqman probe

<400> SEQUENCE: 3
ccgtgtgcac ttcgcttcac ctctgc                                 26

<210> SEQ ID NO 4
<211> LENGTH: 17
<212> TYPE: DNA
<213> ORGANISM: Artificial
<220> FEATURE:
<223> OTHER INFORMATION: substrate for DNA polymerase alpha

<400> SEQUENCE: 4
caggaaacag ctatgac                                           17

<210> SEQ ID NO 5
<211> LENGTH: 22
<212> TYPE: DNA
```

```
<213> ORGANISM: Artificial
<220> FEATURE:
<223> OTHER INFORMATION: substrate for DNA polymerase alpha

<400> SEQUENCE: 5 ccctgtcat agctgtttcc tg                                         22
```